United States Patent
Hargis et al.

(10) Patent No.: US 10,401,617 B2
(45) Date of Patent: Sep. 3, 2019

(54) LASER SYSTEMS AND OPTICAL DEVICES FOR MANIPULATING LASER BEAMS

(71) Applicant: CVI LASER, LLC, Albuquerque, NM (US)

(72) Inventors: David E. Hargis, San Diego, CA (US); John O'Shaughnessy, Carlsbad, CA (US)

(73) Assignee: CVI LASER, LLC, Albuquerque, NM (US)

( * ) Notice: Subject to any disclaimer, the term of this patent is extended or adjusted under 35 U.S.C. 154(b) by 0 days.

(21) Appl. No.: 16/028,267

(22) Filed: Jul. 5, 2018

(65) Prior Publication Data

US 2018/0329203 A1 Nov. 15, 2018

Related U.S. Application Data

(62) Division of application No. 15/067,818, filed on Mar. 11, 2016, now Pat. No. 10,114,213.
(Continued)

(51) Int. Cl.
*G02B 26/08* (2006.01)
*H01S 3/23* (2006.01)
(Continued)

(52) U.S. Cl.
CPC ..... *G02B 26/0875* (2013.01); *G01N 21/6402* (2013.01); *G02B 27/1006* (2013.01);
(Continued)

(58) Field of Classification Search
CPC ............ G02B 26/0875; G02B 27/1006; G02B 27/141; G02B 27/30; G01N 21/6402;
(Continued)

(56) References Cited

U.S. PATENT DOCUMENTS 4,296,995 A 10/1981 Bickel
4,550,240 A 10/1985 Toida et al.
(Continued)

FOREIGN PATENT DOCUMENTS

DE 41 13 279 10/1992
DE 195 08 754 6/1999
(Continued)

OTHER PUBLICATIONS

Olympus Confocal Laser Scanning Biological Microscope, FV1000, Fluoview—Always Evolving, available at http://www.olympusamerica.com/files/seg_bio/fv1000_brochure.pdf.
(Continued)

*Primary Examiner* — Euncha P Cherry
(74) *Attorney, Agent, or Firm* — Knobbe, Martens, Olson & Bear, LLP

(57) ABSTRACT

Various embodiments of a multi-laser system are disclosed. In some embodiments, the multi-laser system includes a plurality of lasers, a plurality of laser beams, a beam positioning system, a thermally stable enclosure, and a temperature controller. The thermally stable enclosure is substantially made of a material with high thermal conductivity such as at least 5 W/(m K). The thermally stable enclosure can help maintain alignment of the laser beams to a target object over a range of ambient temperatures. Various embodiments of an optical system for directing light for optical measurements such laser-induced fluorescence and spectroscopic analysis are disclosed. In some embodiments, the optical system includes a thermally conductive housing and a thermoelectric controller, a plurality of optical fibers, and one or more optical elements to direct light emitted by the optical fibers to illuminate a flow cell. The housing is configured to attach to a flow cell.

10 Claims, 37 Drawing Sheets

Related U.S. Application Data

(60) Provisional application No. 62/133,241, filed on Mar. 13, 2015, provisional application No. 62/135,137, filed on Mar. 18, 2015.

(51) Int. Cl.
*G02B 27/10* (2006.01)
*G02B 27/14* (2006.01)
*G02B 27/30* (2006.01)
*H01S 3/02* (2006.01)
*H01S 3/04* (2006.01)
*G01N 21/64* (2006.01)
*H01S 3/00* (2006.01)

(52) U.S. Cl.
CPC ........... *G02B 27/141* (2013.01); *G02B 27/30* (2013.01); *H01S 3/027* (2013.01); *H01S 3/0405* (2013.01); *H01S 3/2391* (2013.01); *H01S 3/005* (2013.01); *H01S 3/0071* (2013.01)

(58) Field of Classification Search
CPC ...... H01S 3/027; H01S 3/0405; H01S 3/2391; H01S 3/005; H01S 3/0071
USPC ....................................................... 359/556.2
See application file for complete search history.

(56) References Cited

U.S. PATENT DOCUMENTS

| | | | |
|---|---|---|---|
| 4,573,465 A | 3/1986 | Sugiyama et al. |
| 4,632,554 A | 12/1986 | Pearce |
| 4,722,591 A | 2/1988 | Haffner |
| 4,817,101 A | 3/1989 | Wyeth et al. |
| 4,826,299 A | 5/1989 | Powell |
| 4,938,593 A | 7/1990 | Morris et al. |
| 4,983,042 A | 1/1991 | Korner et al. |
| 5,106,192 A | 4/1992 | Tucker et al. |
| 5,109,447 A | 4/1992 | Can |
| 5,147,349 A | 9/1992 | Johnson et al. |
| 5,152,759 A | 10/1992 | Parel et al. |
| 5,258,989 A | 11/1993 | Raven |
| 5,260,578 A | 11/1993 | Bliton et al. |
| 5,289,557 A | 2/1994 | Sheinis et al. |
| 5,295,143 A | 3/1994 | Rao et al. |
| 5,304,167 A | 4/1994 | Freiberg |
| 5,325,393 A | 6/1994 | Nighan, Jr. et al. |
| 5,343,038 A | 8/1994 | Nishiwaki et al. |
| 5,394,492 A | 2/1995 | Hwang |
| 5,446,532 A | 8/1995 | Yamazaki |
| 5,491,344 A | 2/1996 | Kenny et al. |
| 5,544,271 A | 8/1996 | Lim |
| 5,617,500 A | 4/1997 | Shionoya et al. |
| 5,633,695 A | 5/1997 | Feke et al. |
| 5,659,642 A | 8/1997 | King et al. |
| 5,668,903 A | 9/1997 | Neuberger et al. |
| 5,674,698 A | 10/1997 | Zarling et al. |
| 5,698,397 A | 12/1997 | Zarling et al. |
| 5,736,410 A | 4/1998 | Zarling et al. |
| 5,771,325 A | 6/1998 | Neuberger |
| 5,814,820 A | 9/1998 | Dong et al. |
| 5,823,942 A | 10/1998 | Toida |
| 5,824,269 A | 10/1998 | Kosaka et al. |
| 5,866,911 A | 2/1999 | Baer |
| 5,883,378 A | 3/1999 | Irish et al. |
| 5,952,668 A | 9/1999 | Baer |
| 6,048,444 A | 4/2000 | Takahashi et al. |
| 6,081,544 A | 6/2000 | Zamel et al. |
| 6,101,201 A | 8/2000 | Hargis et al. |
| 6,110,165 A | 8/2000 | Ota |
| 6,133,995 A | 10/2000 | Kubota |
| 6,175,440 B1 | 1/2001 | Conemac |
| 6,214,033 B1 | 4/2001 | Li et al. |
| 6,215,807 B1 | 4/2001 | Reilly |
| 6,221,671 B1 | 4/2001 | Groner et al. |
| 6,222,961 B1 | 4/2001 | Engelhardt et al. |
| 6,462,345 B1 | 10/2002 | Simon et al. |
| 6,480,513 B1 | 11/2002 | Kapany et al. |
| 6,490,309 B1 | 12/2002 | Okazaki et al. |
| 6,510,001 B1 | 1/2003 | Engelhardt et al. |
| 6,557,369 B1 | 5/2003 | Phelps et al. |
| 6,592,822 B1 | 7/2003 | Chandler |
| 6,603,780 B2 | 8/2003 | Miyai |
| 6,614,031 B2 | 9/2003 | Engelhardt et al. |
| 6,654,165 B2 | 11/2003 | Engelhardt et al. |
| 6,677,566 B2 | 1/2004 | Knebel et al. |
| 6,737,635 B2 | 5/2004 | Engelhardt et al. |
| 6,750,457 B2 | 6/2004 | Heffelfinger et al. |
| 6,836,489 B2 | 12/2004 | Nishimura et al. |
| 6,867,899 B2 | 3/2005 | Knebel |
| 6,867,919 B2 | 3/2005 | Seyfried |
| 6,920,159 B2 | 7/2005 | Sidorin et al. |
| 6,958,470 B2 | 10/2005 | Hoffmann |
| 6,980,293 B1 | 12/2005 | Harada |
| 7,005,654 B2 | 2/2006 | Seyfried |
| 7,098,447 B2 | 8/2006 | Moellmann |
| 7,133,130 B2 | 11/2006 | Storz et al. |
| 7,151,633 B2 | 12/2006 | Storz et al. |
| 7,280,567 B2 | 10/2007 | Ningyi et al. |
| 7,280,570 B2 | 10/2007 | Seyfried et al. |
| 7,330,493 B2 | 2/2008 | Ningyi et al. |
| 7,394,063 B2 | 7/2008 | Schreiber |
| 7,426,027 B2 | 9/2008 | Noguchi et al. |
| 7,428,104 B2 | 9/2008 | Engelhardt |
| 7,430,231 B2 | 9/2008 | Ningyi et al. |
| 7,433,119 B2 | 10/2008 | Gugel |
| 7,457,330 B2 | 11/2008 | Ningyi et al. |
| 7,468,998 B2 | 12/2008 | Ningyi et al. |
| 7,474,462 B2 | 1/2009 | Ulrich et al. |
| 7,489,429 B2 | 2/2009 | Scaggs |
| 7,505,495 B2 | 3/2009 | Fratti et al. |
| 7,522,651 B2 | 4/2009 | Ningyi et al. |
| 7,535,937 B2 | 5/2009 | Ningyi et al. |
| 7,535,938 B2 | 5/2009 | Ningyi et al. |
| 7,542,489 B2 | 6/2009 | Ningyi et al. |
| 7,548,567 B2 | 6/2009 | Kupershmidt et al. |
| 7,564,624 B2 | 7/2009 | Leimbach et al. |
| 7,599,115 B2 | 10/2009 | Gugel |
| 7,599,413 B2 | 10/2009 | Ningyi et al. |
| 7,606,273 B2 | 10/2009 | Sheng-Bai et al. |
| 7,633,979 B2 | 12/2009 | Ningyi et al. |
| 7,660,035 B2 | 2/2010 | Bohm et al. |
| 7,724,363 B2 | 5/2010 | Wachsmuth et al. |
| 7,733,932 B2 | 6/2010 | Faybishenko |
| 7,742,226 B2 | 6/2010 | Bewersdorf et al. |
| 7,813,390 B2 | 10/2010 | Ningyi et al. |
| 7,835,601 B2 | 11/2010 | Seyfried et al. |
| 7,899,105 B1 | 3/2011 | Hargis et al. |
| 7,903,706 B2 | 3/2011 | O'Shaughnessy et al. |
| 7,949,025 B2 | 5/2011 | Olea |
| 7,999,935 B2 | 8/2011 | Dyba |
| 8,238,389 B2 | 8/2012 | Hargis et al. |
| 8,403,543 B2 | 3/2013 | Kim et al. |
| 8,794,802 B2 | 8/2014 | Wu et al. |
| 8,975,572 B2 | 3/2015 | Hargis |
| 9,014,224 B2 | 4/2015 | O'Shaughnessy |
| 9,413,130 B2 | 8/2016 | Hargis et al. |
| 2001/0017868 A1 | 8/2001 | Kraenert et al. |
| 2001/0021210 A1 | 9/2001 | Nakaya et al. |
| 2002/0061032 A1 | 5/2002 | Miura et al. |
| 2002/0097772 A1 | 7/2002 | Dautremont-Smith et al. |
| 2003/0058530 A1 | 3/2003 | Kawano |
| 2003/0214987 A1 | 11/2003 | Yamanaka et al. |
| 2004/0027631 A1 | 2/2004 | Nagano et al. |
| 2004/0210289 A1 | 10/2004 | Wang et al. |
| 2005/0180474 A1 | 8/2005 | Buchold et al. |
| 2005/0201441 A1 | 9/2005 | Seyfried et al. |
| 2005/0220458 A1 | 10/2005 | Kupershmidt et al. |
| 2005/0281298 A1 | 12/2005 | Kupershmidt et al. |
| 2006/0097188 A1 | 5/2006 | Seyfried |
| 2006/0239317 A1 | 10/2006 | Yoshida et al. |
| 2006/0245049 A1 | 11/2006 | Knebel |
| 2006/0273260 A1 | 12/2006 | Casstevens et al. |
| 2007/0024978 A1 | 2/2007 | Jackson et al. |

(56) References Cited

U.S. PATENT DOCUMENTS

| | | |
|---|---|---|
| 2007/0195850 A1 | 8/2007 | Schluter et al. |
| 2008/0025677 A1 | 1/2008 | Sasaki |
| 2008/0089369 A1 | 4/2008 | Ningyi et al. |
| 2009/0097507 A1 | 4/2009 | Zhu et al. |
| 2009/0257054 A1* | 10/2009 | Hargis .................. G01J 3/10 356/246 |
| 2009/0274176 A1 | 11/2009 | O'Shaughnessy et al. |
| 2009/0323203 A1 | 12/2009 | Adams et al. |
| 2010/0006772 A1 | 1/2010 | Gugel |
| 2010/0073757 A1 | 3/2010 | Birk et al. |
| 2010/0111768 A1 | 5/2010 | Banerjee et al. |
| 2010/0177375 A1 | 7/2010 | Seyfried |
| 2010/0232011 A1 | 9/2010 | Seyfried |
| 2011/0063832 A1 | 3/2011 | Hu |
| 2011/0222054 A1 | 9/2011 | Krishnamachari |
| 2011/0273768 A1 | 11/2011 | Krishnamachari et al. |
| 2012/0099318 A1 | 4/2012 | Liu |
| 2014/0160786 A1 | 6/2014 | Hargis |
| 2016/0028210 A1 | 1/2016 | O'Shaughnessy |
| 2016/0334618 A1 | 11/2016 | Hargis et al. |

FOREIGN PATENT DOCUMENTS

| | | |
|---|---|---|
| JP | 07 318810 | 12/1995 |
| WO | WO 2010065779 | 6/2010 |

OTHER PUBLICATIONS

Powell Lens Buyer's Guide, downloaded from http://www.laserlineoptics.com/powell_primer.html on Mar. 13, 2015.

* cited by examiner

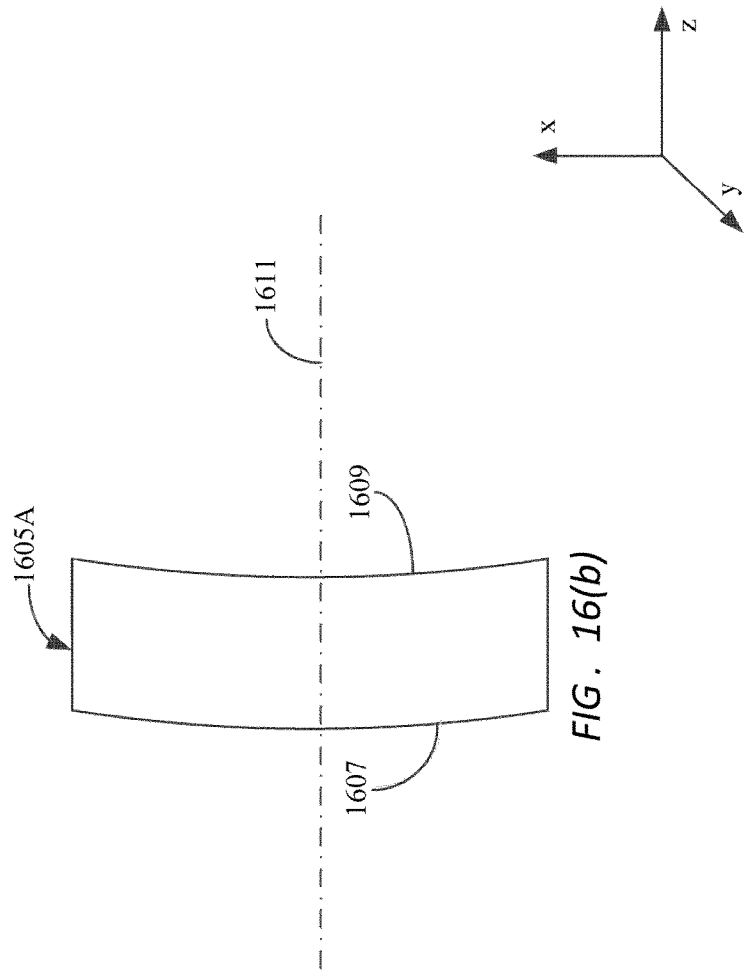
FIG. 16(b)
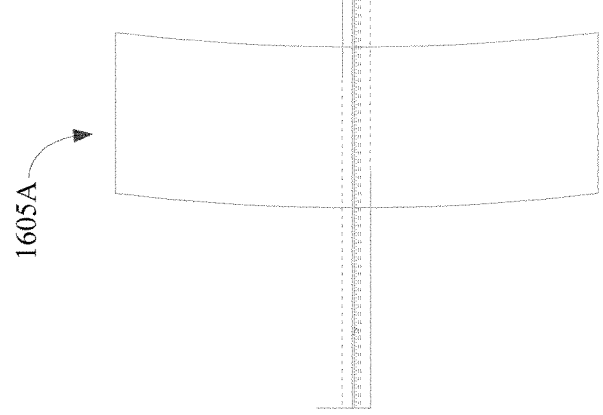
FIG. 16(c-1)

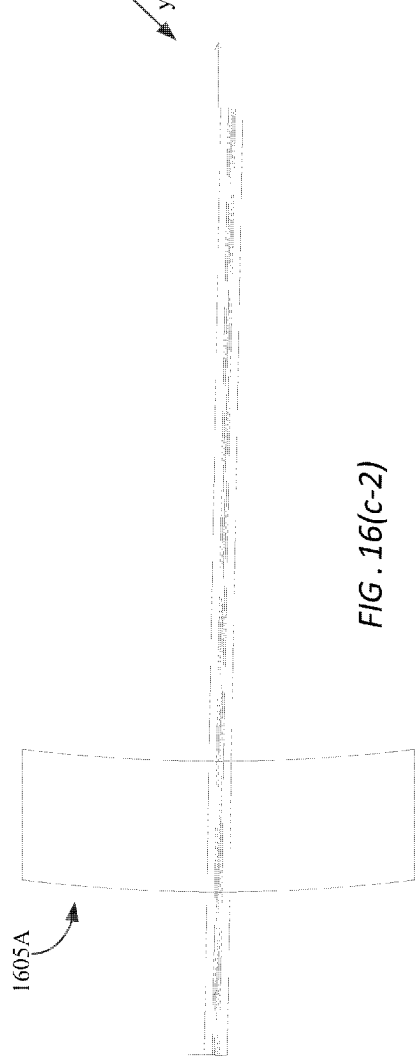
FIG. 16(c-2)
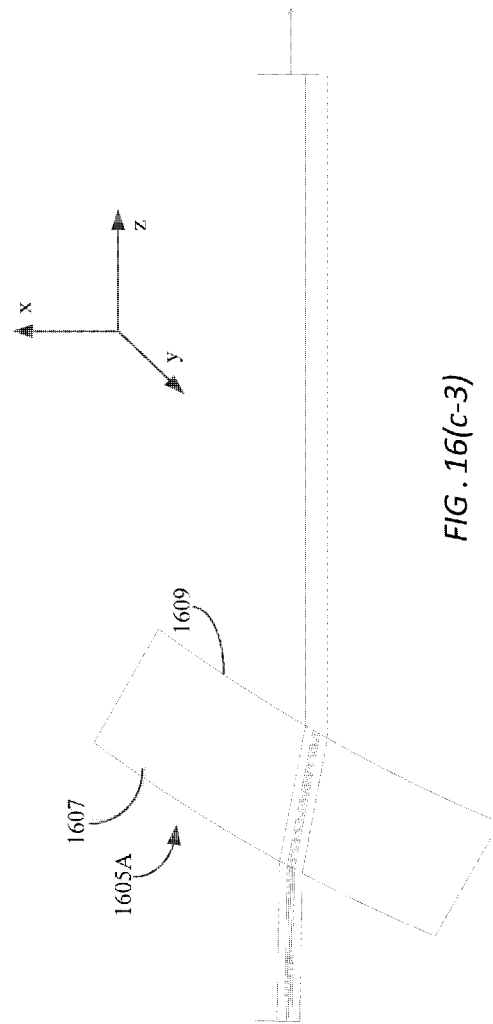
FIG. 16(c-3)

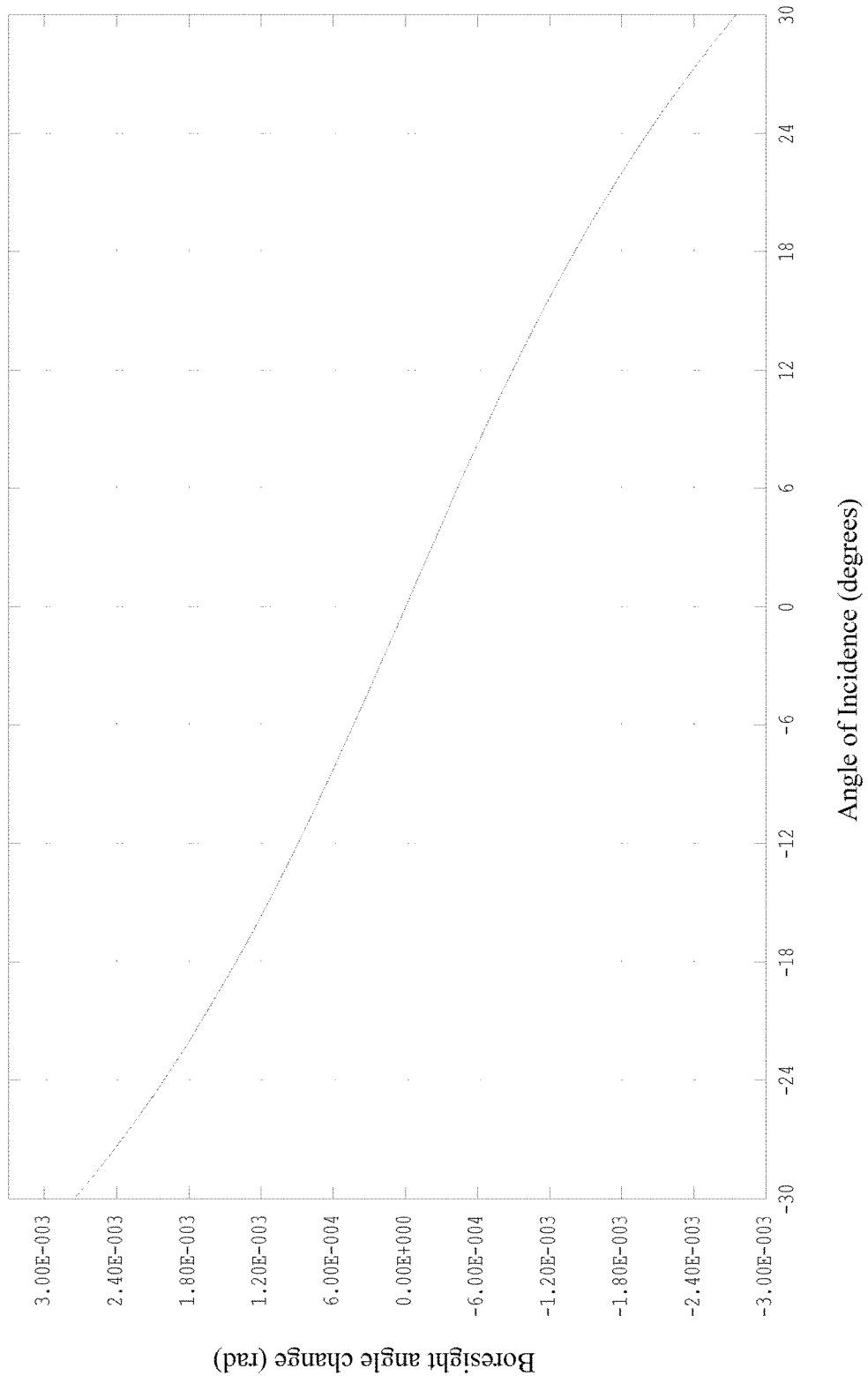
FIG. 16(d-1)

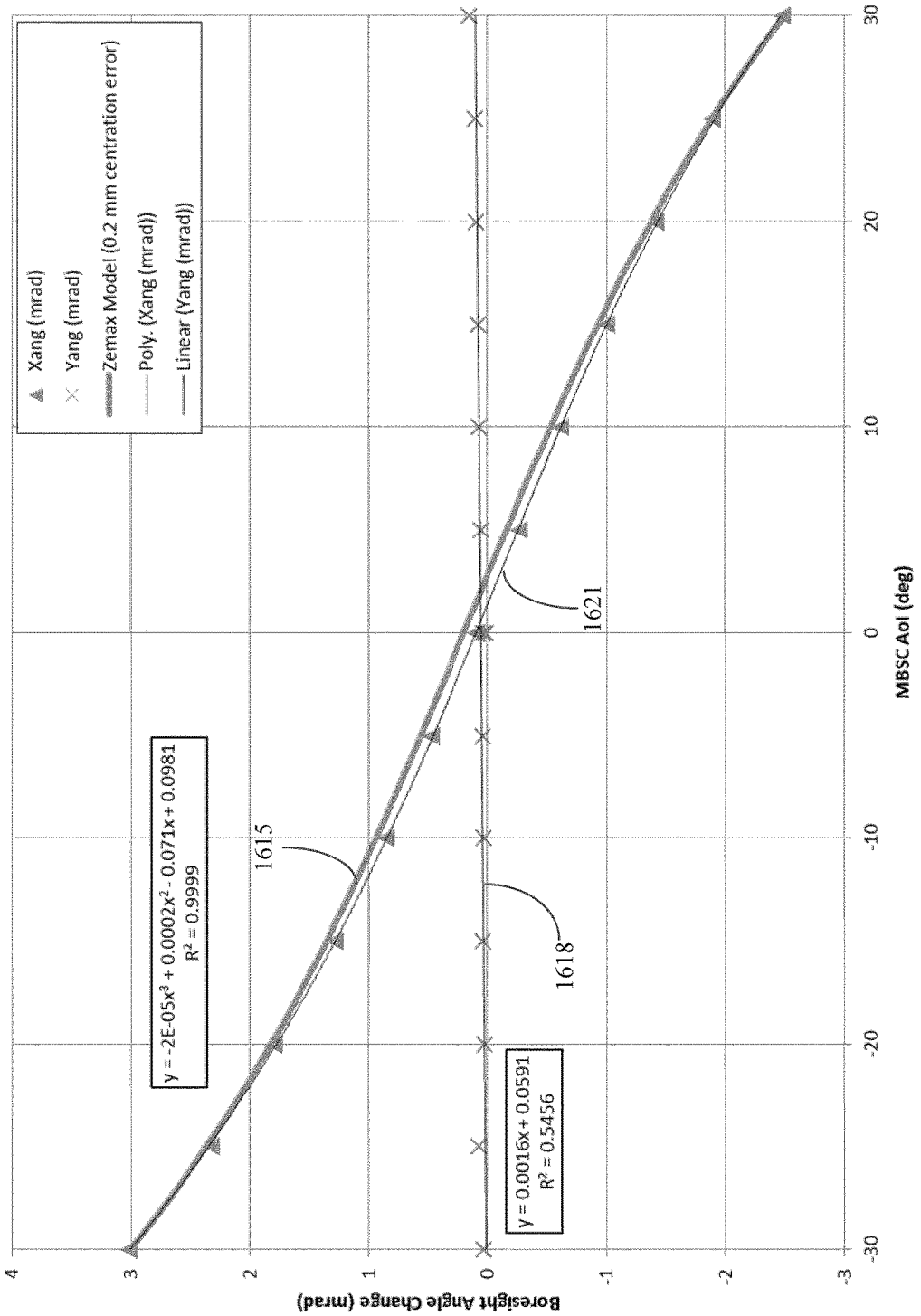
FIG. 16(d-2)

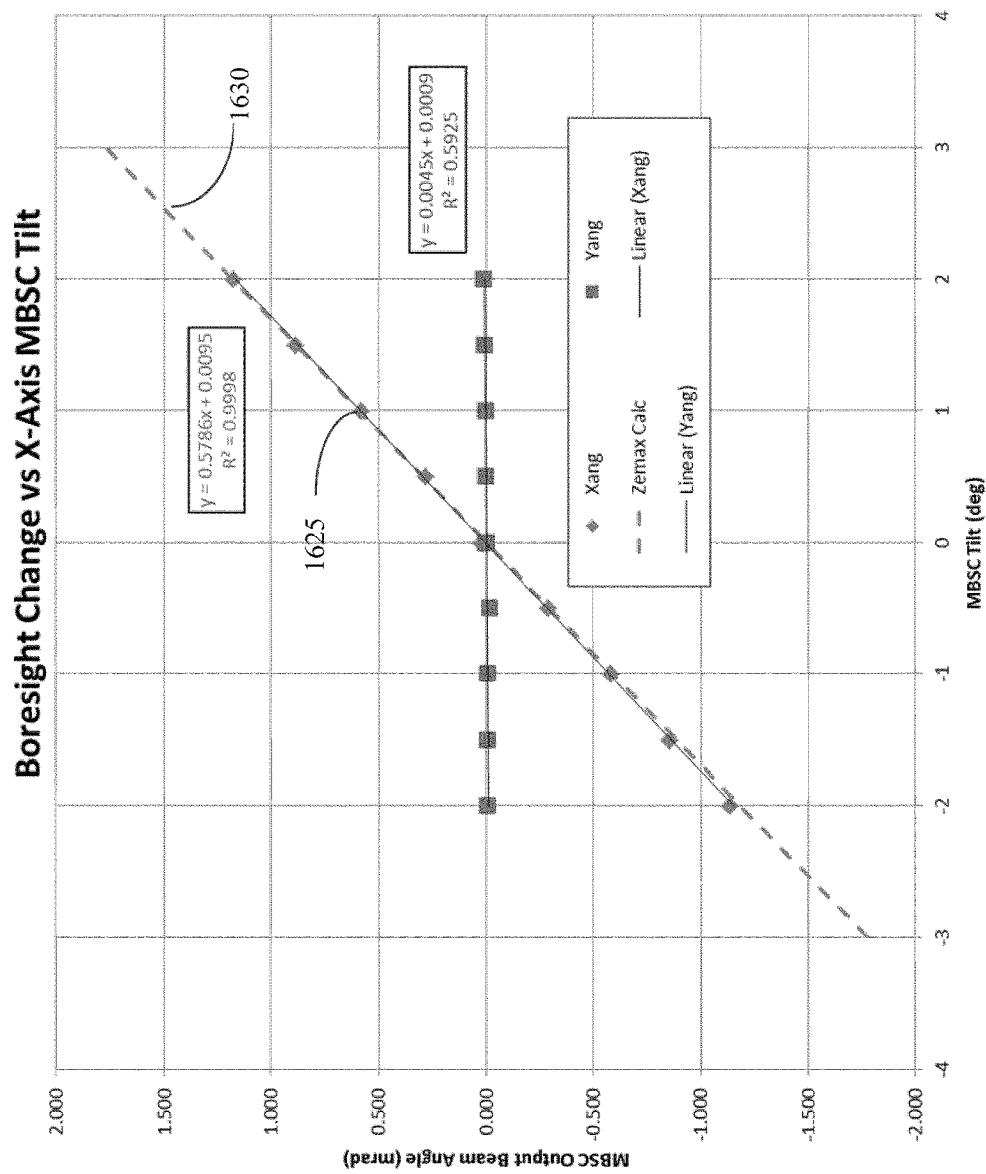
FIG. 16(d-3)

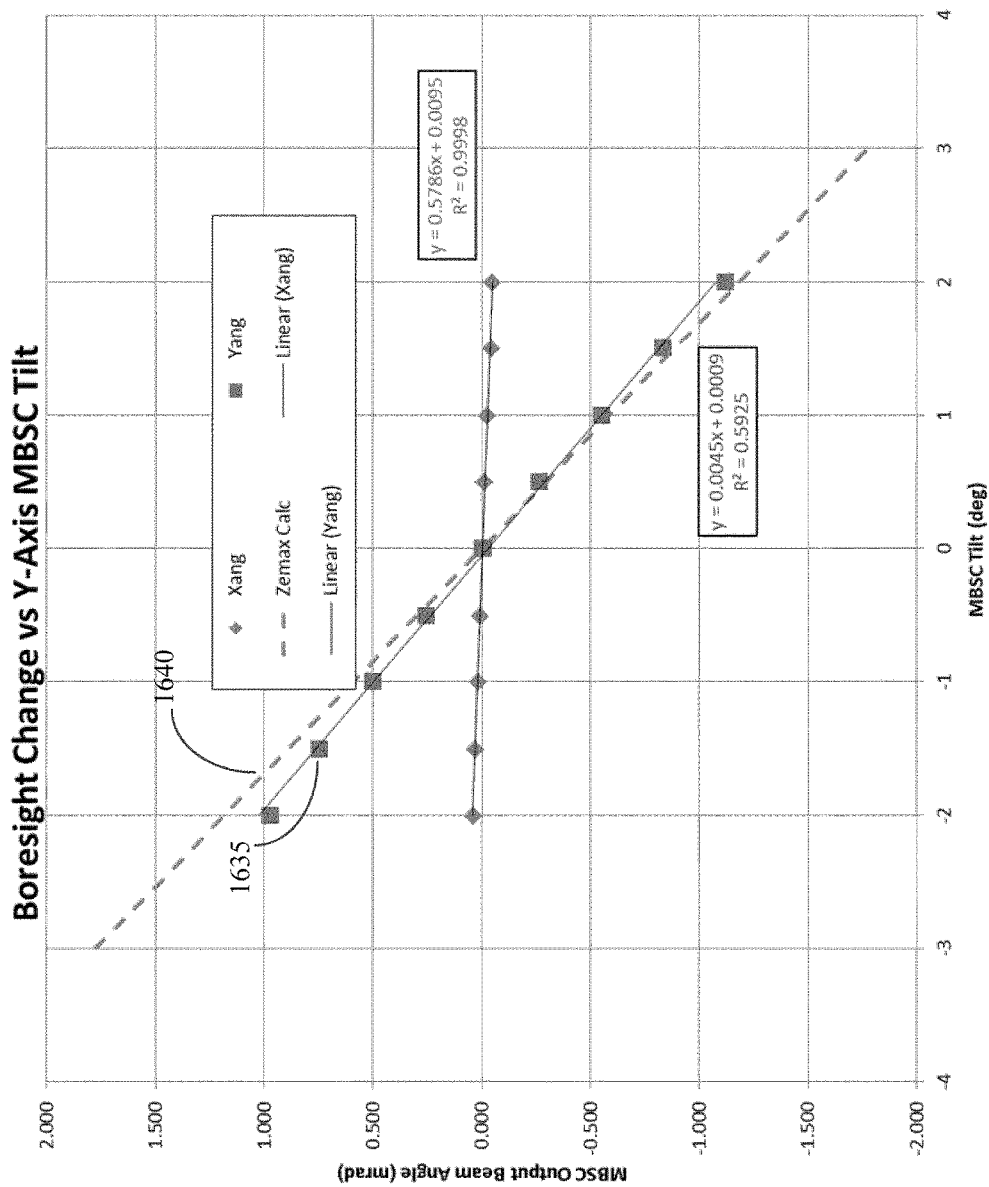
FIG. 16(d-4)

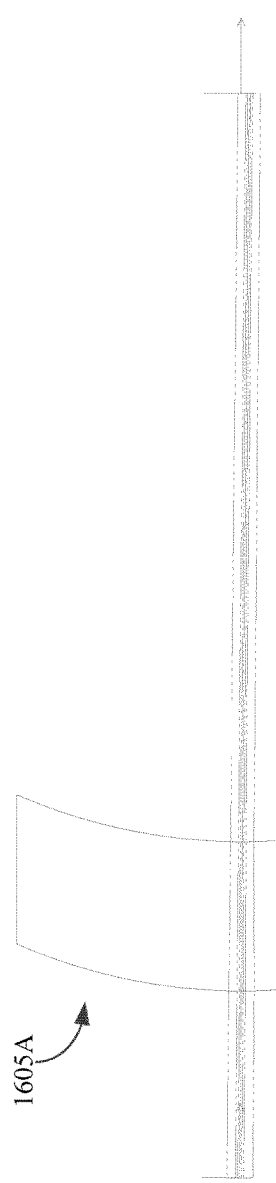
FIG. 16(e-1)
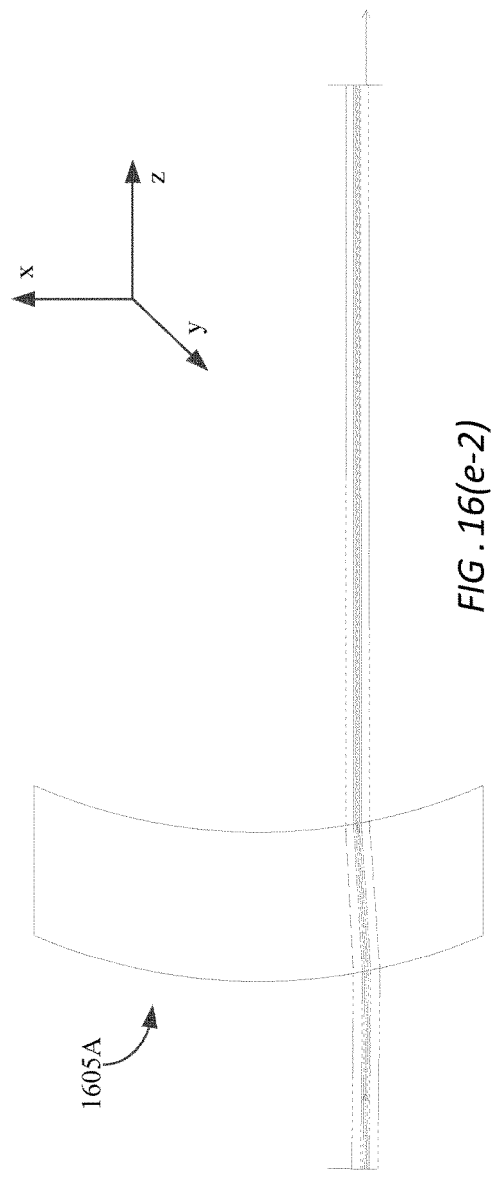
FIG. 16(e-2)

LASER SYSTEMS AND OPTICAL DEVICES FOR MANIPULATING LASER BEAMS

PRIORITY CLAIM

This application is a divisional of U.S. patent application Ser. No. 15/067,818, filed Mar. 11, 2016, which claims priority to U.S. Provisional Patent Application No. 62/133,241 entitled "Laser Systems and Optical Devices for Manipulating Laser Beams" filed Mar. 13, 2015 and also claims priority to U.S. Provisional Patent Application No. 62/135,137 entitled "Laser Systems and Optical Devices for Manipulating Laser Beams" filed Mar. 18, 2015. Each of the above-identified applications is incorporated herein by reference in its entirety.

CROSS-REFERENCE TO RELATED APPLICATIONS

This application is related to a continuation-in-part, U.S. patent application Ser. No. 12/940,004, filed Nov. 4, 2010, titled "Compact, Thermally Stable Multi-Laser Engine", which is a continuation-in-part of U.S. patent application Ser. No. 12/418,537, filed Apr. 3, 2009, titled "Compact, Thermally Stable Multi-Laser Engine", which claims the benefit of U.S. Provisional Application No. 61/042,652, filed Apr. 4, 2008, all of which are incorporated herein by reference in their entireties. This application is also related to another continuation-in-part, U.S. patent application Ser. No. 12/418,494, filed Apr. 3, 2009 and titled "Compact, Thermally Stable Fiber-Optic Array Mountable to Flow Cell", which claims the benefit of U.S. Provisional Application No. 61/042,640, filed Apr. 4, 2008, both of which are incorporated herein by reference in their entireties. This application is also related to U.S. patent application Ser. No. 14/103,709, filed Dec. 11, 2013, titled "Optical Systems", which claims the benefit of U.S. Provisional Application No. 61/736,500, filed Dec. 12, 2012, both of which are incorporated herein by reference in their entireties. Accordingly, each of the above referenced applications is incorporated herein by reference in their entireties.

BACKGROUND

Field

Part I

This disclosure generally relates to optical (e.g., fluorescent, spectroscopic) analysis of biological samples through flow cells and/or optical fibers connected to confocal microscopes or "lab-on-a-chip" devices, and to, for example, compact, thermally stable multi-laser systems configured to couple to flow cells, optical fibers, or other target objects and to provide illumination thereto.

Part II

This disclosure relates generally to optical systems for directing light to a sample contained in a flow cell, and more particularly to a compact, thermally stable, optical fiber array attachable to a flow cell for directing laser light to the flow cell for optical measurements such as laser-induced fluorescence.

Description of Related Art

Part I

Optical analysis of flow cells, such as laser-induced fluorescence, involves illuminating biological samples with laser light in order to test samples which may, for example, be tagged with fluorescent dyes. Fluorescent dyes absorb light at certain wavelengths and in turn emit their fluorescence energy at a different wavelength. This emission can be detected to ascertain properties of the fluid in the flow cell. Existing systems for fluorescent analysis of flow cells, however, suffer from various drawbacks, such as measurement error.

Part II

Optical analysis of flow cells, such as laser-induced fluorescence, involves illuminating biological samples with laser light in order to test samples which may, for example, be tagged with fluorescent dyes. Fluorescent dyes absorb light at certain wavelengths and in turn emit their fluorescence energy at a different wavelength. This emission can be detected to ascertain properties of the fluid in the flow cell. Existing systems for fluorescent analysis of flow cells, however, suffer from various drawbacks, such as measurement error.

SUMMARY

Part I

Embodiments described herein have several features, no single one of which is solely responsible for their desirable attributes. Without limiting the scope of the invention as expressed by the claims, some of the advantageous features will now be discussed briefly.

Various embodiments described herein provide the ability to perform optical measurements on flow cells while addressing some of the drawbacks encountered with conventional approaches, such as laser beam alignment to the flow cell that is sensitive to the ambient temperature resulting in signal power fluctuations.

A wide range of embodiments are disclosed. Some embodiments, for example, comprise a compact, thermally stable multi-laser system. The multi-laser system comprises a plurality of lasers. The plurality of lasers outputs a plurality of respective laser beams. The system further comprises a beam positioning system. The beam positioning system is configured to position the plurality of laser beams closer together. The multi-laser system further comprises beam focusing optics. The beam focusing optics are configured to focus the plurality of laser beams. The multi-laser system further comprises a thermally stable enclosure. The thermally stable enclosure encloses the plurality of lasers, the beam positioning system and the beam focusing optics. The thermally stable enclosure is configured to thermally and mechanically couple to a flow cell. The thermally stable enclosure substantially comprises a material with high thermal conductivity of at least 5 W/(m K). The thermally stable enclosure has a volume of no more than 36 cubic inches. The system further comprises a temperature controller. The temperature controller is configured to control the temperature of the thermally stable enclosure and to maintain the alignment of the focused laser beams to the flow cell over a range of ambient temperatures.

In some embodiments, a compact, thermally stable multi-laser system comprises a plurality of lasers. The plurality of lasers outputs a plurality of respective laser beams. The system further comprises a beam positioning system. The beam positioning system is configured to reposition the plurality of laser beams. The system further comprises a thermally stable enclosure. The thermally stable enclosure encloses the plurality of lasers and the beam positioning system. The thermally stable enclosure substantially comprises a material with high thermal conductivity of at least 5 W/(m K). The thermally stable enclosure is configured to control the temperature of the thermally stable enclosure and configured to maintain the alignment of the focused laser beams to a target object over a range of ambient temperatures. The system further comprises a temperature controller. The temperature controller is configured to control the temperature of the thermally stable enclosure. Other embodiments are also disclosed.

Part II

Embodiments described herein have several features, no single one of which is solely responsible for their desirable attributes. Without limiting the scope of the invention as expressed by the claims, some of the advantageous features will now be discussed briefly.

Various embodiments described herein provide the ability to perform optical measurements on flow cells while addressing some of the drawbacks encountered with conventional approaches, such as temperature instability and the resultant pointing errors and signal power fluctuations. A wide range of embodiments, however, are disclosed.

Various embodiments disclosed herein, for example, comprise a laser system for directing light for optical measurements, such as laser-induced fluorescence. The laser system can include a thermally conductive housing defining an interior chamber, and a thermoelectric controller thermally coupled to the housing. The laser system can include a plurality of optical input ports, and the optical input ports can be configured to engage a plurality of input optical fibers and receive light from the input optical fibers. The laser system can include a plurality of optical fibers contained within the interior chamber, and the optical fibers can be configured to receive the light from the optical input ports and output the light into the internal chamber. The laser system can include one or more optical elements configured to receive the light output by the optical fibers and output a plurality of beams of light. The laser system can include a flow cell connector configured to attach a flow cell to the housing, and the flow cell connector can be configured to position the flow cell to intersect the beams of light.

The thermoelectric controller can be configured to maintain the interior chamber at a substantially constant temperature.

The plurality of beams of light produced by the one or more optical elements can comprise a plurality of substantially elliptical beams of light. The one or more optical elements can comprise a plurality of anamorphic microlenses. The laser system can include one or more output windows, and the one or more output windows can be configured to transmit the beams of light out of the internal chamber.

The flow cell connector can be configured to attach the flow cell to the outside of the housing. The housing can be hermetically sealed.

The plurality of input ports can be configured to removably engage the plurality of input optical fibers. The plurality of input ports can comprise a plurality of FC connectors. The plurality of input ports can comprise a plurality of angle-polished connections.

The plurality of optical fibers can comprise a plurality of input ends and a plurality of output ends, with the input ends being distributed across a first distance and the output ends being distributed across a second distance, wherein the first distance is greater than the second distance. Each output end can comprise a center, and the centers can be spaced about 110 to 140 micrometers apart. The one or more optical elements can be configured to produce the beams of light spaced about 110 to 140 micrometers apart. The centers can be spaced about 125 micrometers apart, and the one or more optical elements can be configured to produce the beams of light spaced about 125 micrometers apart. The plurality of optical fibers can be polarization-maintaining optical fibers.

The laser system of can include a plurality of input optical fibers coupled to the optical input ports, and a plurality of laser light sources coupled to the input optical fibers.

The laser system can include a flow cell attached to the housing via the flow cell connector, and the flow cell can be configured to direct a sample fluid into the beams of light. The flow cell connector can comprise thermally conducting material, and the flow cell connector can be thermally coupled to the thermoelectric controller, and the thermoelectric controller can be configured to maintain the flow cell at a substantially constant temperature.

The one or more optical elements can be formed in the housing, the one or more optical elements configured to transmit the light out of the internal chamber, and the flow cell connector can be configured to attach the flow cell to the outside of the housing.

The flow cell connector can be configured to attach the flow cell to the housing with the flow cell passing through the interior chamber, and the flow cell connector can comprise at least one seal configured to form a seal around the flow cell.

Various embodiments disclosed herein comprise a laser system for directing light for optical measurements. The laser system can include a thermally conductive housing defining an interior chamber, and a thermoelectric controller thermally coupled to the housing. The laser system can include a plurality of optical input ports, and the optical input ports can be configured to engage a plurality of input optical fibers and receive light from the input optical fibers. The laser system can include a plurality of waveguides contained within the interior chamber, and the waveguides can be configured to receive the light from the optical input ports and output the light into the internal chamber. The laser system can include one or more optical elements configured to receive the light output by the waveguides and output a plurality of beams of light. The laser system can include a flow cell connector configured to attach a flow cell to the housing, and the flow cell connector can be configured to position the flow cell to intersect the beams of light.

Various embodiments disclosed herein comprise a laser system for directing light for optical measurements. The laser system can include a plurality of optical fibers for receiving light from a plurality of lasers, and the optical fibers can have a plurality of output ends, and each output end can include a center. The laser system can include an optical fiber mount configured to orient the plurality of optical fibers with the centers of said output ends spaced about 110 to 140 microns apart. The laser system can include a flow cell connector configured to position a flow cell forward the output ends. The optical fiber mount can be configured to orient the plurality of optical fibers with the centers of the output ends spaced about 125 microns apart.

Various embodiments disclosed herein comprise a laser system for directing light for optical measurements. The laser system can include a flow cell configured to provide a sample fluid for measurement, and a plurality of optical fibers for receiving light from a plurality of lasers. The optical fibers can have a plurality of output ends. The laser system can include an optical fiber mount configured to orient the plurality of optical fibers with the output ends positioned to emit light toward said flow cell.

Various embodiments disclosed herein comprise a multi-laser system. The multi-laser system can include a laser outputting a laser beam; and a beam adjusting system configured to adjust an angular position of the laser beam and direct the adjusted laser beam toward a target object. The beam adjusting system comprises at least one meniscus shaped optical element having a first surface and a second opposite surface, where said meniscus shaped optical element is adjustable to adjust the angular position of the laser beam.

Various embodiments disclosed herein comprise an optic system. The optic system includes a first lens for receiving a laser beam having a Gaussian beam profile, said first lens configured to alter the beam size of the laser beam in at least one direction; a Powell lens configured to convert said laser beam that has a Gaussian beam profile into a laser beam having a flat top intensity distribution and an elongated cross-section orthogonal to propagation of the beam, said elongated cross-section having a length in a first direction that is longer than in a second orthogonal direction; a second lens configured to collimate said laser beam at least in one direction; a translation stage configured to receive a control signal that drives movement of said translation stage, where said Powell lens is coupled to the translation stage such that the Powell lens can be translated with respect to said first and second lens in response to said control signal.

Various embodiments disclosed herein comprise an optic system for adjusting a translation stage with a coupled Powell lens. The optic system can include a translation stage configured to receive a voltage; a beam focusing optics unit comprising a first lens, a Powell lens, coupled to the translation stage, and a second lens; and a control system including an image processing unit. The control system can be configured to adjust the translation stage by at least generating an image processing result representing an optical power distribution of a beam based on feedback corresponding to an optical image of a beam cross-section; determining, based on the image processing result representing the power distribution of the beam, to move a position of the translation stage; and sending, to the translation stage with the coupled Powell lens, one or more signals to adjust the position of the translation stage in at least one coordinate plane. The feedback may also be a beam spot, an optical image of a cross-sectional shape, or a cross-section of a laser beam.

BRIEF DESCRIPTION OF THE DRAWINGS

The following drawings and the associated descriptions are provided to illustrate embodiments of the present disclosure and do not limit the scope of the claims.

FIG. 16(*b*) illustrates an implementation of a meniscus shaped optical element 1605A including a first curved surface 1607 configured to receive the incident laser beam and a second curved surface 1609 opposite the first curved surface 1607 configured to output the laser beam.

FIG. 16(*c*-1) depicts a laser beam with 0 degree boresight error that is incident on an implementation of an optical element 1605A.

FIG. 16(*c*-2) depicts a laser beam with about 1 degree boresight error that is incident on an implementation of an optical element 1605A.

FIG. 16(*c*-3) depicts a tilted configuration of the optical element to correct boresight error.

FIG. 16(*d*-1) illustrates the variation in the boresight angle change expressed in radians (rad) versus the change in the angle of incidence (AoI) which corresponds to the relative angle of incidence of the laser beam with respect to the meniscus optical element expressed in degrees for an implementation of a cylindrical meniscus shaped optical element.

FIG. 16(*d*-2) illustrates the variation in the boresight angle change expressed in milliradians (mrad) versus the change in the angle of incidence (AoI) which corresponds to the relative angle of incidence of the laser beam with respect to the meniscus optical element expressed in degrees measured for an implementation of a cylindrical meniscus shaped optical element.

FIG. 16(*d*-3) illustrates the measured variation in the boresight angle of an output laser beam expressed in milliradians (mrad) as a function of tilt about the x-axis of an implementation of a spherical meniscus shaped optical element depicted by curve 1625.

FIG. 16(*d*-4) illustrates the measured variation in the boresight angle of an output laser beam expressed in milliradians (mrad) as a function of tilt about the y-axis of an implementation of a spherical meniscus shaped optical element depicted by curve 1635.

FIG. 16(*e*-1) depicts a laser beam with about 0.5 degree boresight error that is incident on an implementation of an optical element 1605A.

FIG. 16(*e*-2) illustrates an implementation of a translated configuration of the optical element 1605A.

DETAILED DESCRIPTION

Part I

This application incorporates herein by reference in their entirety U.S. Patent Publication No. 2011/0134949 and corresponding U.S. patent application Ser. No. 12/940,004, filed Nov. 4, 2010, titled "Compact, Thermally Stable Multi-Laser Engine", U.S. Patent Publication No. 2009/0274176 and corresponding U.S. patent application Ser. No. 12/418,537, filed Apr. 3, 2009, titled "Compact, Thermally Stable Multi-Laser Engine", as well as U.S. Provisional Application No. 61/042,652, filed Apr. 4, 2008.

Although certain preferred embodiments and examples are disclosed herein, inventive subject matter extends beyond the specifically disclosed embodiments to other alternative embodiments and/or uses of the inventions, and to modifications and equivalents thereof. Thus, the scope of the inventions herein disclosed is not limited by any of the particular embodiments described below. For example, in any method or process disclosed herein, the acts or operations of the method or process may be performed in any suitable sequence and are not necessarily limited to any particular disclosed sequence.

For purposes of contrasting various embodiments with the prior art, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
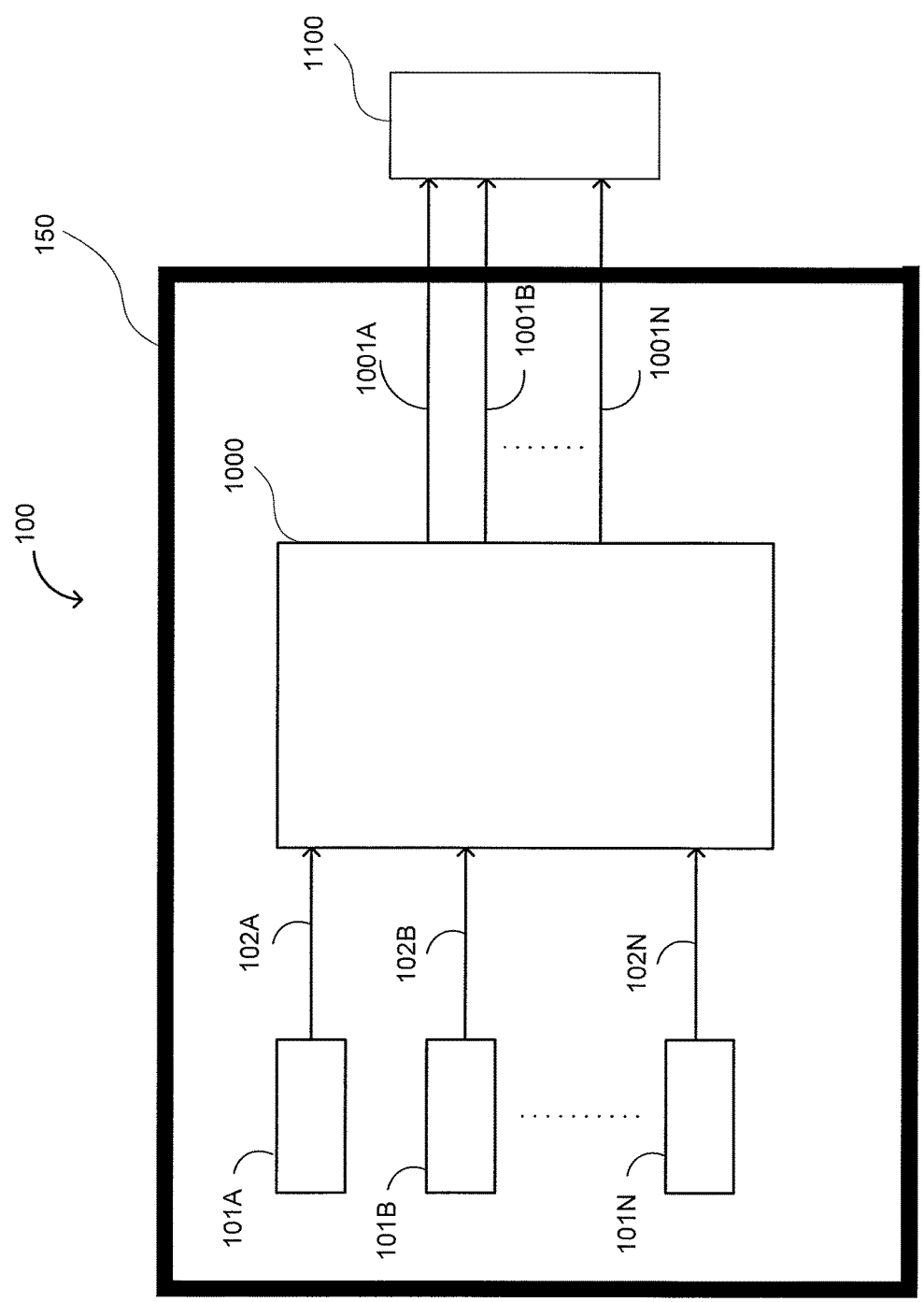
FIG. 1 depicts an example embodiment of a multi-laser system.

FIG. 1 depicts an example embodiment of a multi-laser system. The multi-laser system 100 depicted in FIG. 1 comprises a thermally stable, temperature controlled enclosure 150 configured to mechanically and/or thermally couple to a target object 1100. The enclosure 150 helps to isolate the laser and optics within the enclosure 150 from the ambient environment, which may have varying temperature. By maintaining the temperature within the enclosure within a relatively small range, thermally induced laser wavelength and intensity fluctuations as well as pointing instabilities of the laser beams can be reduced or minimized. In some embodiments, the target object may comprise a flow cell, a flow cell mount, a light pipe, a waveguide, an optical fiber, or a lab on a chip. In some embodiments, the target object may comprise a mounting mechanism, mounting system (e.g., mounting alignment system), etc. for a flow cell, a flow cell mount, a light pipe, a waveguide, an optical fiber, and/or a lab on a chip.

In some embodiments, the temperature across the enclosure may be stable over time and with changes in the ambient temperature. The constant temperature over time may help with long term system performance. For example if the enclosure temperature were to change with time, then the system performance would also potentially degrade with time. This could eventually result in servicing the system, e.g., to realign the system.

The thermally stable enclosure 150 comprises a material with high thermal conductivity. In some embodiments, a material with thermal conductivity of at least about 5 W/(m K), (e.g., between about 5 W/(m K) and about 2000 W/(m K)) is used. In some embodiments, a material with thermal conductivity at least about 50 W/(m K) (e.g., between about 50 W/(m K) and about 2000 W/(m K)) is used. In other embodiments, a material with thermal conductivity of about 375 W/(m K) or greater is used. In other embodiments, a material with thermal conductivity of at least about 380 W/(m K) is used. In some embodiments, a material with thermal conductivity between about 125 W/(m K) and about 425 W/(m K)) is used. In some embodiments, a material with thermal conductivity between about 375 W/(m K) and about 425 W/(m K)) is used. In some embodiments, a material with thermal conductivity between about 125 W/(m K) and about 250 W/(m K)) is used. In some embodiments, a material with thermal conductivity between about 200 W/(m K) and about 250 W/(m K)) is used. In some embodiments, the material has a heat capacity corresponding o the heat capacity of the materials described herein. The use of such thermally conductive material helps ensure a relatively reduced temperature variation within the enclosure 150, even when the ambient temperature outside of the enclosure varies relatively widely.

As described more fully below, a temperature controller in thermal contact with the enclosure adjusts the temperature of the enclosure in response to variations in ambient conditions. A highly thermally conductive enclosure enables the temperature controller to more quickly and effectively maintain the enclosure and system temperature without temperature gradients in response to such variations in ambient conditions. A variety of thermally conductive materials can be used (e.g., copper, aluminum, copper tungsten, ceramics, epoxy, etc.). In some embodiments, a material with a thermal conductivity of at least 5 W/(m K) may be used. In other embodiments, a material with a thermal conductivity of less than 5 W/(m K) may be used. The thermally conductive material can be used to form the entire enclosure, or merely a portion thereof. In certain embodiments, the enclosure substantially comprises highly thermally conductive material. For example, highly thermally conductive material can be used to form the top, the bottom, or any number of the sides of the enclosure 150, or any combination thereof. In some embodiments, a majority of the enclosure 150 is made of the substantially thermally conductive material. In some embodiments, only a relatively small portion of the enclosure 150 is made of the thermally conductive material. In some embodiments, a substantial portion of the enclosure 150 is made of the substantially thermally conductive material. In some embodiments, multiple substantially thermally conductive materials can be used, with some areas of the enclosure 150 being more thermally conductive than others.

The multi-laser system 100 includes a plurality of lasers 101A-101N, enclosed within the thermally stable enclosure 150. The plurality of lasers 101A-101N may comprise diode lasers, solid-state lasers, frequency-doubled lasers, and/or other types of lasers. The plurality of lasers 101A-101N output a plurality of respective laser beams 102A-102N. Each of the laser beams 102A-102N may have a wavelength different from the other laser beams.

As shown in FIG. 1, the multi-laser system 100 further includes a beam positioning system 1000. To achieve a desired spatial arrangement of the laser beams 102A-102N, the inherent laser beam boresight and centration errors present in lasers 101A-101N, as well angular and lateral positioning errors present in the multi-laser system's opto-mechanical components can be compensated for. In some embodiments, the beam positioning/combining system 1000 may include mechanical and/or opto-mechanical provisions to perform such compensation.

Mechanical provisions to the laser mounting may be used to adjust the angular and/or lateral position of the lasers so that the boresight and centration errors of the lasers 101A-101N as well as the angular and lateral positioning errors of the opto-mechanical components are compensated for. The aligned laser beams may then be positioned or combined by the beam positioning/combining system 1000 into a desired spatial arrangement that a specific application requires.

Opto-mechanical provisions to the beam positioning/alignment system may be used to allow for angular and lateral position adjustment of the laser beams. This adjustment capability may help compensate for the lasers' boresight and centration errors as well as the angular and lateral positioning errors of the opto-mechanical components to achieve a desired spatial arrangement of the laser beams.

In embodiments in which the system is used perform testing of biological samples, flow cells are illuminated with laser beams. Fluorescent dyes absorb light at certain wavelengths and in turn emit their fluorescence energy at a different wavelength. This emission can be detected to ascertain properties of the fluid in the flow cell. Temperature variations may cause the wavelength and/or the intensity of light output by the lasers to vary. Such variations in the laser beams directed into the flow cell may cause fluctuations in output fluorescent signals, which may introduce inaccuracy in the optical measurements. Temperature variations and/or temperature gradients also may cause movement of the optical elements (e.g., due to thermal expansion) and resultant shifting of the laser beams. These pointing errors may cause the laser beams to deviate from the flow cell, such that the signal changes, or is altogether lost, again introducing inaccuracy in the test results.

Temperature variations can result from ambient temperature fluctuations. Accordingly, reducing the temperature variation of and the presence of temperature gradients within the laser beam system can improve the accuracy and usability of the test results.

Figure 2:
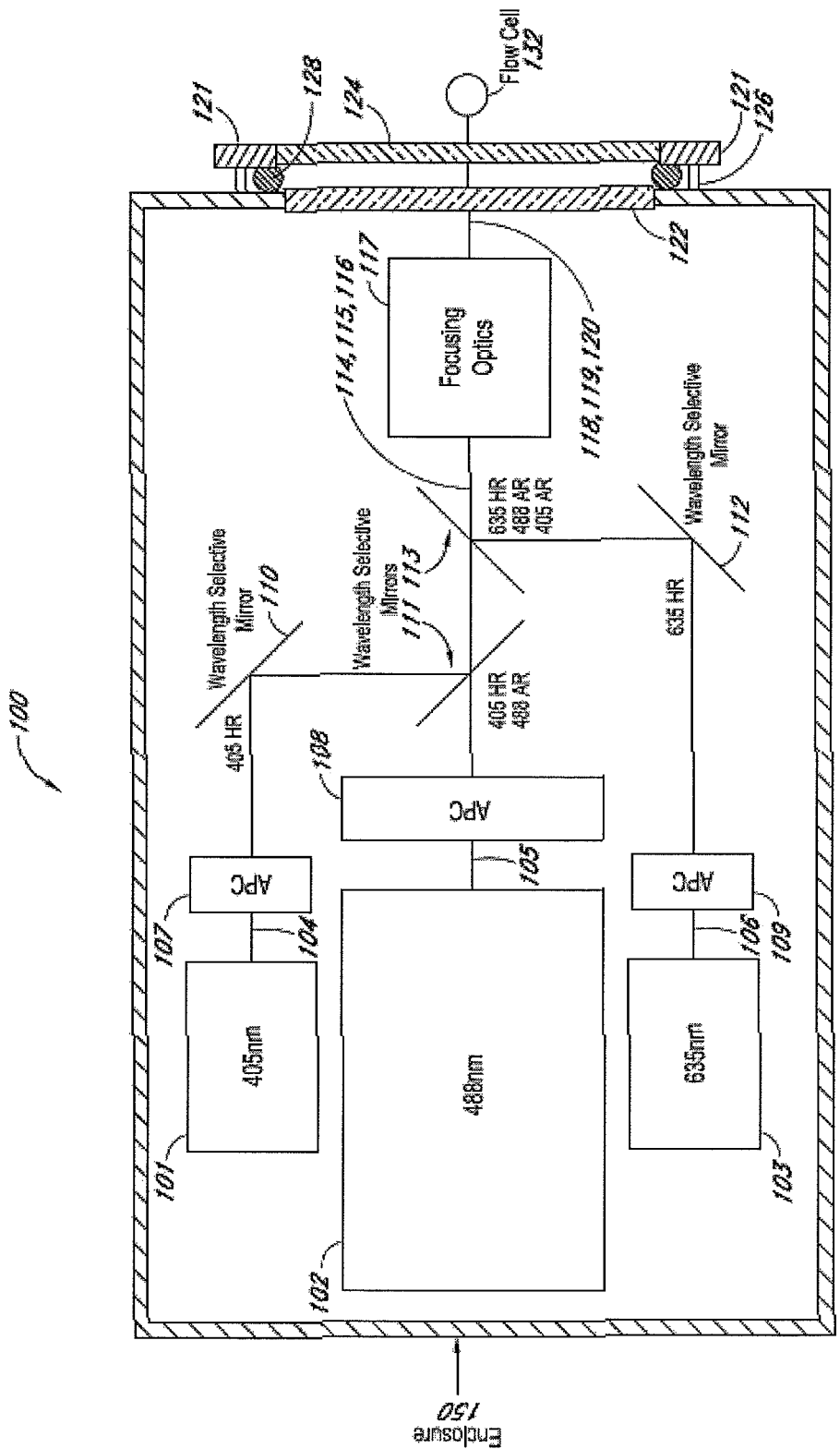
FIG. 2 depicts another example embodiment of a multi-laser system.

Various embodiments described herein may address one or more of these problems. FIG. 2 is a top view of another example embodiment of the multi-laser system 100. The multi-laser system 100 depicted in FIG. 2 comprises a thermally stable enclosure 150 configured to mechanically and/or thermally couple to a flow cell 132. The thermally stable enclosure 150 helps to isolate the laser and optics within the enclosure 150 from the ambient environment, which may have varying temperature. In some embodiments, the enclosure 150 can achieve thermal stability through the use of a temperature controller, as discussed in relation to FIG. 3 below. In various embodiments, the enclosure 150 helps reduce variations in the temperature of the various components of the multi-laser system 100. By maintaining the temperature within the enclosure within a relatively small range, thermally induced laser wavelength and intensity fluctuations as well as pointing instabilities of the laser beams can be reduced or minimized and alignment of the laser beams to a target object may be maintained over a range of ambient temperatures (e.g., between about 10° C. and about 55° C.). Accordingly, the use of a thermally stable enclosure 150 may help achieve more accurate test results.

Some materials expand and contract when heated or cooled. Changes in the enclosure temperature or temperature variations across the enclosure can result in a change in the relative positions of lasers, mirrors, lenses, and the target object (e.g., flow cell). Some lasers exhibit beam pointing that is temperature dependent. This may be due in part to the fact that different materials are used in the construction of the laser (e.g., metals, glass, adhesives, etc). The different materials may have different thermal expansion coefficients, which may cause beam deviations when the laser system's temperature changes. Some mirror and lens systems also show some temperature dependence for the same reason.

The multi-laser system 100 depicted in FIG. 2 includes a plurality of lasers 101, 102, 103 enclosed within the thermally stable enclosure 150. Although FIG. 2 includes three lasers, a different number of lasers can be used. The multi-laser system 100 shown in FIG. 2 includes a 405 nm laser, a 488 nm laser and a 635 nm laser, but other wavelengths can also be used (e.g., lasers having wavelengths of 375 nm, 440 nm, 515 nm, 561 nm, 594 nm, 640 nm, etc.).

The plurality of lasers 101, 102, 103 output a plurality of respective laser beams 104, 105, 106. Laser beam 104 has a first wavelength, laser beam 105 has a second wavelength, and laser beam 106 has a third wavelength. The first, second, and third wavelengths are different from one another. In FIG. 2, these wavelengths are 405 nm, 488 nm and 635 nm, respectively, but other wavelengths can also be used (e.g., 375 nm, 440 nm, 515 nm, 561 nm, 594 nm, 640 nm, etc.).

As shown in the example embodiment of FIG. 2, the multi-laser system 100 further includes a plurality of automatic power control (APC) modules 107, 108, 109. In some embodiments, the APC modules 107, 108, 109 may each comprise a beamsplitter (not shown) and a photodetector (not shown) configured to sample light from the laser beams 104, 105, 106, respectively, and to feed back the signal from the detector in communication with a laser controller (not shown) to adjust the output power of lasers 101, 102, 103, respectively. Other approaches may also be possible.

Referring still to FIG. 2, the beam positioning system comprises a plurality of wavelength selective mirrors 110, 111, 112, 113. In various embodiments, some of the the wavelength selective 110, 111, 112, 113 mirrors have significantly different reflection or transmission properties at different wavelengths. Accordingly, the wavelength selective mirrors 110, 111, 112, 113 can separate or combine laser beams with different wavelengths. In some embodiments, the mirrors 110, 112 may be broadband, for example because light is not transmitted through the mirrors 110, 112. Through the use of suitable optical coatings, wavelength selective mirrors exhibit high reflection over some range of wavelengths and high transmission over another range of wavelengths. The wavelength selective mirrors are appropriate for the wavelengths of the laser sources. For example, various of the wavelength selective mirrors will selectively reflect (or transmit) light propagating from one laser at a first wavelength and not light propagating from another laser at a second wavelength. The example embodiment of FIG. 2 depicts four wavelength selective mirrors 110, 111, 112, 113. In other embodiments, a different number of wavelength selective mirrors may be used (e.g., see FIG. 2A). In some embodiments, the wavelength selective mirrors may comprise dichroic and trichroic mirrors. Dichroic mirrors can separate or combine lasers with two different wavelengths. In various embodiments dichroic mirrors may allow at least one wavelength to substantially or totally pass through and may substantially or totally reflect at least one wavelength. Trichroic mirrors can separate or combine lasers with three different wavelengths. Trichroic mirrors may be optimized for three wavelengths, they may have three peaks or one broad peak that covers multiple wavelengths. In other embodiments, the wavelength selective mirrors may comprise mirrors with selectivity for a different number of wavelengths. Alternatively, substantially non-wavelength selective mirrors that do not selectively reflect (or transmit) light of one laser and not light of another laser may be inserted in the path of the beam to redirect and/or alter the beam path or the beam. Other optical elements can be inserted into the optical path.

The wavelength selective mirrors 110, 111, 112, 113 are configured with highly reflective and anti-reflective coatings in accordance with the wavelengths of the plurality of laser beams 104, 105, 106. As shown in FIG. 2, wavelength selective mirror 110 is configured to be highly reflective of the wavelength of the laser beam 104 (e.g., 405 nm, all wavelengths); wavelength selective mirror 111 is configured to be highly reflective of the wavelength of the laser beam 104 (e.g., 405 nm) and anti-reflective of the wavelength of the laser beam 105 (e.g., 488 nm); wavelength selective mirror 112 is configured to be highly reflective of the wavelength of the laser beam 106 (e.g., 635 nm, all wavelengths), and wavelength selective mirror 113 is configured to be highly reflective of the wavelength of the laser beam 106 (e.g., 635 nm), and anti-reflective of the wavelengths of the laser beams 104 (e.g., 405 nm) and 105 (e.g., 488 nm). In other embodiments, the wavelength selective mirrors can be configured to be highly reflective of some wavelengths and anti-reflective of some other wavelengths in order to separate or combine the wavelengths as necessary.

In some embodiments, this plurality of wavelength selective mirrors 110, 111, 112, 113 may be supported by a plurality of respective flexure mounts (not shown). Flexure mounts are less likely to move with external vibrations and thus are less likely to require adjustment. Flexure mounts reduce impact on the optics from shocks such as may be introduced by shipping of the system. Additionally, flexure mounts typically exhibit less hysteresis than rolling or sliding contacts. Flexure mounts are typically fabricated from materials which make them relatively less sensitive to temperature variations. Flexure mounts may also be smaller than conventional spring loaded mounts. In some embodiments, the flexure mounts may comprise a nickel-iron alloy material for example. Other materials may also be used. In other embodiments, the plurality of wavelength selective mirrors 110, 111, 112, 113 may be supported by a plurality of respective spring-loaded mirror mounts (not shown). In other embodiments, the plurality of wavelength selective mirrors 110, 111, 112, 113 may be supported by a plurality of respective glue-block mounts (not shown).

In the multi-laser system 100 shown in FIG. 2, three optical paths are depicted. A first optical path at a wavelength of 405 nm originates at laser 101, passes through the APC 107, where a portion of the signal is picked off (e.g., by a beam splitter), is then highly reflected at wavelength selective mirrors 110 and 111 and transmitted through wavelength selective mirror 113, and then arrives at the focusing optics 117. A second optical path at a wavelength of 488 nm originates at laser 102, passes through the APC 108, where a portion of the signal is picked off (e.g., by a beam splitter), is then transmitted through wavelength selective mirrors 111 and 113, and then arrives at the focusing optics 117. A third optical path at a wavelength of 635 nm originates at laser 103, passes through the APC 109, where a portion of the signal is picked off (e.g., by a beam splitter), is then reflected at wavelength selective mirrors 112 and 113, and then arrives at the focusing optics 117. Propagating along these paths, laser beams 104, 105, 106, which may have originally been far from one another, are repositioned to be closer together as beams 114, 115, 116 and, after the focusing optics, beams 118, 119, 120, respectively. In some embodiments, the beams 118, 119, 120 are parallel to one another. In other embodiments, the beams 118, 119, 120 are not parallel to one another. Other mirrors and optical components (e.g., lenses, prisms, polarization rotators, waveplates, etc.) can be included to alter the laser beams and/or optical paths.

Still referring to FIG. 2, the multi-laser system 100 further includes optional beam focusing optics 117 to provide size reduction and/or shaping to the output laser beams 118, 119, 120. For example, the focusing optics 117 may focus a laser beam down to a smaller spot. Additionally, the focusing optics 117 may change the shape of the laser beams. In some embodiments, for example, the laser beams 118, 119, 120 can have a generally Gaussian profile, so that when illuminating a flow cell, the intensity of the light illuminating the center of the flow cell is significantly greater than the intensity of the light illuminating the peripheral edges of the flow cell. Accordingly, the beams of light 118, 119, 120 can be elongated (e.g., elliptical) beams, so that the relatively high intensity center regions of the light beams extend across the entire width of the flow cell, while the relatively low intensity outer regions of the light beams do not strike the flow cell. By using an elongated (e.g., elliptical) beam of light, a more uniform distribution of light across the width of the flow cell or other target output can be achieved while illuminating a relatively small longitudinal area along the length of the flow cell and maintaining substantially uniform high light intensity.

In some embodiments, the beams 114, 115, 116 enter the beam focusing optics 117 and can have circular cross-sections with a Gaussian fall-off. In some embodiments, the beam focusing optics 117 may include an anamorphic lens system which may produce non-rotationally symmetric or elongated beam such as a beam with elliptical cross-section and spot size. In other embodiments, the beam focusing optics 117 may include cylindrical lenses. In some embodiments, the beam focusing optics 117 may include spherical lenses. In some embodiment, the beam focusing optics 117 may include powell lenses (Gaussian to flat-top transformers). In some embodiments, the beam focusing optics 117 may include aspherical lenses. The focusing optics may be achromatic with reduced chromatic aberration thereby reducing positioning error which may otherwise result from different color laser beams. Accordingly, achromatic anamorphic optics, achromatic elliptical optics, achromatic spherical optics and achromatic aspherical optics, may be used. In some embodiments, lenses can be an anamorphic microlens array. In some embodiments, refractive and/or diffractive optics can be used to produce the elongated beams of light 118, 119, 120. Other types of optics are possible.

In cases where the laser comprises a semiconductor laser, the laser beam output may already be elliptical-shaped, and optics to convert the elliptical beam into a circular beam can be substantially excluded. In such cases, there would be no need to include anamorphic focusing optics to make the elliptical-shaped beam spherical (e.g., rotationally symmetric). Spherical or rotationally symmetric optics may be employed without anamorphic elements.

The output laser beams 118, 119 and 120 depicted in FIG. 2 may have respective spot sizes of between about 55 µm and about 110 µm in one direction and between about 5 µm and about 15 µm in another direction (e.g., perpendicular to the one direction). In other embodiments, the laser beams may have respective spot sizes of between about 70 µm and about 110 µm in one direction and between about 5 µm and about 15 µm in another direction (e.g., perpendicular to the one direction). In other embodiments, the laser beams may have respective spot sizes of between about 50 µm and about 150 µm in one direction and between about 5 µm and about 20 µm in another direction (e.g., perpendicular to the one direction). In other embodiments, the laser beams may have spot sizes of between about 55 µm and about 100 µm in one direction and between about 5 µm and about 15 µm in another direction (e.g., perpendicular to the one direction). In other embodiments, the laser beams may have spot sizes of between about 70 µm and about 100 µm in one direction and between about 5 µm and about 15 µm in another direction (e.g., perpendicular to the one direction). In other embodiments, the laser beams may have respective spot sizes of between about 50 µm and about 150 µm in one direction and between about 5 µm and about 20 µm in another direction (e.g., perpendicular to the one direction). In some embodiments, the output laser beams 118, 119, 120 may have respective spot sizes of about 80 µm in one direction and about 10 µm in another direction (e.g., perpendicular to the one direction). In other embodiments, the output laser beams 118, 119, 120 may have respective spot sizes of about 100 µm in one direction and about 10 µm in another direction (e.g., perpendicular to the one direction). The directions may correspond to major and minor axes of an ellipse for a beam with an elliptical cross-section and spot shape. Other sizes and shapes are possible for the light beams.

Still referring to FIG. 2, the multi-laser system 100 includes coupling to a flow cell 132. The multi-laser system 100 can include an output window 121 that allows the beams of light 118, 119, 120 to exit the enclosure 150. The output window 121 can be made from, for example, fused silica, glass, acrylic, or a variety of other transparent materials (e.g., plastic). In some embodiments, the enclosure 150 includes an aperture 122 in a wall thereof and the output window 121 comprises a transparent window pane 124 positioned over the aperture 122. The window pane 124 can be made from, for example, fused silica, glass, acrylic, or a variety of other transparent materials (e.g., plastic). The aperture 122 and window pane 124 can assume a variety of shapes, but in some embodiments they are rectangular, circular, or elliptical. The window 121 can be attached to the enclosure 150 by a plurality of fasteners such as bolts 126. In FIG. 2, only two bolts 126 are shown, but in some embodiments, additional bolts can be positioned along the edges of the window 121. In some embodiments, the window 121 can include a flange for mounting the window. The flange may have a plurality of through holes through which fasteners (e.g., bolts 126) can pass to secure the window 121 to the enclosure 150. A seal 128 (e.g., an O-ring) can be positioned between the enclosure 150 and the window 121. The bolts 126 can be tightened, causing the O-ring 128 to be compressed between the enclosure 150 and the window 121. In some embodiments, the O-ring 128 produces a hermetic seal. Other approaches can be used to fasten the window 121 to the enclosure 150. The window 121 can be secured to the enclosure 150 by an adhesive, epoxy, or cement.

In some embodiments, the seal described may produce a hermetic seal. A hermetic seal may help reduce particles and contamination from outside the enclosure. A hermetic seal may also help to prevent or reduce the flow of air currents and thus prevent or reduce the flow of ambient temperature changes into the enclosure. This in turn may help reduce temperature instability within the enclosure. In some of the embodiments discussed above, the entire enclosure 150 is hermetically sealed from the ambient air. Thus, the interior of the enclosure 150 is isolated from air currents which can cause temperature variation, and the internal optical elements are protected from external contaminants. In some embodiments a getter (not shown) is located inside the enclosure 150 which can reduce contaminant particles or chemical species. Additional, a desiccant (not shown) can be positioned inside the enclosure 150 to reduce moisture.

Although FIG. 2 shows a single output window, multiple output windows can be used. For example, each beam of light 118, 119, 120 can exit the enclosure 150 via a respective output window. In some embodiments, it is desirable that as much as possible of the enclosure 150 comprise the thermally conductive material, to better achieve temperature uniformity. Accordingly, the output windows can be separated by thermally conductive material and can cover only as much area as necessary to allow light beams 118, 119, 120 to leave the enclosure 150. However, in some embodiments, a single output window is easier and less expensive to construct.

The multi-laser system 100 can include a flow cell connector (not shown) that is mechanically and thermally coupled to the enclosure 150, and the flow cell connector is configured to secure a flow cell 132 so that it intersects and maintains the alignment of the beams of light 118, 119, 120. In some embodiments, the flow cell connector can permanently attach the flow cell 132 to the enclosure 150. However, in some embodiments, the flow cell connector can allow the flow cell 132 to be removably attached to the enclosure 150. In some embodiments, the flow cell connector can be compatible with multiple types and/or sizes of flow cells. For example, the flow cell connector can include a clip, a friction or pressure fit coupling, a threaded portion configured to receive a corresponding threaded portion of the flow cell 132, or a variety of other connectors known in the art or yet to be devised. The flow cell 132 can be a capillary flow cell, and at least part of the flow cell can comprise a transparent material (e.g., fused silica or glass) that allows the light beams 118, 119, 120 to enter the flow cell 132 and interact with a sample fluid contained within the flow cell 132. The flow cell 132 can be a thin hollow tube, forming a flow path that has a diameter of about 10 µm. Other flow cell types and/or sizes can be used, and the flow cell 132 can be oriented differently than as shown in FIG. 1. In some embodiments, the beams of light 118, 119, 120 strike the flow cell over areas centered about 110 µm to about 140 µm apart from each other, and in some embodiments, about 125 µm apart from each other. In some embodiments, the beams of light 118, 119, 120 strike the flow cell over areas centered about 100 µm to about 150 µm apart from each other. In some embodiments, the beams of light 118, 119, 120 strike the flow cell over areas centered about 100 µm to about 500 µm apart from each other. In some embodiments, the beams of light 118, 119, 120 strike the flow cell over areas centered up to about 500 µm apart from each other. In some embodiments, the thermal expansion coefficient of the thermally stable enclosure 150 matches the thermal expansion coefficient of the flow cell 132. Matching of thermal expansion coefficients may help reduce overall stress on the flow cell. For some forms of optical measurements, it may be desirable for the different laser beams to be focused to different locations in the flow cell 132 at specific locations (e.g., areas spaced about 125 µm apart).

Figure 2A:
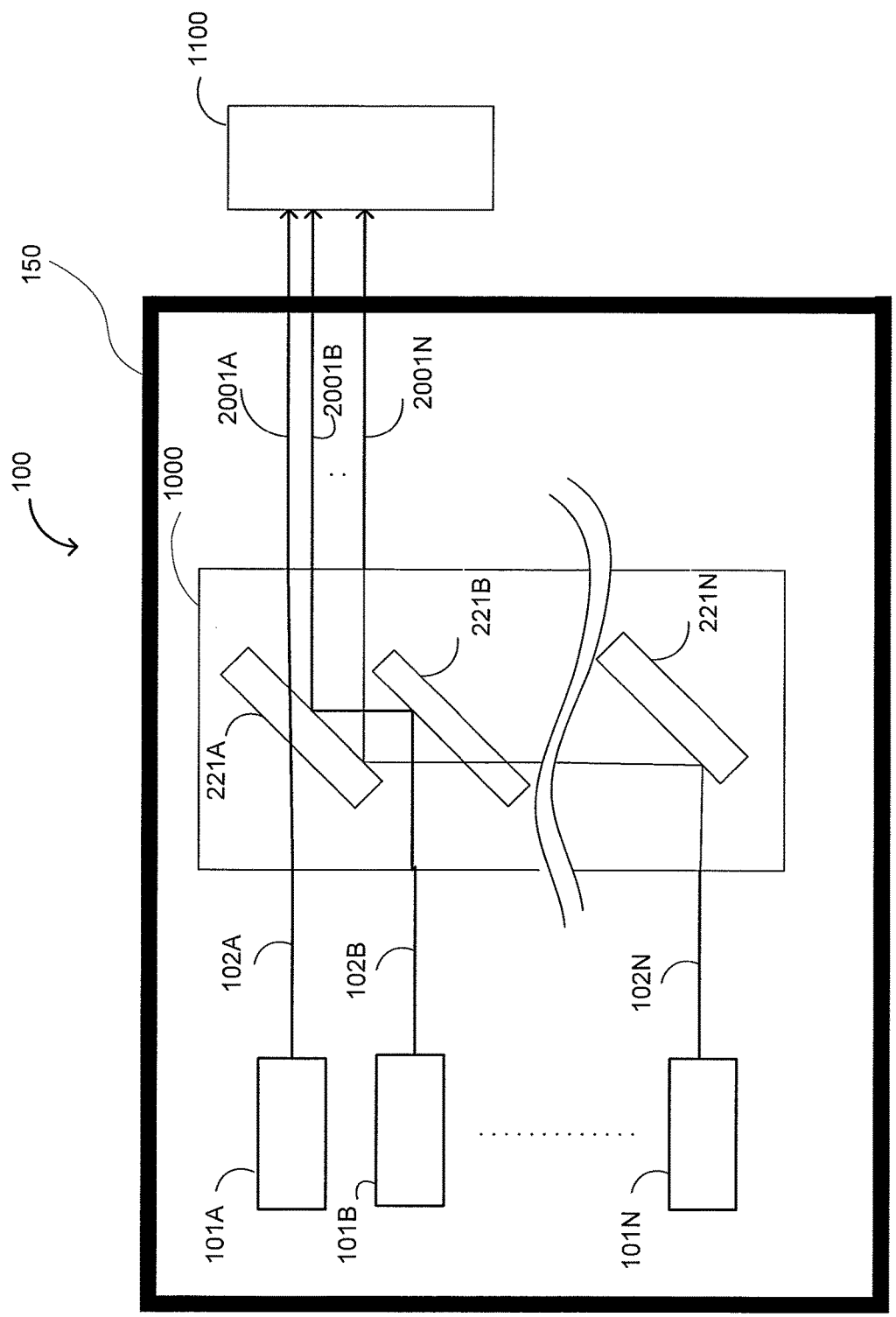
FIG. 2A depicts another example embodiment of a multi-laser system in which the beam positioning/combining system comprises mirrors.

FIG. 2A depicts another example embodiment of a multi-laser system in which the beam positioning/combining system comprises mirrors. As shown in FIG. 2A, a beam positioning combiner system that employs mirrors mounted onto a frame may be used. In various embodiments, the frames on which the mirrors are mountable may be adjustable, e.g., translatable, tiltable, etc. In various embodiments, the wavelength selective mirrors have significantly different reflection or transmission properties at different wavelengths. Accordingly, the wavelength selective mirrors can separate or combine laser beams with different wavelengths.

Through the use of suitable optical coatings, wavelength selective mirrors will selectively reflect (or transmit) light of at least one wavelength and not light of at least one other wavelength. In other embodiments, the wavelength selective mirrors may comprise mirrors with selectivity for a different number of wavelengths. The example embodiment of FIG. 2A depicts a plurality of wavelength-selective mirrors. The mirrors can be used to separate or combine lasers with different wavelengths. Alternatively, substantially non-wavelength selective mirrors that do not selectively reflect (or transmit) light of one laser and not light of another laser may be inserted in the path of the beam to redirect and/or alter the beam path or the beam. Other optical elements can also be inserted into the optical path.

The wavelength-selective mirrors 221A, 221B . . . 221N are configured with highly reflective and anti-reflective coatings in accordance with the wavelengths of the plurality of laser beams 102A, 102B . . . 102N. As shown in FIG. 2A, wavelength selective mirror 221A is configured to be highly reflective of the wavelength of the laser beams 102B through 102N and anti-reflective of the wavelength of laser beam 102A; wavelength-selective mirror 221B is configured to be highly reflective of the wavelength of the laser beam 102B and anti-reflective of the wavelength of the laser beam 102N; and wavelength selective mirror 221N is configured to be highly reflective of the wavelength of the laser beam 102N. Other configurations are possible.

In the multi-laser system 100 shown in FIG. 2A, a plurality of optical paths are depicted. A first optical path originates at laser 101A and is transmitted through wavelength selective mirror 221A and transmitted toward the target object 1100. A second optical path originates at laser 101B, is then reflected at wavelength selective mirrors 221B and 221A, and transmitted toward the target object 1100. An n-th optical path originates at laser 101N, is then reflected at wavelength selective mirror 221N, transmitted at wavelength selective mirror 221B, reflected at wavelength selective mirror 221A, and transmitted toward the target object 1100. Propagating along these paths, laser beams 102A-102N, which may have originally been far from one another, are repositioned to be closer together as beams 2001A-2001N.

The mirrors may be configured to adjust the position of the plurality of laser beams to be at a certain distance of one another, for example in addition to the spacing adjustment that may be provided by placing the lasers at different heights within the enclosure. In some embodiments, the laser beams can be positioned to be coaxial, slightly offset but parallel to each other, or slightly offset but not parallel to each other.

Figure 2B:
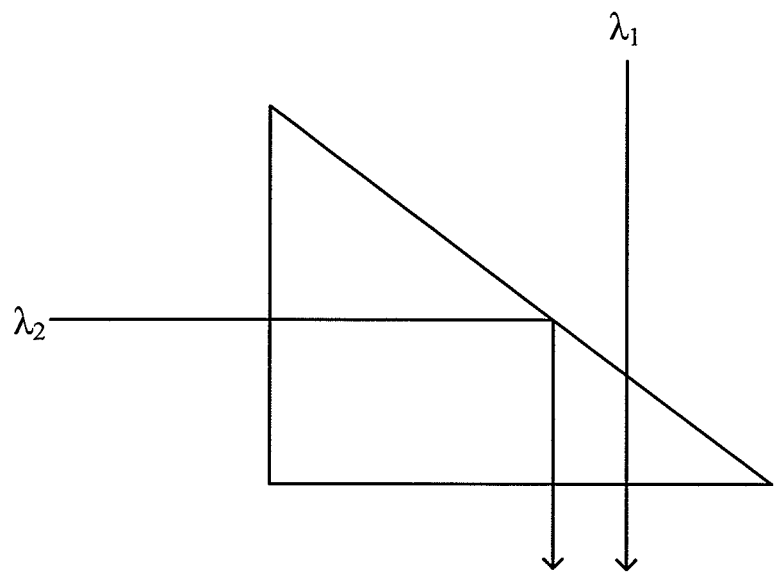
FIG. 2B depicts an example embodiment of a triangular prism.

FIG. 2B depicts an embodiment of a triangular prism. The prism is a transparent optical element comprising a substantially transparent optical material. The prism has flat, polished surfaces that reflect and/or refract light. One or more of these surfaces may be coated with an optical coating such as an interference coating that is reflective and/or anti-reflective. In some embodiments the coating is wavelength selective. For example, the prism may be configured to be highly reflective for certain wavelengths (e.g., of a first laser), and highly anti-reflective for other wavelengths (e.g., of a second laser). The exact angles between the surfaces depend on the application. As shown, the triangular prism generally has a triangular base and rectangular sides. Prisms may be made out of glass, or any material that is transparent to the wavelengths for which they are designed. In some embodiments, the material may include one of polymer, polycarbonate, polyethylene terephthalate, glycol-modified polyethylene terephthalate, amorphous thermoplastic, and/or other substrates. Prisms can be used to reflect light, and to split light into components with different, e.g., wavelength, polarizations. As illustrated in FIG. 2B, a triangular prism includes a glass surface configured to allow transmission of a laser beam of a given wavelength. The surface may be coated with a reflective coating to allow for the reflection of the laser beam of a different wavelength. In some embodiments, each of the wavelength selective mirrors illustrated in FIGS. 2 and 2A may be replaced with a triangular prism as the one illustrated in FIG. 2B. Triangular prisms may also be used that reflect a plurality of wavelength, for example, using total internal reflection. Accordingly, the prisms may be used to redirect laser beams and not for wavelength selection in various cases.

Figure 2C:
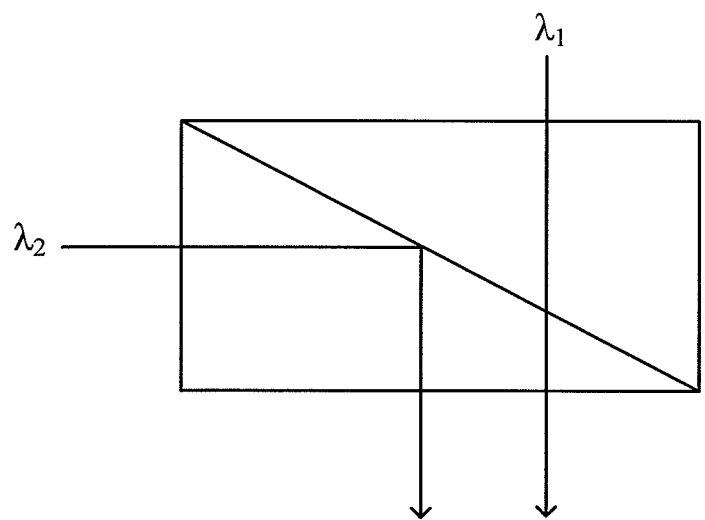
FIG. 2C depicts an example embodiment of a rectangular prism.

FIG. 2C depicts an embodiment of a rectangular prism. This rectangular prism comprises two triangular prisms contacted together. As illustrated in FIG. 2C, a rectangular prism may be used to deflect a beam of light, for example, by 90 degrees, although other angles are also possible. As described above, in some embodiments, prisms employ total internal reflection at the surfaces rather than for dispersion. If light inside the prism hits one of the surfaces at a sufficiently steep angle (greater than the critical angle), total internal reflection occurs and all of the light is reflected. This makes a prism a useful substitute for a mirror in some situations. As described above, triangular prisms or prisms having other shapes can also be used for this purpose. In some embodiments, rectangular prisms can be wavelength selective. For example, the interface between the two triangular prisms or prism portions that make up the rectangular prism shown in FIG. 2C can include an optical coating such as an interference coating that is wavelength selective. In some embodiments, for example, the rectangular prism selectively reflects one laser wavelength and selectively transmits another wavelength. Accordingly, the rectangular prism may include one or more coatings that are highly reflective for one or more laser wavelength. The rectangular prism may include one or more coatings that are anti-reflective for one or more laser wavelength. In some embodiments, each of the wavelength selective mirrors illustrated in FIGS. 2 and 2A may be replaced with a rectangular prism such as the one illustrated in FIG. 2C. Other arrangements and configurations are also possible. For example, a prism (e.g., a rectangular prism) may comprise two or more triangular or other shape prisms that are contacted together.

Figure 2D:
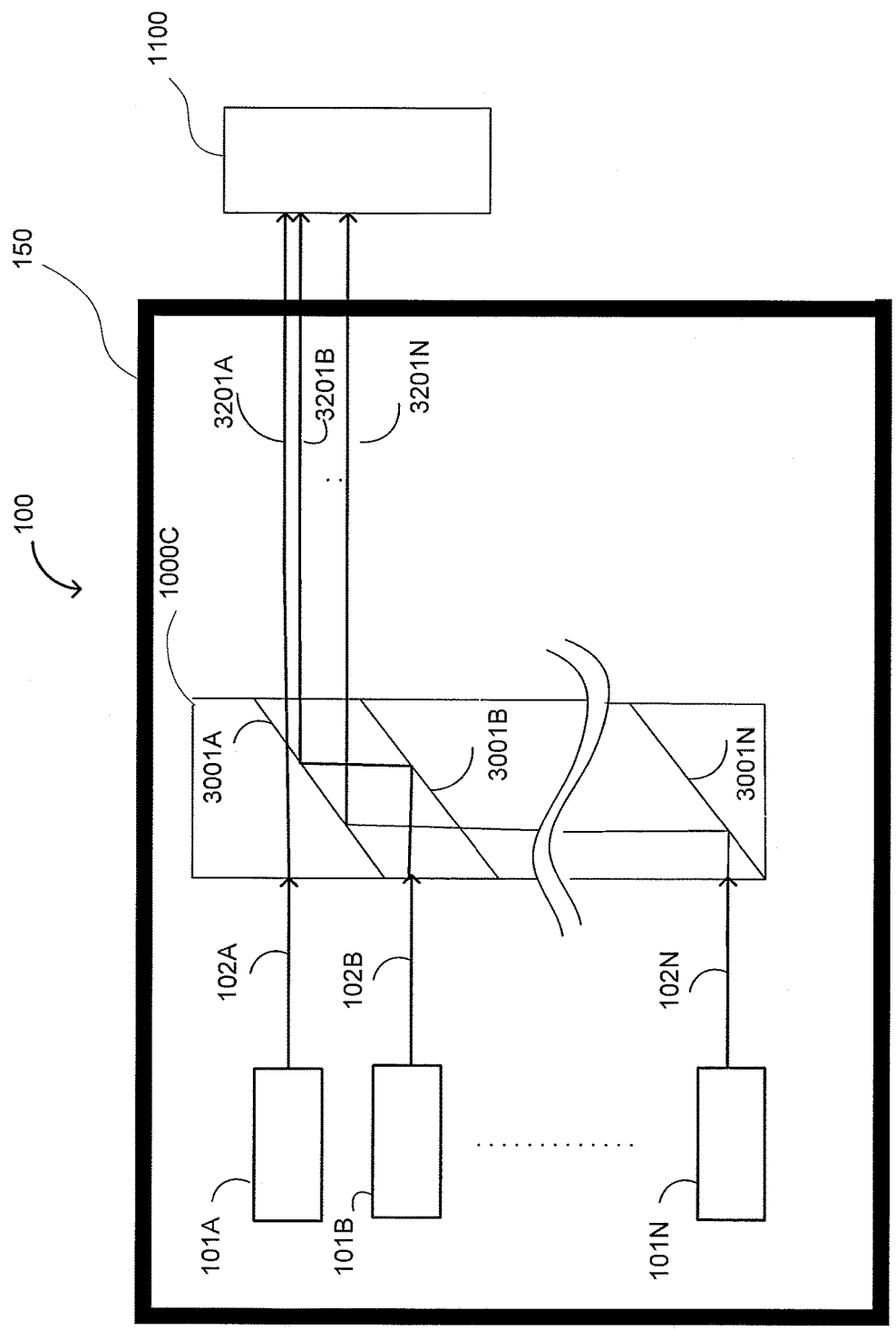
FIG. 2D depicts an example embodiment of a multi-laser system including a prism beam positioning/combining system.

FIG. 2D depicts an embodiment of the multi-laser system including a prism or prism bar beam positioning/combining system 1000C. As shown in FIG. 2D, a prism-based beam positioning combiner system is used to allow the lasers to be arranged in a row at one end of the temperature controlled enclosure. In some embodiments, the prism beam positioning/combining system may include optically contacted prisms having one or more surfaces coated to allow for the selective transmission or reflection of the laser beams. By proper selection of the surface coatings (such as for example wavelength selective reflective interference coatings), various lasers of different wavelength may be combined and output from the prism beam positioning/combining system. The prism beam positioning/combining system may also be configured and arranged with respect to the lasers and the respective laser beam paths such that the laser beams can be positioned such that they are, for example, closely spaced and/or parallel or co-linear on the output side of the prism-based beam positioning combiner system. In other embodiments, the prism beam positioning/combining system can be configured to position the beams in converging or diverging with respect to one another.

The prism illustrated in FIG. 2D may comprise a plurality of prisms or prism portions contacted or adhered together (e.g., using optical contact bonding, or optical adhesive at optical interfaces, and the like) to make a monolithic multi-prism beam combiner, or an aggregated prism. In some embodiments, a monolithic multi-prism may comprise 2, 3, 4, 5, or more prism portions. For example, a monolithic multi-prism may comprise N+1 or N+2 prism portions, where N is the number of lasers. In some embodiments, a monolithic multi-prism may comprise 1, 2, 3, 4, or more optical interfaces. For example, a monolithic prism may comprise N or N+1 optical interfaces, where N is the number of lasers. In various embodiments, one or more interface between the prism portions may be wavelength selective. For example, various of the prism portions may be configured to have one ore more wavelength selective surfaces with one or more highly reflective and/or an anti-reflective (e.g., interference) coatings in accordance with the wavelengths of the plurality of laser beams 102A-102N. As shown in FIG. 2D, the wavelength selective internal surface 3001A may be configured to be highly anti-reflective of the wavelength of the laser beam 102A and highly reflective of the wavelengths of laser beams 102B-102N. The wavelength selective internal surface 3001B may be configured to be highly reflective of the wavelength of the laser beam 102B. The wavelength selective surface internal surface 3001N may be configured to be highly reflective of the wavelength of the laser beam 102N.

In the embodiment shown in FIG. 2D, various prisms are contacted together (e.g., using cement, adhesive (e.g., optical adhesive), optical contact bonding) to form a monolithic multi-prism beam combiner or an integrated or aggregated prism in the shape of a rectangular structure or bar having a rectangular base and rectangular sides. The different prisms that are contacted together may have different shapes. Some of the prisms, for example, may have a base in the shape of a parallelogram and rectangular sides. Some of the other prisms may have different shaped bases and rectangular sides. For example, at least one triangular prism is shown. Other shapes and configurations are also possible.

In the multi-laser system 100 shown in FIG. 2D, a plurality of optical paths are depicted. A first optical path originates at laser 101A, is transmitted through a prism portion to the internal surface 3001A, and then is transmitted toward the target object 1100. A second optical path originates at laser 101B, then is reflected at internal surfaces 3001A and 3001B, and then is transmitted toward the target object 1100. An n-th optical path originates at laser 101N, is transmitted through internal surfaces 101B through 101N-1, then is reflected at internal surface 3001A, and then is transmitted toward the target object 1100. Propagating along these paths, laser beams 102A-102N, which may have originally been far from one another, are repositioned to be closer together as beams 3201A-3201N.

The prisms and interfaces therebetween within the prism-based beam positioning/combining system are configured to adjust the position of the plurality of laser beams to be at a certain distance from one another, in addition to the spacing adjustment that may be provided by placing the lasers at different heights within the enclosure. In some embodiments, the laser beams can be positioned to be coaxial, slightly offset but parallel to each other, or slightly offset but not parallel to each other.

Figure 2E:
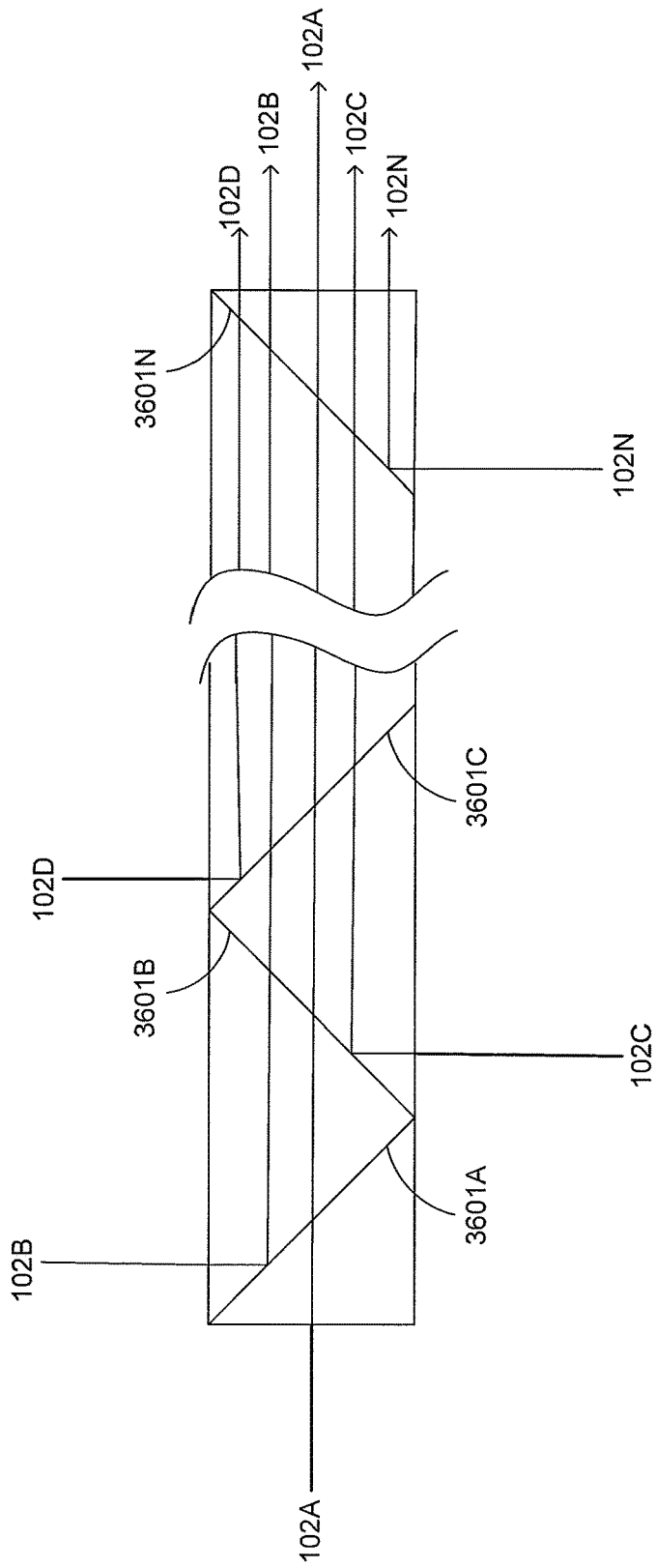
FIG. 2E depicts an example embodiment of a prism beam positioning/combining system.

FIG. 2E depicts another embodiment of a prism beam positioning/combining system. As shown in FIG. 2E, a prism-based beam positioning combiner system is used to allow the lasers to be spread out over the surface of the temperature controlled enclosure's base plate. The surfaces of the prisms may be coated to allow for the transmission or reflection of the laser beams. The prism illustrated in FIG. 2E may comprise a plurality of prisms or prism portions contacted or adhered together to make an aggregated prism or a monolithic multi-prism beam combiner. In various embodiments, one or more interface between the prism portions may be wavelength selective. For example, various of the prism portions may be configured to have one ore more wavelength selective surfaces with one or more highly reflective and/or an anti-reflective (e.g., interference) coatings in accordance with the wavelengths of the plurality of laser beams 102A-102N. As shown in FIG. 2E, the wavelength selective internal surface 3601A may be configured to be highly anti-reflective of the wavelength of the laser beam 102A and highly reflective of the wavelength of laser beam 102B. The wavelength selective internal surface 3601B may be configured to be highly anti-reflective of the wavelength of the laser beams 102A and 102B and highly reflective of the wavelength of laser beam 102C. The wavelength selective surface internal surface 3601C may be configured to be highly anti-reflective of the wavelength of the laser beams 102A, 102B, and 102C, and highly reflective of the wavelength of the laser beam 102D. The wavelength selective surface internal surface 3601N may be configured to be highly anti-reflective of the wavelength of the laser beams 102A, 102B, 102C, through 102N-1, and highly reflective of the wavelength of the laser beam 102N.

In the embodiment shown in FIG. 2E, various prisms are contacted together (e.g., using cement, adhesive (e.g., optical adhesive), optical contact bonding) to form an integrated or aggregated prism in the shape of a rectangular structure or bar having a rectangular base and rectangular sides, or a monolithic multi-prism beam combiner. The different prisms that are contacted together have different shapes. For example, different triangular prisms are shown. Some of the prisms, for example, may have a base in the shape of a right angle triangle and rectangular sides while other prisms may have a base in the shape of an equilateral triangle and have rectangular sides. Other shapes and configurations are also possible.

In the multi-laser system 100 shown in FIG. 2E, a plurality of optical paths are depicted. A first optical path originates at laser 101A, is transmitted through prism portions and internal surfaces 3601A, 3601B, 3601C through 3601N, and is transmitted toward the target object 1100. A second optical path originates at laser 101B, is then reflected at internal surface 3601A, transmitted through prism portions and internal surfaces 3601B, 3601C through 3601N, and toward the target object 1100. A third optical path originates at laser 101C, is then reflected at internal surface 3601B, transmitted through prism portions and internal surfaces 3601C through 3601N, and toward the target object 1100. A fourth optical path originates at laser 101D, is reflected at internal surface 3601C, transmitted through prism portions and internal surfaces 3601D through 3601N, and toward the target object 1100. An n-th optical path originates at laser 101N, is reflected at internal surface 3601N, and transmitted toward the target object 1100. Propagating along these paths, laser beams 102A-102N, which may have originally been coming from different directions and far from one another, are repositioned to be closer together as beams 3701A-3701N. As described herein, the laser beams 102A-102N may also be repositioned to be parallel to each other as beams 3701A-3701N.

A wide range of other aggregated prisms (or monolithic multi-prism beam combiners) comprising a plurality of prism portions contacted together are also possible. Aggregated prisms (or monolithic multi-prism beam combiners) may include optical coating for example at interfaces between prism portions or prisms that make up the aggregated prism. These optical coatings may be wavelength selective reflective coating or may be anti-reflective (AR) coatings. One example of such an aggregated prism comprising a plurality or prisms or prism portions contacted together is the X-prism. Other aggregated prisms, however, may also be used.

A multi-prism beam combiner may be more advantageous than beam combiners using separate dichroic mirrors mounted in individual flexure mounts, mounted using a glue-block approach, or all mounted in a common mount. In a multi-prism beam combiner, all of the reflective surfaces are tied together so that the number of opto-mechanical components that can contribute to the relative movement of the laser beams with respect to each other is greatly reduced thereby improving the system performance. Additionally, the reduced parts count and reduced complexity make for increased ease of manufacturing and should allow for a decrease in system size. Furthermore, the number of surfaces exposed to possible contamination is reduced. Also, the relatively large size of the prism combiner compared to an individual dichroic mirror reduces the impact that the coefficient of thermal expansion (CTE) mismatch between most adhesives, the optics and the metal used in the optical mounts has on beam position.

Figure 3:
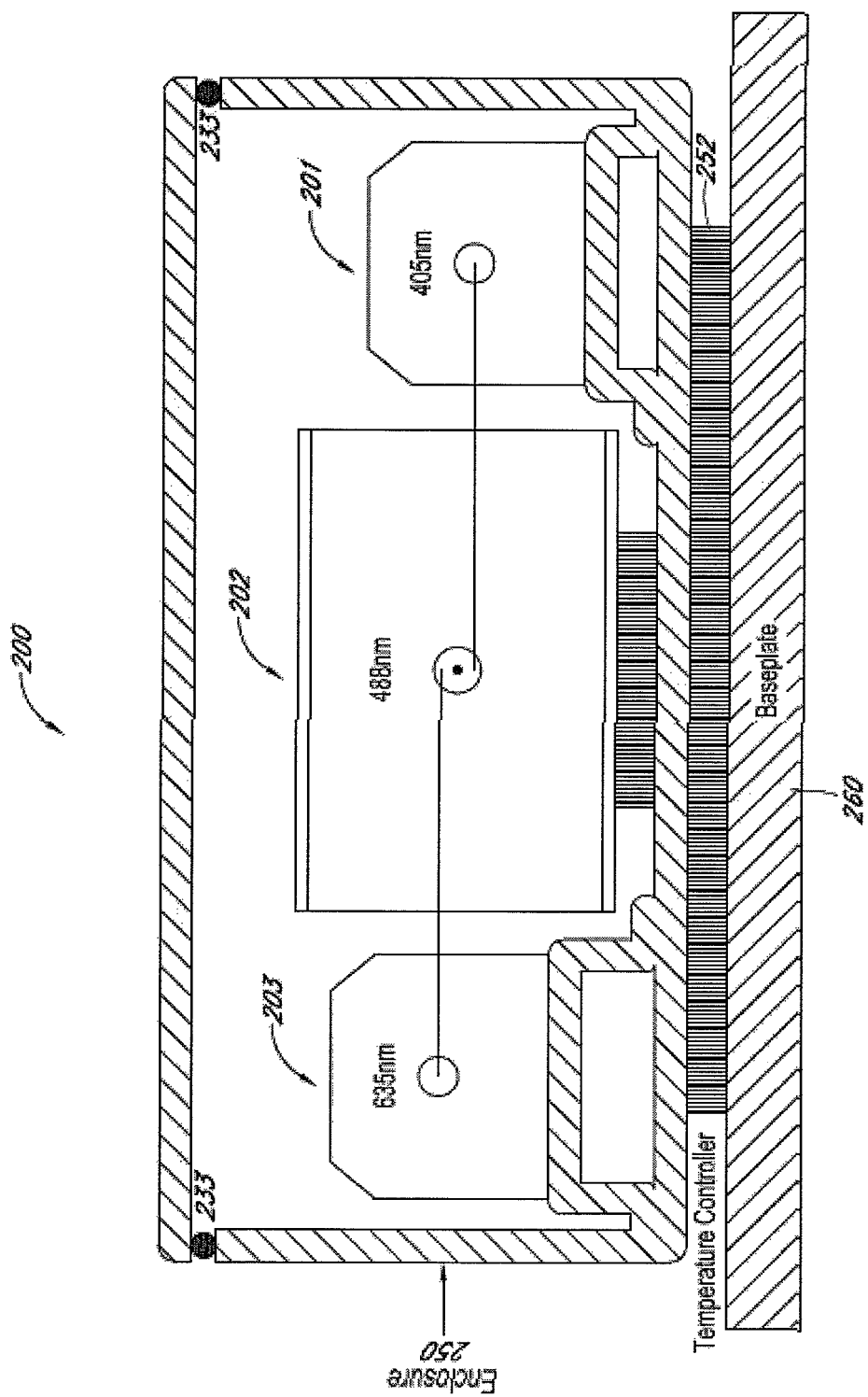
FIG. 3 depicts the front view of the system of FIG. 2.

FIG. 3 depicts the front view of the multi-laser system 100 depicted in FIG. 2. As described above, in some embodiments, the thermally stable enclosure 250 is hermetically sealed. The hermetic sealing may be provided by o-rings 233. Again, hermetically sealing can reduce particles and contamination from outside the enclosure. Moreover, as described above, a hermetic seal may also reduce or prevent the flow of air currents and thus prevent or reduce the flow of ambient temperature changes into the enclosure. This in turn may reduce temperature instability within the enclosure. In some embodiments, the top of enclosure 250 may be thermally coupled, possibly with a copper braid, to the main body of the enclosure 250 to reduce thermal effects.

As shown in FIG. 3, the multi-laser system may further comprise a temperature controller 252. In some embodiments, the temperature controller 252 may comprise a thermo electric cooler (TEC), a temperature sensor and control electronics. The TEC may pump heat from one side to the other depending on the direction of current flow through the TEC. The direction of current flow may be determined by the control electronics. In some embodiments, for example, if the ambient temperature were higher than the enclosure 250's set point temperature then the control electronics may direct current flow through the TEC so that heat was pumped out of the enclosure 250 thereby helping maintain the enclosure's set point temperature. In other embodiments, if the ambient temperature were lower than the enclosure 250's set point temperature, then the control electronics may reverse the current flow through the TEC so that heat was pumped into the enclosure 250 again helping maintain the enclosure's set point temperature. A temperature controller 252 can be thermally coupled to the thermally stable enclosure 250. The temperature controller 252 can include a temperature sensor (not shown) to measure the temperature of the thermally stable enclosure 250, and to provide feedback to the control electronics. In some embodiments, the temperature sensor may comprise a thermistor. The temperature controller 252 may remove heat from or add heat to the thermally stable enclosure 250 in order to maintain a substantially constant temperature in the thermally stable enclosure 250. The high thermal conductivity of the material of the enclosure 250 helps the temperature controller to relatively quickly adjust the temperature within the enclosure 250 in response to temperature variations outside of the enclosure 250 and also reduce the presence of temperature variations across the enclosure 250.

As shown in FIG. 3, the multi-laser system may also comprise a baseplate 260. The baseplate 260 may act as a thermal heat sink for the temperature controller 252.

In some embodiments, the temperature within the thermally stable enclosure 250 can be held stable to within ±1° C., ±2° C., ±3° C., ±5° C., etc., for example, of a target temperature. In some embodiments, the temperatures of the wavelength selective mirrors and the focusing optics can be held to be within ±1° C., ±2° C., ±3° C., ±5° C., etc. of one another. In some embodiments, the temperature over a substantial portion of the enclosure can be held to be within ±1° C., ±2° C., ±3° C., ±5° C., etc. In some embodiments, the temperature over the entire enclosure can be held to be within ±1° C., ±2° C., ±3° C., ±5° C., etc., for example, of a target temperature. In some embodiments, the temperature within the enclosure can be held to be within ±1° C., ±2° C., ±3° C., ±5° C., etc., for example, of a target temperature. In some embodiments, the temperature within the thermally stable enclosure 250 can be held within ±1° C. of the target temperature. In some embodiments, the target temperature can be between 10° C. and 50° C. In some embodiments, the target temperature can be between about 15° C. and about 45° C. In other embodiments, the target temperature can be between about 15° C. and about 35° C. In other embodiments, the target temperature can be between about 10° C. and about 40° C. The temperature controller 252 also maintains the focused laser beams aligned with respect to the flow cell over a wide range of ambient temperatures. In some embodiments, the range of ambient temperatures can be between about 10° C. and about 55° C. In some embodiments, the range of ambient temperatures can be between about 10° C. and about 50° C. In some embodiments, the range of ambient temperatures can be between about 15° C. and about 45° C. In other embodiments, the range of ambient temperatures can be between about 15° C. and about 35° C. In other embodiments, the range of ambient temperatures can be between about about 10° C. and about 40° C.

FIG. 3 also depicts that the three lasers 201, 202, and 203 may be placed at different heights within the enclosure 250. The placement at different heights may assist in positioning the focused laser beams at a desired spacing from one another at the flow cell. By disposing the lasers at different heights, the focused beams at the flow cell may be separated by between about 110 µm and about 140 µm of one another. In some embodiments, the focused beams may be separated by between about 100 µm to about 150 µm of one another. In some embodiments, the focused beams may be separated by between about 100 µm to about 500 µm of one another. In some embodiments, the focused beams may be separated by up to about 500 µm of one another. The wavelength selective mirrors, however, can additionally be adjusted to account for the imperfection in laser positions that may result, for example, from manufacturing tolerances. Accordingly, the wavelength selective mirrors may establish better positioning of the beams directed onto the flow cell.

Figure 4:
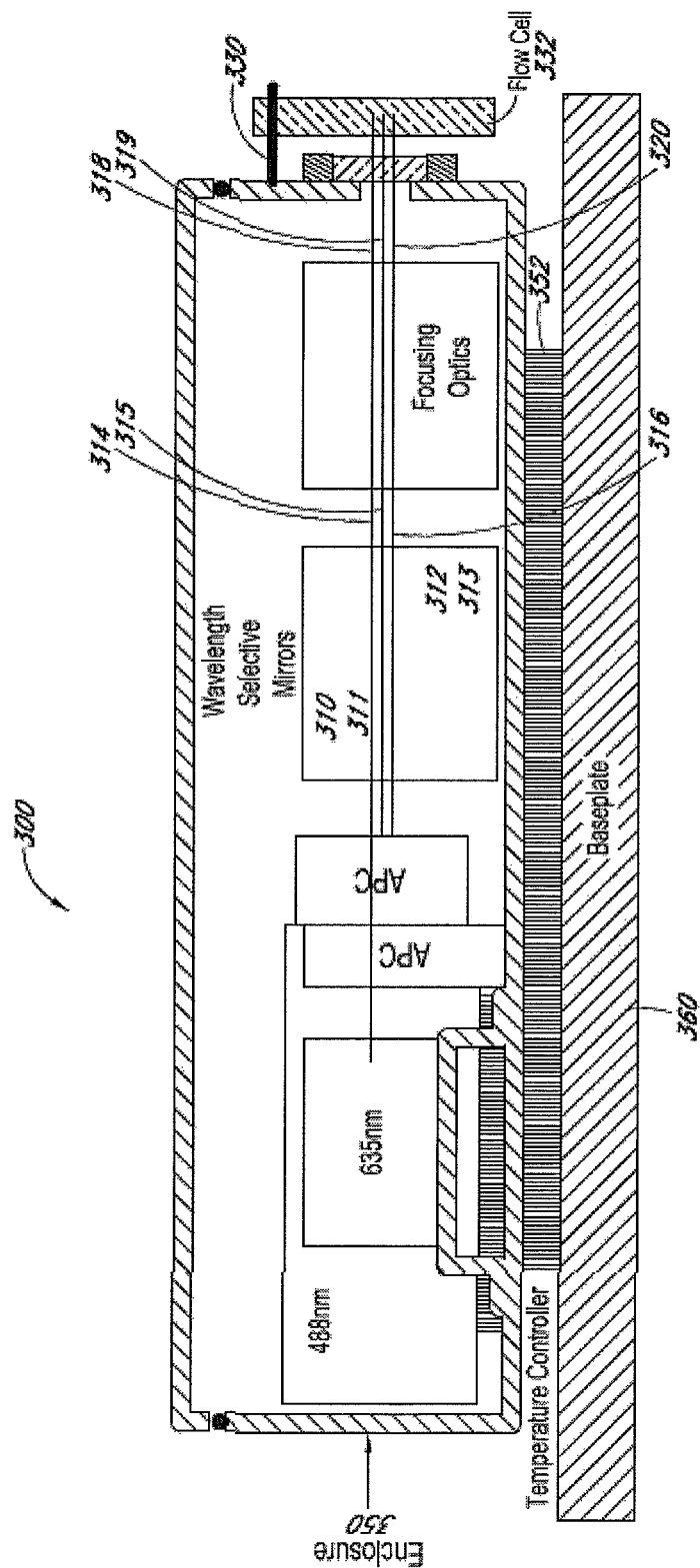
FIG. 4 depicts the side view of the system of FIG. 2.

FIG. 4 depicts the side view of the multi-laser system 100 depicted in FIG. 2. FIG. 4 also shows the placement of the lasers at different heights. The thermally stable enclosure 350 comprises wavelength selective mirrors 310, 311, 312, 313 that are configured to adjust the position of the plurality of laser beams 314, 315, 316 to be at a certain distance of one another, in addition to the spacing adjustment that may be provided by placing the lasers at different heights within the enclosure 350. In some embodiments, the laser beams can be positioned to be coaxial, slightly offset but parallel to each other, or slightly offset but not parallel to each other. In some embodiments, the plurality of focused laser beams 318, 319, 320 may be separated by about 110 µm and about 140 µm of one another. In some embodiments, the plurality of focused laser beams 318, 319, 320 may be separated by about 100 µm and about 150 µm of one another. In some embodiments, the plurality of focused laser beams 318, 319, 320 may be separated by about 100 µm and about 500 µm of one another. In some embodiments, the plurality of focused laser beams 318, 319, 320 may be separated by up to about 500 µm of one another. In some embodiments, the plurality of focused laser beams 318, 319, 320 may be positioned to be at a distance of about 125 µm of one another.

As can be seen in FIG. 4, the thermally stable enclosure 350 comprises a top, a bottom, and four sides. In some embodiments, the thermally stable enclosure 350 has a width of about 3 inches or less, a length of about 6 inches or less, and/or a height of about 2 inches or less. In other embodiments, the length, the width, and the height of the thermally stable enclosure 350 may be relatively larger or smaller. In some embodiments, the thermally stable enclosure 350 has a width of about 6 inches or less, a length of about 12 inches or less, and/or a height of about 3 inches or less. In some embodiments, the thermally stable enclosure 350 has a volume of 36 cubic inches (in$^3$) or less. With a relatively small volume, the temperature controller is better able to adjust the temperature of the enclosure and system in response to variations in ambient temperature. The temperature controller is thus able to avoid temporal variations in temperature induced by fluctuation in ambient conditions. The relatively small volume may reduce temperature instabilities within the enclosure 350 by reducing temperature gradients across the enclosure 350. In other embodiments, the volume of the thermally stable enclosure 350 may be relatively larger or smaller. Also shown in FIG. 4 is the flow cell connection 330, described above.

Figure 5:
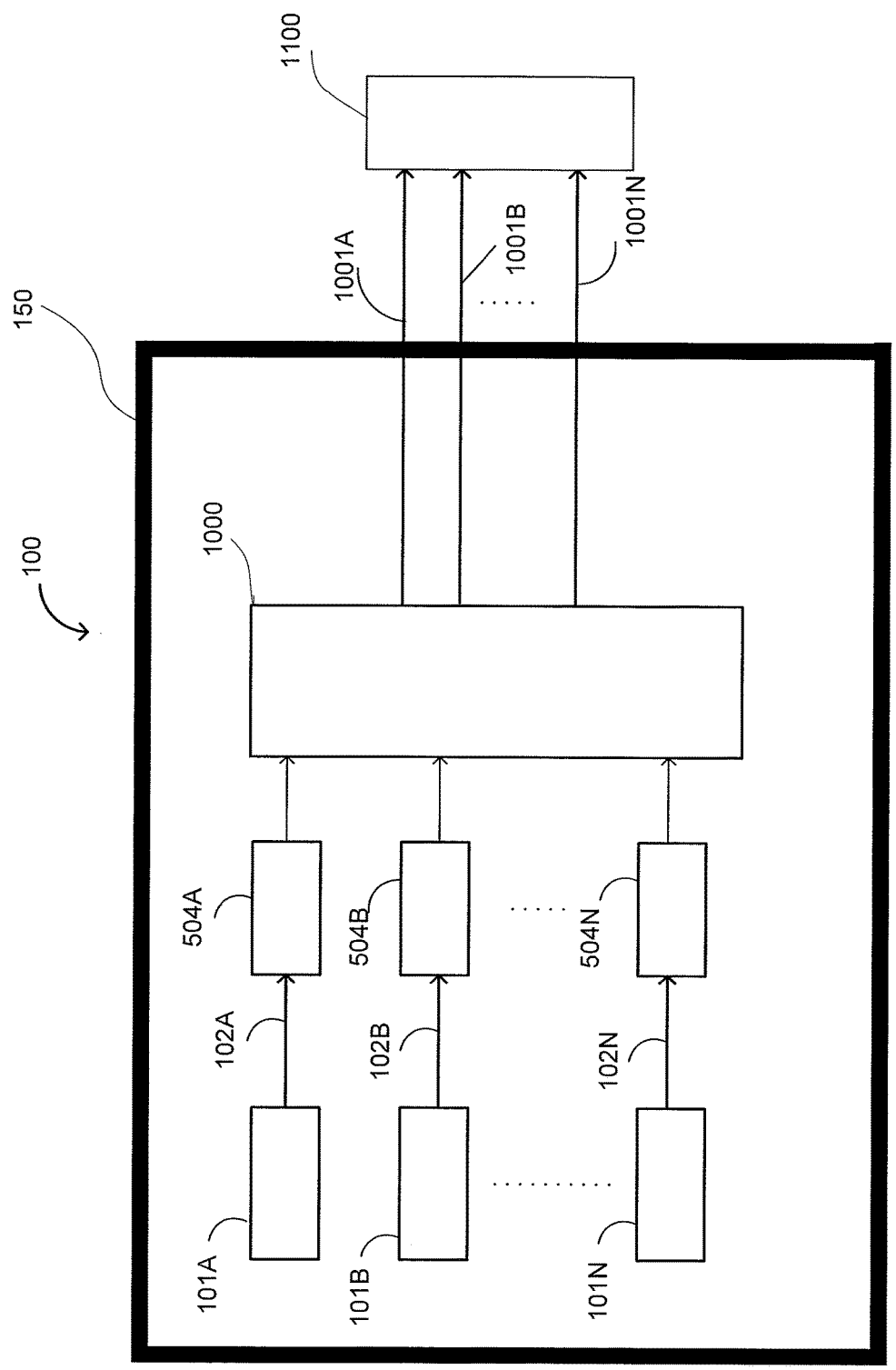
FIG. 5 depicts an example embodiment of a multi-laser system further including a plurality of beam adjusters.

FIG. 5 depicts an example embodiment of a multi-laser system further including an optional plurality of beam adjusters 504A-504N. In various embodiments, the boresight and centration errors of the n laser beams and/or the angular and lateral positioning errors of the opto-mechanical components may be compensated for by using the separate beam position adjusters 504A-504N. The adjusted laser beams may then be positioned and/or combined into a desired spatial arrangement by the beam positioning/combining system that a specific application requires.

Figure 6:
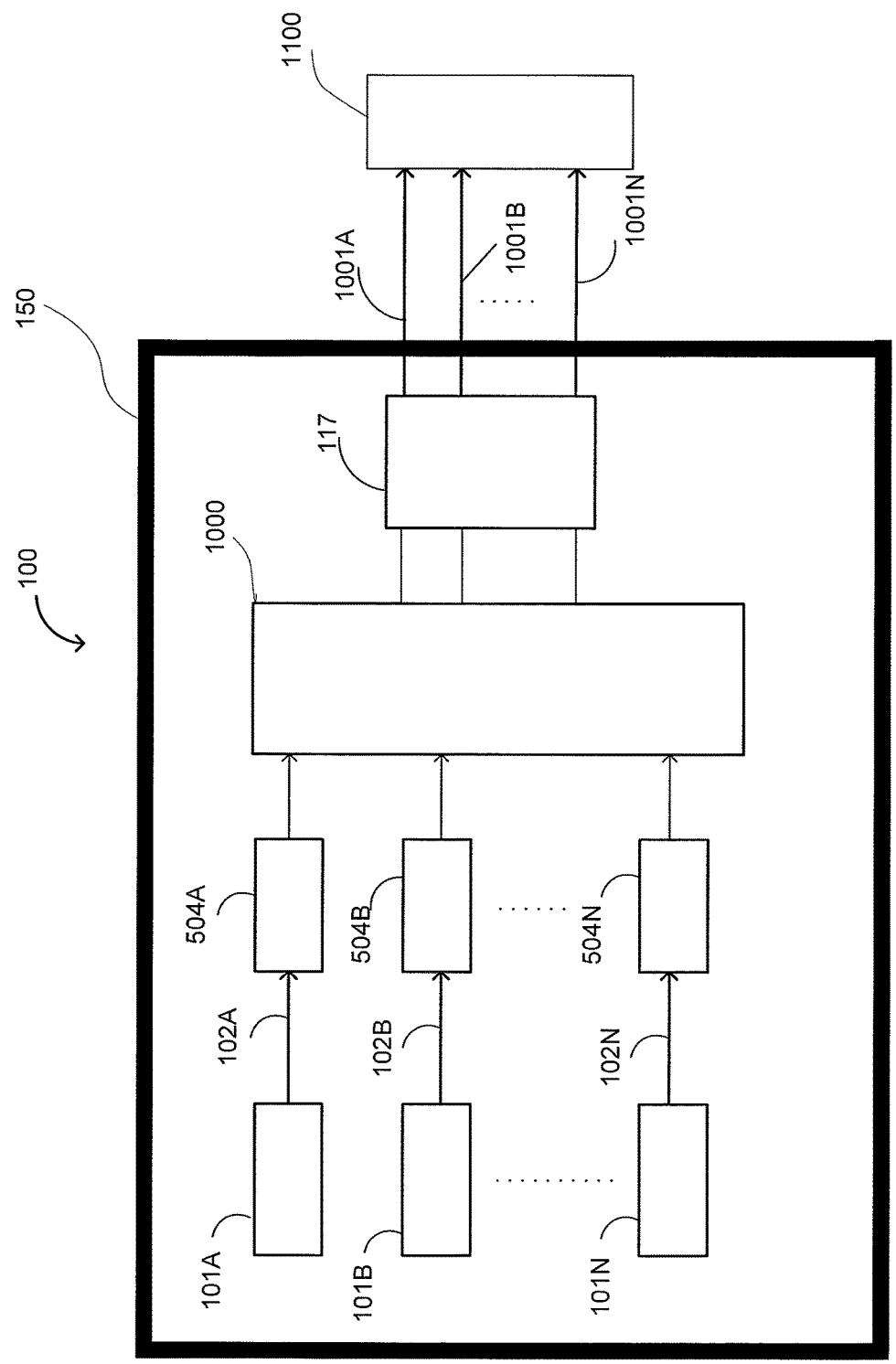
FIG. 6 depicts an example embodiment of a multi-laser system further including focusing optics.

FIG. 6 depicts the embodiment of the multi-laser system of FIG. 5 further including optional focusing or beam shaping optics 117. As described in relation to FIG. 2 above, beam focusing optics or beam shaping optics may be used to provide size reduction and/or shaping to the output laser beams. For example, the focusing/beam shaping optics may focus a laser beam down to a smaller spot. The focusing/beam shaping optics may also be used to change the shape of the laser beams.

The output laser beams depicted in FIG. 6 may have respective spot sizes of between about 55 µm and about 110 µm in one direction and between about 5 µm and about 15 µm in another direction (e.g., perpendicular to the one direction). In other embodiments, the laser beams may have respective spot sizes of between about 70 µm and about 110 µm in one direction and between about 5 µm and about 15 µm in another direction (e.g., perpendicular to the one direction). In other embodiments, the laser beams may have respective spot sizes of between about 50 µm and about 150 µm in one direction and between about 5 µm and about 20 µm in another direction (e.g., perpendicular to the one direction). In other embodiments, the laser beams may have spot sizes of between about 55 µm and about 100 µm in one direction and between about 5 µm and about 15 µm in another direction (e.g., perpendicular to the one direction). In other embodiments, the laser beams may have spot sizes of between about 70 µm and about 100 µm in one direction and between about 5 µm and about 15 µm in another direction (e.g., perpendicular to the one direction). In other embodiments, the laser beams may have respective spot sizes of between about 50 µm and about 150 µm in one direction and between about 5 µm and about 20 µm in another direction (e.g., perpendicular to the one direction). In some embodiments, the output laser beams 118, 119, 120 may have respective spot sizes of about 80 µm in one direction and about 10 µm in another direction (e.g., perpendicular to the one direction). In other embodiments, the output laser beams 118, 119, 120 may have respective spot sizes of about 100 µm in one direction and about 10 µm in another direction (e.g., perpendicular to the one direction). These may correspond to major and minor axes of an ellipse for a beam with an elliptical cross-section and spot shape. Other sizes and shapes are possible for the light beams.

Figure 7:
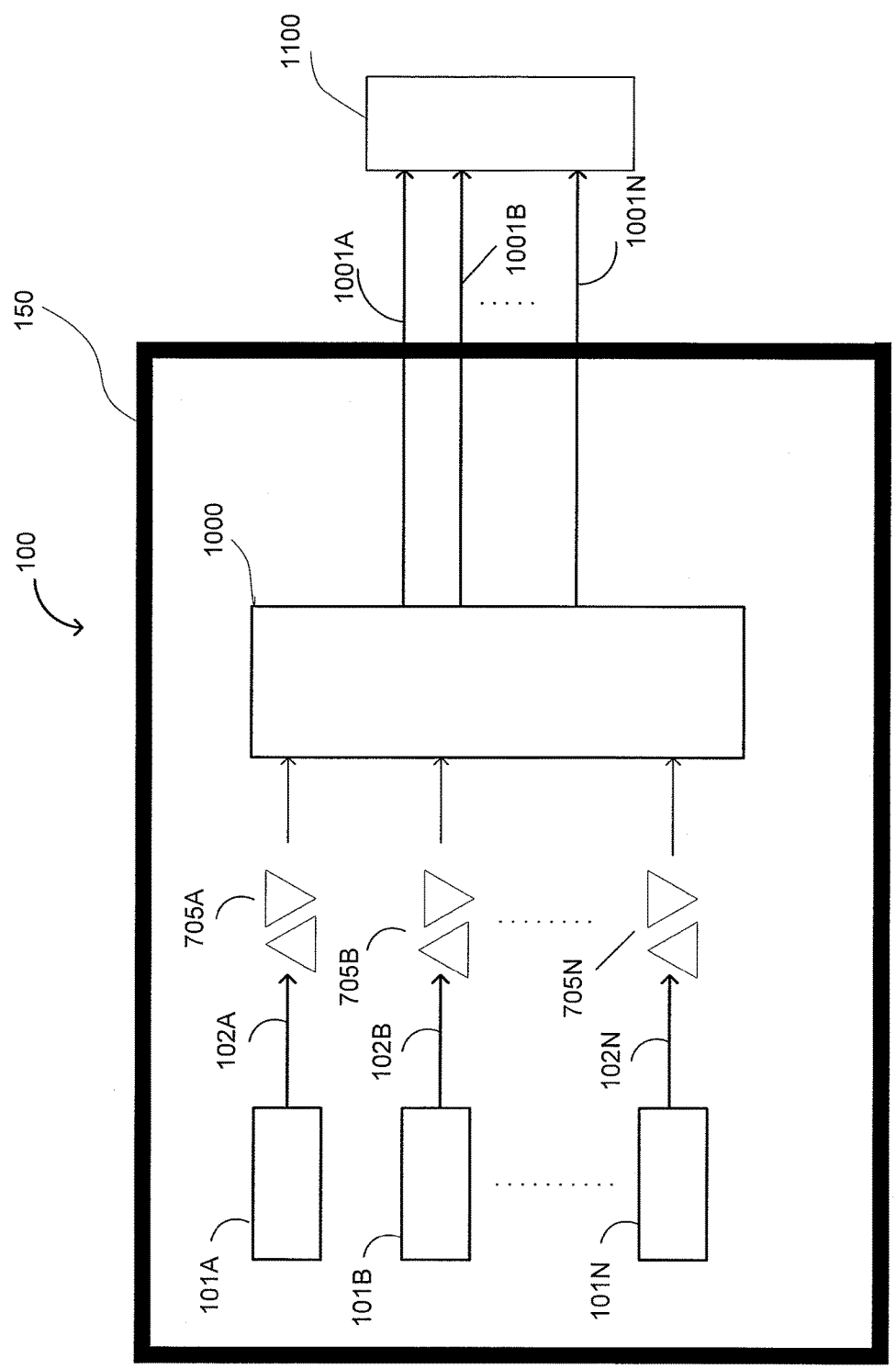
FIG. 7 depicts an example embodiment of a multi-laser system in which the beam adjusters comprise Risley prism pairs.

FIG. 7 depicts an example embodiment of a multi-laser system in which the beam adjusters 504A-504N comprise Risley prism pairs 705A-705N. In other embodiments, other systems may be used as the separate beam position adjusters 504A-504N. In various embodiments, the laser boresight and opto-mechanical angular errors may be compensated for by rotating the Risley prisms while the laser centration and opto-mechanical lateral positioning errors may be compensated for by adjusting the Risley prism assembly pitch, yaw, and/or separation between the individual prisms (e.g., by adjusting one or both of the individual prisms). The aligned laser beams may then be positioned or combined into a desired spatial arrangement that a specific application requires by the beam positioning/combining system.

FIG. 7 depicts a Risley prism pair used with each laser beam. In other embodiments, a different number of Risley prisms may be used. Other optical elements can also be inserted into the optical path.

In various embodiments, Risley prisms comprising wedged optics, usually used in pairs, to redirect optical beams are used. In various embodiments, an incoming light beam enters a Risley prism pair, experiences refraction and redirection under Snell's Law, and exits the Risley prism pair. In some configuration of the Risley prisms, there is just a translation of the output beam with respect to the input beam. If the arrangement of the Risley prisms with respect to each other is changes, the output beam may experience an elevation deviation. The ability to control azimuth may be provided by rotating the prism pair together. Therefore, the Risley prism pair can be used to direct a light beam at a variety of elevation angles and azimuthal angles.

The Risley prism pairs 705A-705N wedge angles and the azimuthal rotation between the prisms are determined in accordance with the respective laser beam 102A-102N. As shown in FIG. 6, Risley prism pair 705A is configured to adjust the laser beam 102A, Risley prism pair 705B is configured to adjust the laser beam 102B, and Risley prism pair 705N is configured to adjust the laser beam 102N.

In the multi-laser system 100 shown in FIG. 7, a plurality of optical paths are depicted. A first optical path originates at laser 101A, passes through the Risley prism pair 705A, where laser boresight, centration and opto-mechanical angular and lateral positioning errors may be compensated through adjustment of the wedge angles of and the azimuthal rotation between the prism pair 705A, and then arrives at the beam combining/positioning system 1000. A second optical path originates at laser 101B, passes through the Risley prism pair 705B, where laser boresight, centration and opto-mechanical angular and lateral positioning errors may be compensated through adjustment of the wedge angles of and the azmiuthal rotation between the prism pair 705B, and then arrives at the beam combining/positioning system 1000. An N-th optical path originates at laser 101N, passes through the Risley prism pair 705N, where laser boresight, centration and opto-mechanical angular and lateral positioning errors may be compensated through adjustment of the wedge angles of and the azimuthal rotation between the prism pair 705N, and then arrives at the beam combining/positioning system 1000.

Propagating along these paths, laser beams 102A-102N, which may have originally been far from one another, are repositioned to be closer together as beams 1001A-1001N. In some embodiments, the beams 1001A-1001N are parallel to one another. In other embodiments, the beams 1001A-1001N are not parallel to one another. Other optical components (e.g., lenses, prisms, polarization rotators, waveplates, etc.) can be included to alter the laser beams and/or optical paths.

Figure 8A:
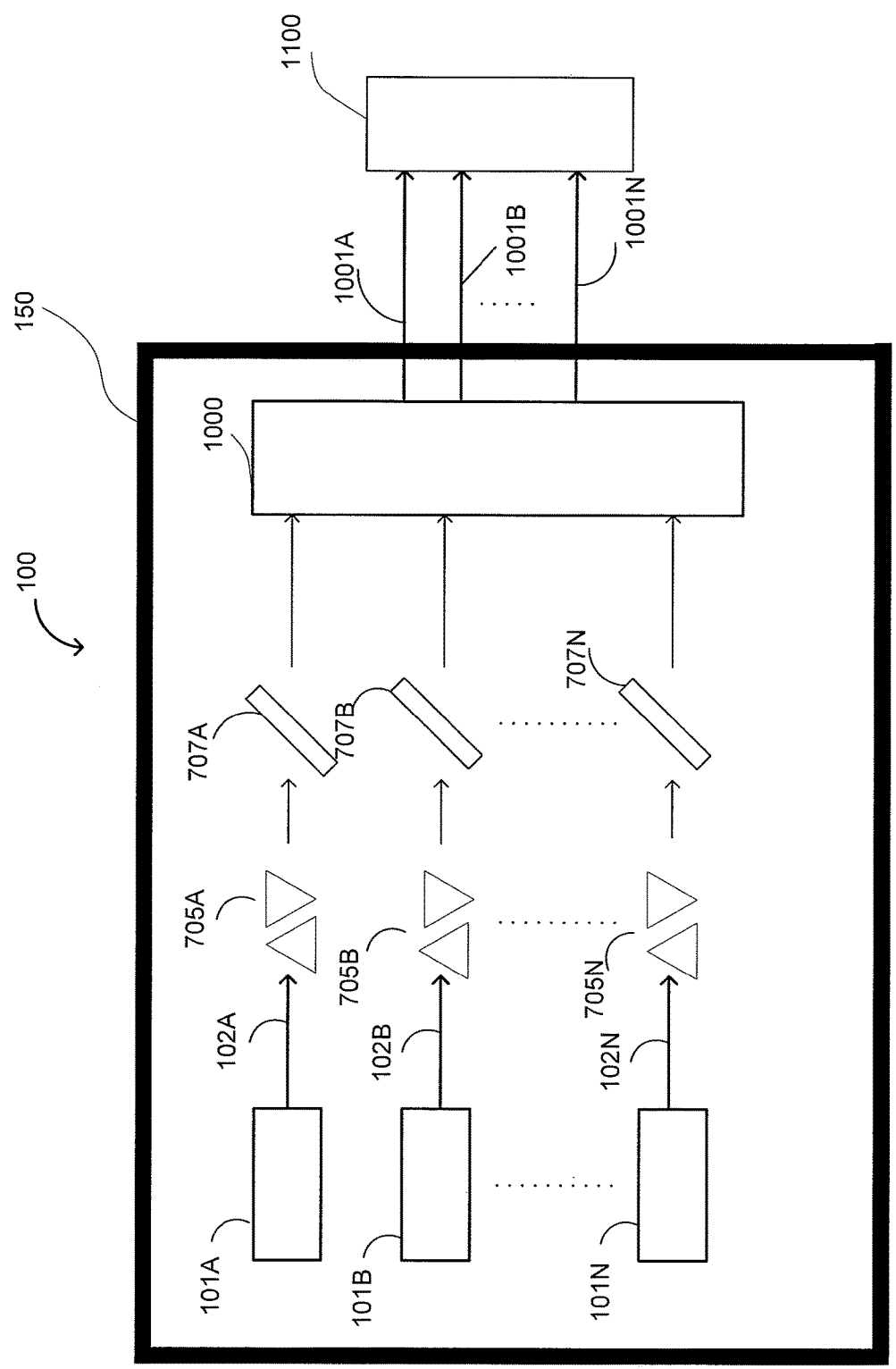
FIGS. 8A-8B depict example embodiments of a multi-laser system in which the beam adjusters comprise Risley prisms and plane parallel plates.
Figure 8B:
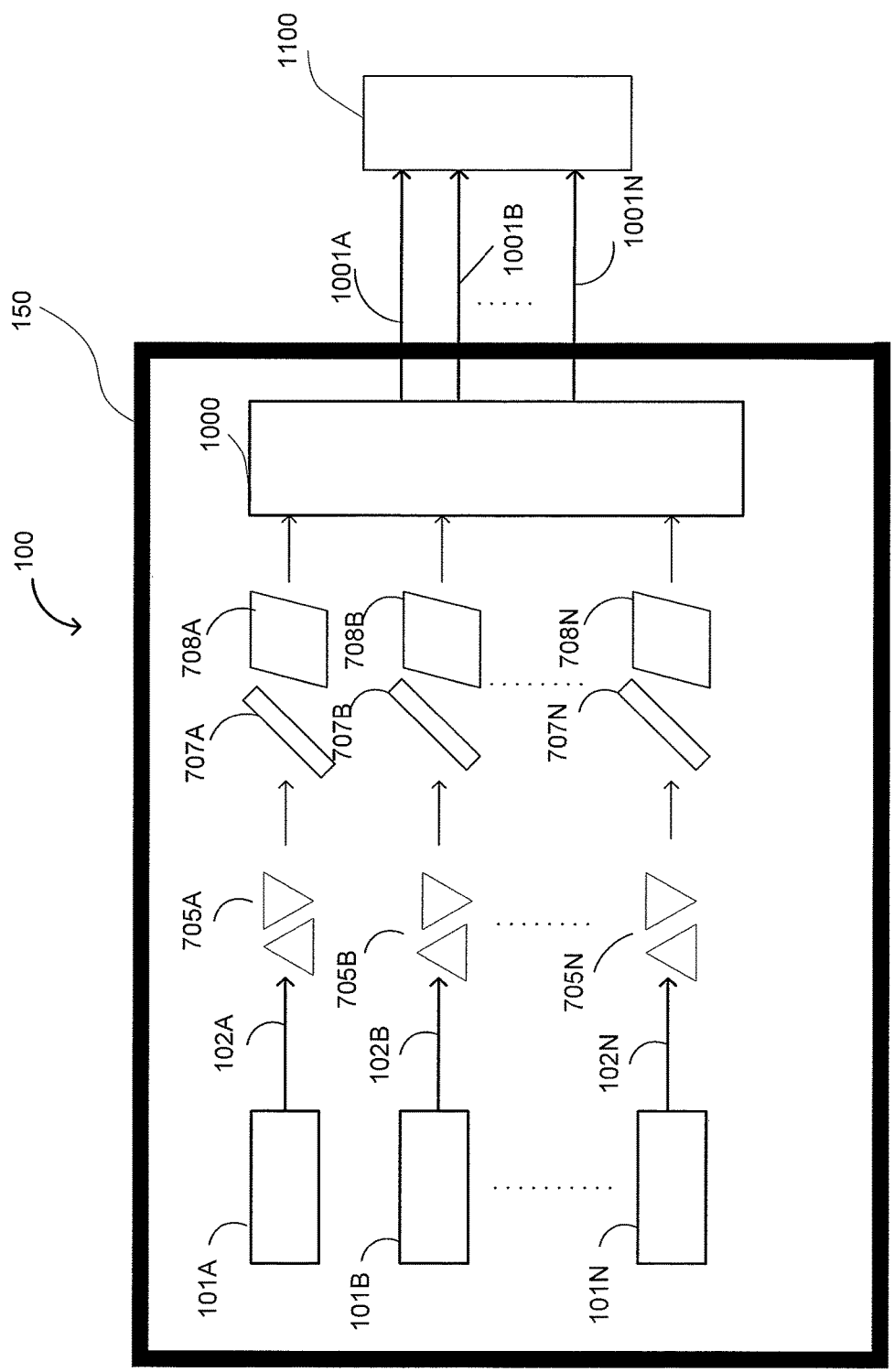

FIGS. 8A-8B depict example embodiments of a multi-laser system in which the beam adjusters comprise Risley prisms and plane parallel plates. In the embodiment of FIG. 8A, a combination of Risley prism pairs 705A-705N and glass etalon plates 707A-707N are used for the separate beam position adjusters 504A-504N illustrated in FIG. 5. In other embodiments, the etalon plates may be comprised of material other than glass. In some embodiments, the plane parallel plates may be made out of glass, or any material that is transparent to the wavelengths for which they are designed. In some embodiments, the material may include one of polymer, polycarbonate, polyethylene terephthalate, glycol-modified polyethylene terephthalate, amorphous thermoplastic, and/or other substrates. The etalon plates comprise plane parallel plates. Other optical elements may however be used in different embodiments. Adjustment of the beams may be provided for by using the combination of Risley prism pairs as described in relation to FIG. 7 above, and glass etalon plates 707A-707N. In the embodiment of FIG. 8A, a single glass etalon plate may be used for providing correction to lateral positioning errors in both x and y planes. In the embodiment of FIG. 8B, a separate glass etalon plate is used for correcting later positioning errors in each (e.g., by being tiltable along one axis) of the x and y planes or in both (e.g., by being tiltable along multiple axes) of the x and y planes.

In various embodiments, the laser boresight and opto-mechanical angular errors may be compensated for by rotating the prisms while the laser centration and opto-mechanical lateral positioning errors may be compensated for by adjusting the pitch and/or yaw of the parallel optical plate. The aligned laser beams may then be positioned or combined into a desired spatial arrangement by the beam positioning/combining system that a specific application requires.

In the multi-laser system 100 shown in FIG. 8A, a plurality of optical paths are depicted. A first optical path originates at laser 101A, passes through the Risley prism pair 705A, where laser boresight and opto-mechanical angular errors may be compensated through adjustment of the wedge angles of the prism pair 705A, passes through the glass etalon plate 707A, where laser centration and opto-mechanical lateral positioning errors may be compensated for by adjusting the pitch and/or yaw of the glass etalon plate 707A, and then arrives at the beam combining/positioning system 1000. A second optical path originates at laser 101B, passes through the Risley prism pair 705B, where laser boresight and opto-mechanical angular errors may be compensated through adjustment of the wedge angles of the prism pair 705B, passes through the glass etalon plate 707B, where laser centration and opto-mechanical lateral positioning errors may be compensated for by adjusting the pitch and/or yaw of the glass etalon plate 707B, and then arrives at the beam combining/positioning system 1000. An N-th optical path originates at laser 101N, passes through the Risley prism pair 705N, where laser boresight, and opto-mechanical angular errors may be compensated through adjustment of the wedge angles of the prism pair 705N, passes through the glass etalon plate 707N, where laser centration and opto-mechanical lateral positioning errors may be compensated for by adjusting the pitch and/or yaw of the glass etalon plate 707N, and then arrives at the beam combining/positioning system 1000.

In the multi-laser system 100 shown in FIG. 8B, a plurality of optical paths are depicted. A first optical path originates at laser 101A, passes through the Risley prism pair 705A, where laser boresight and opto-mechanical angular errors may be compensated through adjustment of the wedge angles of the prism pair 705A, passes through glass etalon plates 707A, 708A, where laser centration and opto-mechanical lateral positioning errors may be compensated for by adjusting the pitch and/or yaw of the glass etalon plates 707A and/or 708A, and then arrives at the beam combining/positioning system 1000. A second optical path originates at laser 101B, passes through the Risley prism pair 705B, where laser boresight and opto-mechanical angular errors may be compensated through adjustment of the wedge angles of the prism pair 705B, passes through glass etalon plates 707B, 708B, where laser centration and opto-mechanical lateral positioning errors may be compensated for by adjusting the pitch and/or yaw of the glass etalon plates 707B and/or 708B, and then arrives at the beam combining/positioning system 1000. An N-th optical path originates at laser 101N, passes through the Risley prism pair 705N, where laser boresight, and opto-mechanical angular errors may be compensated through adjustment of the wedge angles of the prism pair 705N, passes through glass etalon plates 707N, 708N, where laser centration and opto-mechanical lateral positioning errors may be compensated for by adjusting the pitch and/or yaw of the glass etalon plates 707N and/or 708N, and then arrives at the beam combining/positioning system 1000.

Propagating along these paths, laser beams 102A-102N, which may have originally been far from one another, are repositioned to be closer together as beams 1001A-1001N. In some embodiments, the beams 1001A-1001N are parallel to one another. In other embodiments, the beams 1001A-1001N are not parallel to one another. Other optical components (e.g., lenses, prisms, polarization rotators, waveplates, etc.) can be included to alter the laser beams and/or optical paths.

Figure 9:
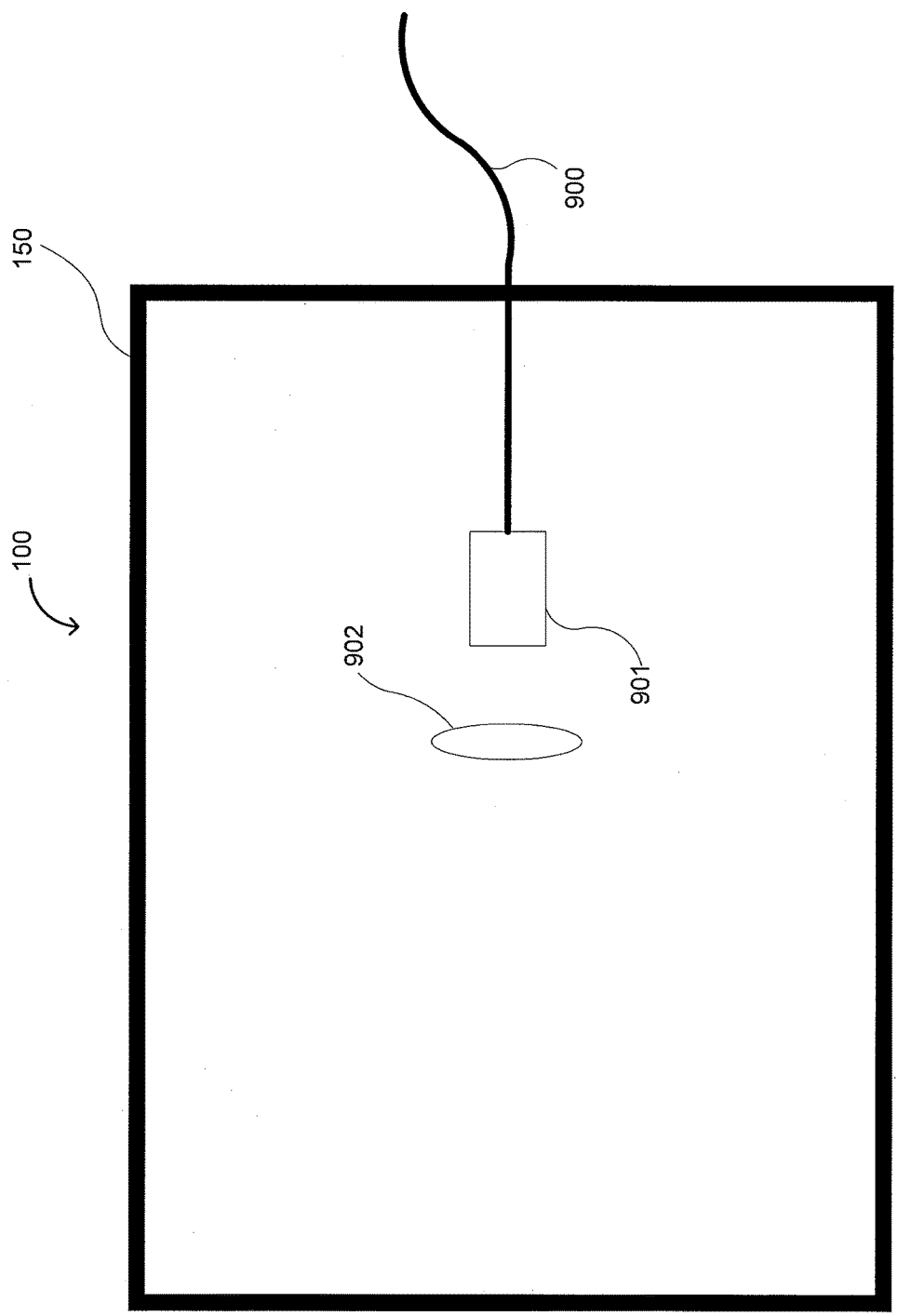
FIG. 9 depicts an example embodiment of a multi-laser system in which the target object comprises an optical fiber or waveguide.

FIG. 9 depicts an example embodiment of a multi-laser system in which the target object 1100 comprises an optical fiber or waveguide. An optional lens 902 may be used to couple the beams into the optical fiber 900. As shown in FIG. 9, the n laser beams may be combined, for example, by one of the embodiments for beam positioning and combining described above, or any combination of the embodiments described above and coupled into an optical fiber or waveguide. Both the coupling optics and fiber or waveguide may be located inside the temperature controlled enclosure and hard-mounted to the enclosure's temperature controlled base plate 901.

Figure 10:
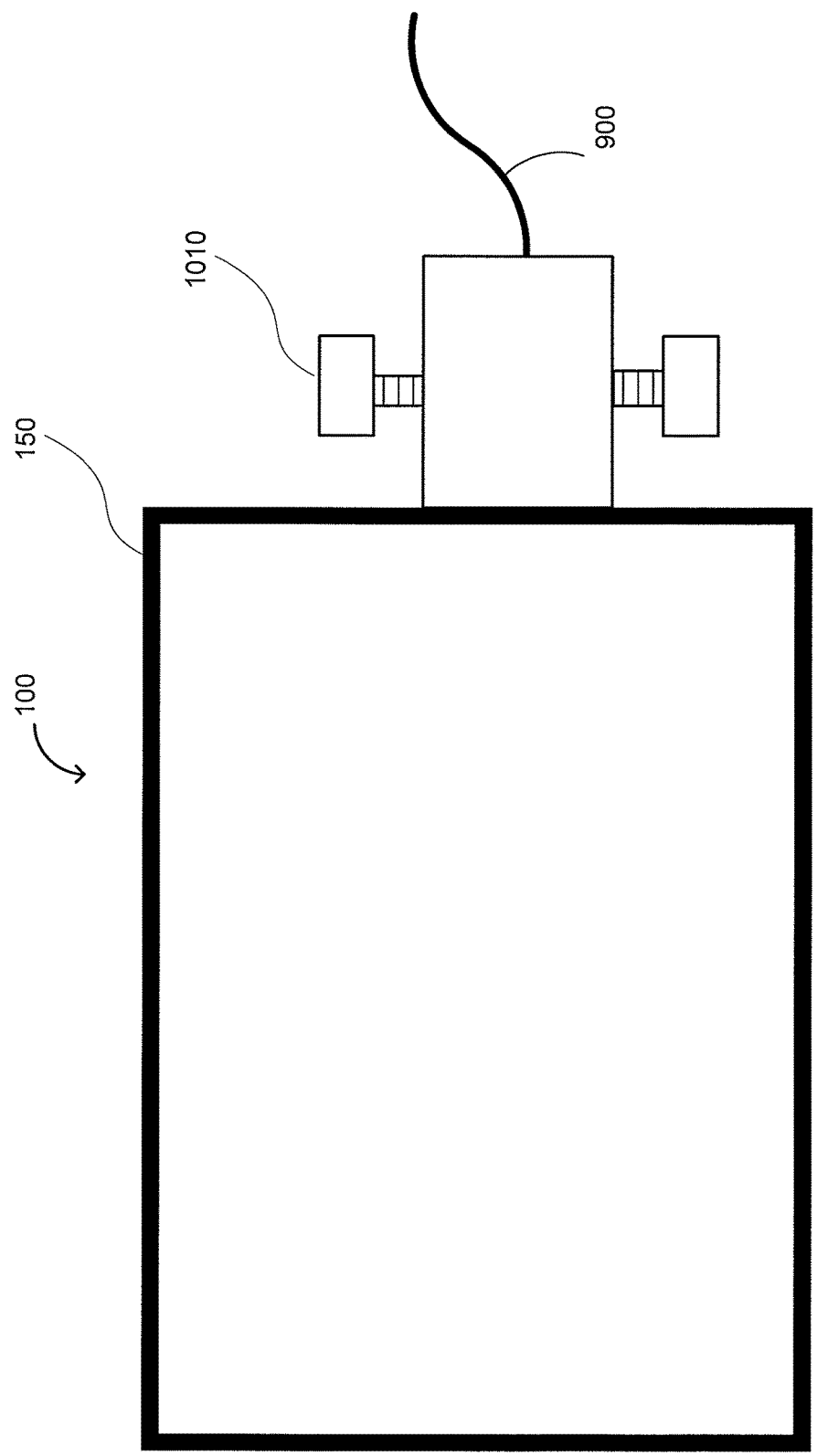
FIG. 10 depicts an example embodiment of a multi-laser system in which the target object comprises an adjuster mount.

FIG. 10 depicts an example embodiment of a multi-laser system in which the target object 1100 comprises an adjuster mount 1010. This adjuster mount may be configured to receive an optical fiber 900. Fiber optic coupling mounts are commercially available. In various embodiments, the fiber optic coupling mounts may comprise coupling optics mounted one focal length away from the optical fiber input with the optical axis of the coupling optics co-linear with a beam that would be emitted from the optical fiber. The coupling optics and optical fiber are mounted in a metal housing (e.g., a cylindrical housing) so that the alignment between the coupling optics and optical fiber input is maintained. This component may be a coupler/collimator assembly. In some embodiments, the mounts may comprise coupling optics and fiber in a metal housing. The coupler/collimator assembly is inserted into a positioning mount which is attached to the temperature controlled enclosure. For polarization maintaining fibers the coupler/collimator assembly and positioning mounts may be keyed so as to provide registration between the polarization axis of the laser beams and the polarization axis of the optical fiber. The positioning mount may be made of metal. The mount has mechanical adjusters that allow the pitch, yaw and lateral position of the coupler/collimator assembly to be moved relative to the input laser beams to optimize the amount of light coupled into the optical fiber. As shown in FIG. 10, the n laser beams may be combined, for example, by one of the embodiments for beam positioning and combining described above, or any combination of the embodiments described above and coupled into the adjustor mount or an optical element such as an optical fiber coupled to the adjuster mount. The optical fiber, coupling optics and coupling optimization hardware may be mounted at least partially on the outside of the temperature controlled enclosure.

Figure 11A:
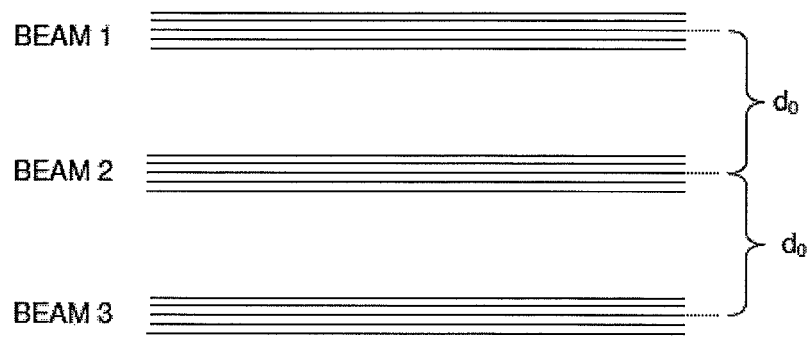
FIGS. 11A-11N depict example spatial arrangements of laser beams in multi-laser systems.
Figure 11B:
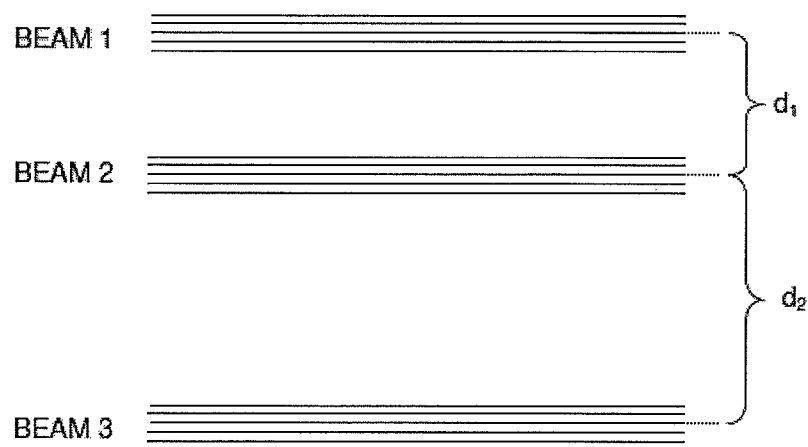
Figure 11C:
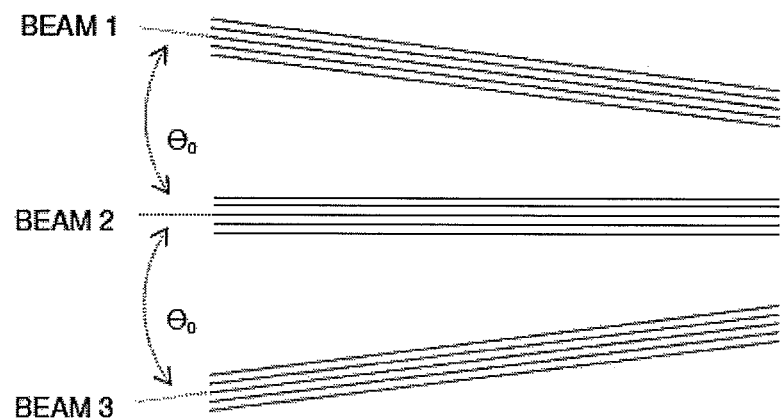
Figure 11D:
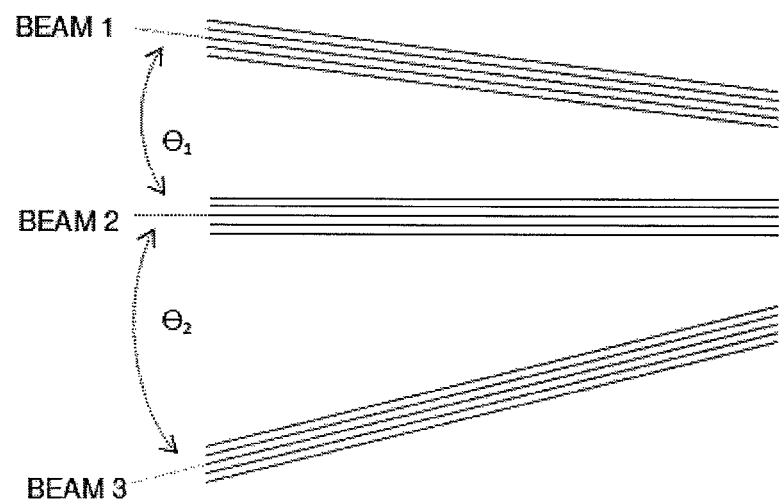
Figure 11E:
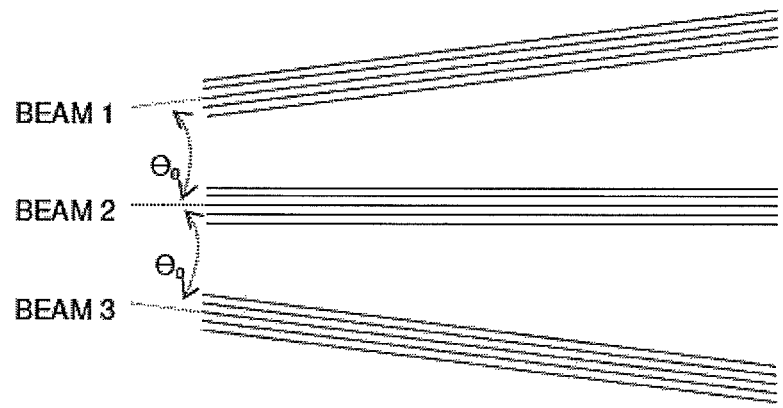
Figure 11F:
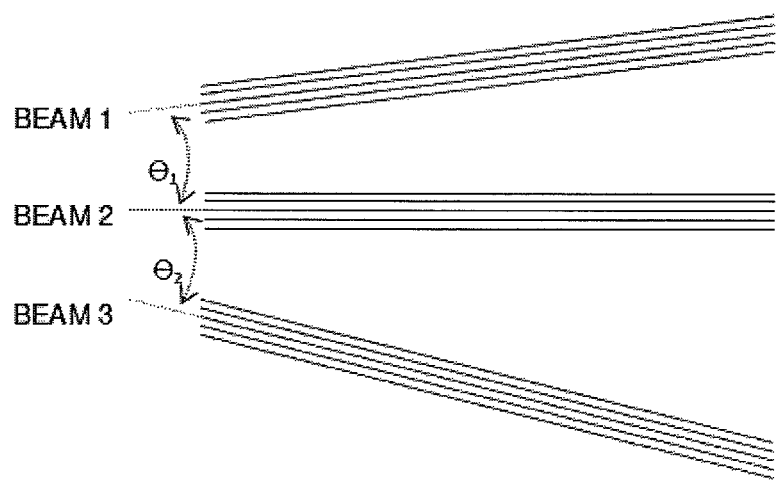
Figure 11G:
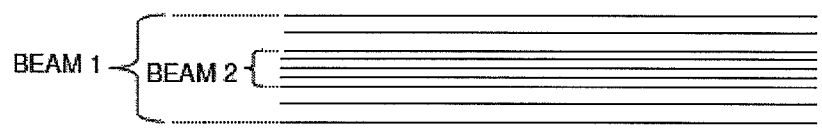
Figure 11H:
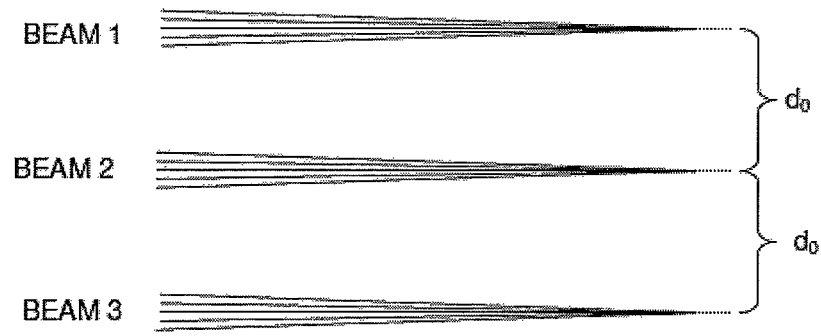
Figure 11I:
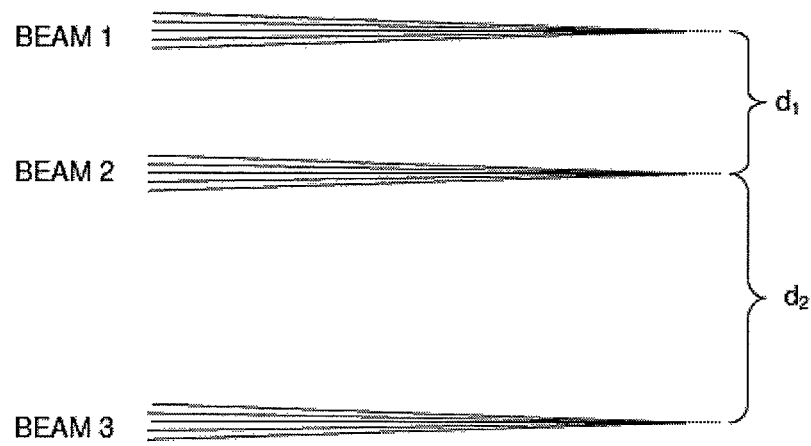
Figure 11J:
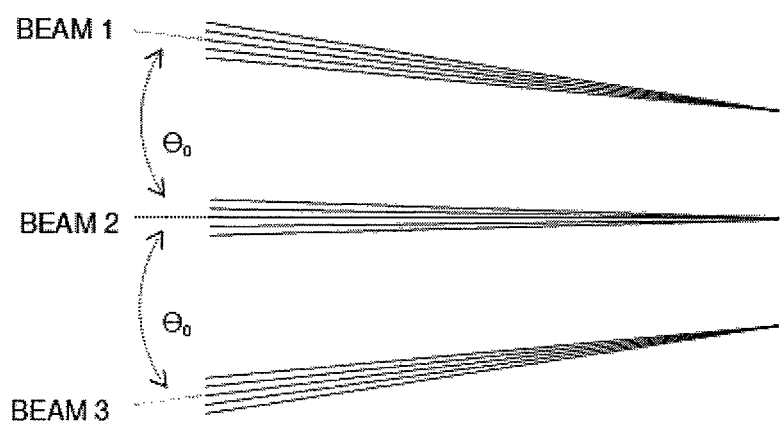
Figure 11K:
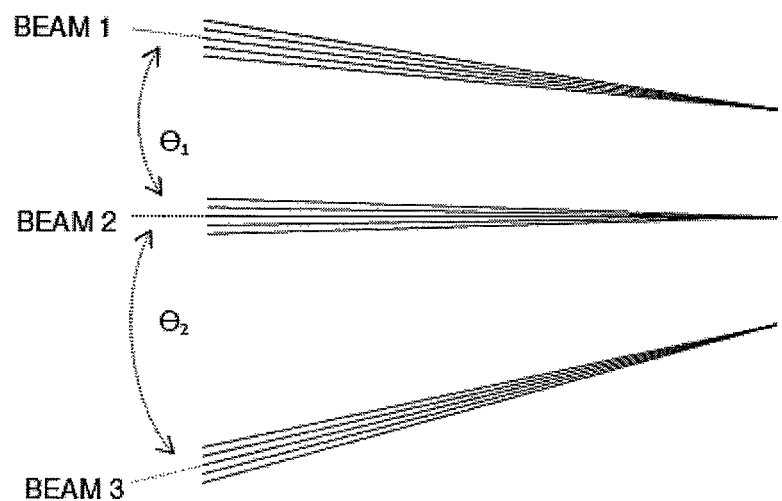
Figure 11L:
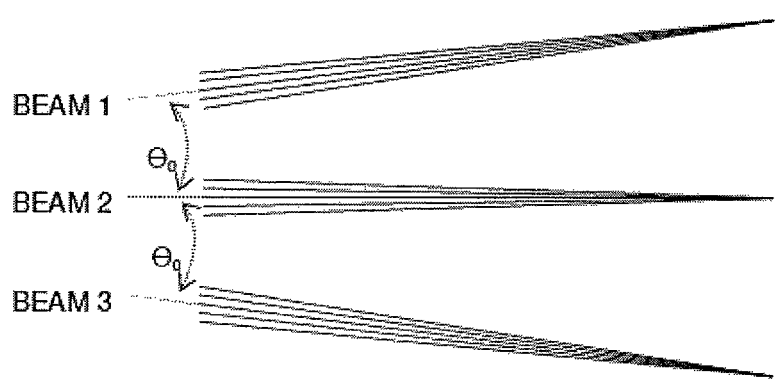
Figure 11M:
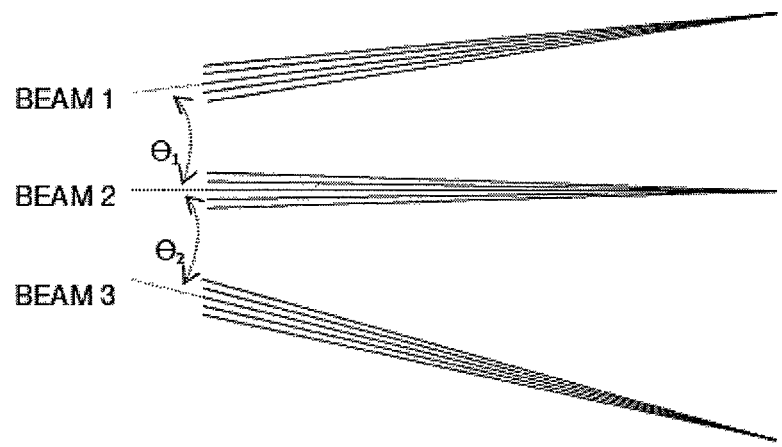
Figure 11N:
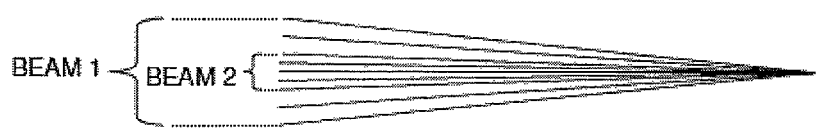

FIGS. 11A-11N depict example types and spatial arrangements of laser beams in multi-laser systems. The specific desired type and spatial arrangement of the laser beams may be application specific. The laser beams themselves may be collimated or focused. In some applications, however, it may be desirable to focus the laser beam in order to create small spot sizes at the target object and, hence, to increase power density or brightness on the target object. Accordingly, laser beams that are collimated or focused beams may be used. A plurality of collimated or a plurality of focused beams may be substantially co-linear to one another at the target object. The plurality of beams may alternatively be substantially parallel to one another but spaced apart from each other, or converging towards each other, or diverging away from one another at the target object. In some embodiments, the plurality of parallel beams may have identical beam separations (such as a substantially constant separation $d_0$) at the target object, or different beam separations (such as separations $d_1, d_2, \ldots$) at the target object. In some embodiments, the plurality of converging or diverging beams may have identical angular separations (such as a substantially constant separation $\theta_0$) at the target object, or different angular separations (such as separations $\theta_1, \theta_2, \ldots$) at the target object. In some embodiments, the angular separation may be less than about 5°.

Some example spatial arrangements of laser beams are depicted in FIGS. 11A-11N.

FIG. 11A depicts parallel collimated beams with identical beam separations, $d_0$.

FIG. 11B depicts parallel collimated beams with different beam separations, $d_1$ and $d_2$.

FIG. 11C depicts converging collimated beams with identical angular separations, $\theta_0$.

FIG. 11D depicts converging collimated beams with different angular separations, $\theta_1$ and $\theta_2$.

FIG. 11E depicts diverging collimated beams with identical angular separations, $\theta_0$.

FIG. 11F depicts diverging collimated beams with different angular separations, $\theta_1$ and $\theta_2$.

FIG. 11G depicts co-linear collimated beams.

FIG. 11H depicts parallel focused beams with identical beam separations, $d_0$.

FIG. 11I depicts parallel focused beams with different beam separations, $d_1$ and $d_2$.

FIG. 11J depicts converging focused beams with identical angular separations, $\theta_0$.

FIG. 11K depicts converging focused beams with different angular separations, $\theta_1$ and $\theta_2$.

FIG. 11L depicts diverging focused beams with identical angular separations, $\theta_0$.

FIG. 11M depicts diverging focused beams with different angular separations, $\theta_1$ and $\theta_2$.

FIG. 11N depicts co-linear focused beams.

Configurations other than those described herein are possible. The structures, devices, systems, and methods may include additional components, features, and steps and any of these components, features, and steps may be excluded and may or may not be replaced with others. The arrangements may be different. Reference throughout this specification to "some embodiments," "certain embodiments," or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Although the inventions presented herein have been disclosed in the context of certain preferred embodiments and examples, it will be understood by those skilled in the art that the inventions extend beyond the specifically disclosed embodiments to other alternative embodiments and/or uses of the inventions and obvious modifications and equivalents thereof. Thus, it is intended that the scope of the inventions herein disclosed should not be limited by the particular embodiments described above.

Part II

This application incorporates herein by reference in their entirety U.S. Patent Application Publication 2009/0257054 and corresponding U.S. patent application Ser. No. 12/418,494, filed Apr. 3, 2009 and titled "Compact, Thermally Stable Fiber-Optic Array Mountable to Flow Cell", as well as U.S. Provisional Application No. 61/042,640, filed Apr. 4, 2008.

Embodiments of the inventions will now be described with reference to the accompanying figures. Although certain preferred embodiments and examples are disclosed herein, inventive subject matter extends beyond the specifically disclosed embodiments to other alternative embodiments and/or uses of the inventions, and to modifications and equivalents thereof. Thus, the scope of the inventions herein disclosed is not limited by any of the particular embodiments described below. For example, in any method or process disclosed herein, the acts or operations of the method or process may be performed in any suitable sequence and are not necessarily limited to any particular disclosed sequence.

For purposes of contrasting various embodiments with the prior art, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 12:
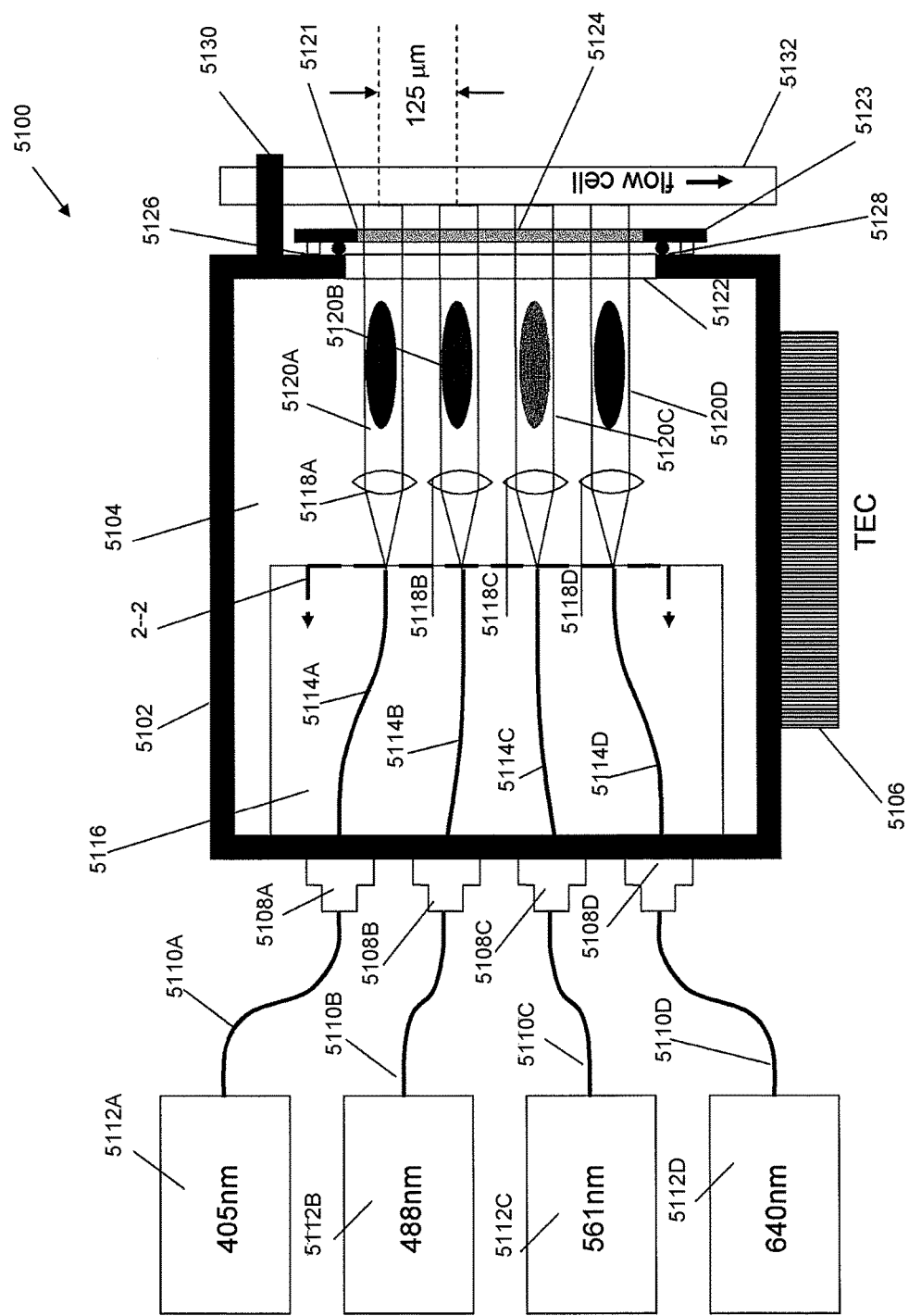
FIG. 12 schematically shows an optical system that can be used to direct light to samples for performing optical measurements such as laser-induced fluorescence and spectroscopic analysis.

FIG. 12 schematically shows an optical system 5100 that can be used to direct light to a sample for performing optical measurements such as laser-induce fluorescence and spectroscopic analysis. The optical system 5100 can include a housing 5102 enclosing an interior chamber 5104. The housing 5102 can be made of a thermally conductive material. The thermally conductive material can have a thermal conductivity between about 50 W/(m-K) and about 2000 W/(m-K). For example, the thermally conductive material may be copper which has a thermal conductivity of about 380 W/(m-K). A variety of thermally conductive metals can be used (e.g., copper or aluminum), as well as thermally conductive non-metals (e.g., ceramics or epoxy). The thermally conductive material can be used to form the entire housing, or merely a portion thereof. For example, substantially thermally conductive material can be used to form the top, the bottom, or any number of the sides of the housing 5102, or any combination thereof. In some embodiments, a majority of the housing 5102 is made of the substantially thermally conductive material. In some embodiments, only a relatively small portion of the housing 5102 is made of the substantially thermally conductive material. In some embodiments, a substantial portion of the housing 5102 is made of the substantially thermally conductive material. In some embodiments, multiple substantially thermally conductive materials can be used, with some areas of the housing 5102 being more thermally conductive than others.

In some of the embodiments discussed above, the housing is hermetically sealed from the ambient air. Thus, the interior chamber 5104 is isolated from air currents which can cause temperature variation, and the internal optical elements are protected from external contaminants. In some embodiments a getter (not shown) is located inside interior chamber 5104 which can reduce contaminant particles or chemical species. Additional, a desiccant (not shown) can be positioned inside the interior chamber 5104 to reduce moisture.

A thermoelectric controller 5106 can be thermally coupled to the housing 5102. The thermoelectric controller 5106 can include one or more temperature sensors (not shown) (e.g., thermistors) to measure the temperature of the housing 5102 and/or the temperature of the interior chamber 5104, and a heat transfer system (not shown) for removing heat from or adding heat to the housing 5102 in order to maintain a substantially constant temperature in the housing or in the interior chamber. In some embodiments, the thermoelectric controller 5106 can include a cooler for removing heat (e.g., heat resulting from operation of the optical system). In some embodiments, the thermoelectric controller 106 can include a heater for heating the housing 5102 and internal chamber 5104. In some embodiments, the heater can be used to maintain the internal chamber 5104 at a temperature above the anticipated highest ambient temperature. In some embodiments, the thermoelectric controller 5106 can include a thermoelectric cooler (TEC). The heat transfer system can be coupled directly to the housing 5102 and to the cooler and/or heater (e.g. TEC). In some embodiments, the temperature can be held within held within ±1° C., ±2° C., ±3° C., ±5° C., etc. of the target temperature. In some embodiments, the temperature of the interior chamber 5104 is between 15° C. and 45° C.

In some embodiments, the housing is compact. For example, the housing may be a size of less than 10 cubic inches. The relatively small size of the volume allows for rapid adjustment of temperature in response to variations in the ambient temperature and thus more precise control of the temperature in the internal chamber 5104.

The optical system 5100 can include a number of optical input ports 5108A-5108D. Although the embodiment shown in FIG. 12 includes four optical input ports, a different number of optical input ports can be used. In some embodiments, the optical input ports 5108A-5108D can be secured and hermetically sealed into respective apertures formed in the housing 5102, and can engage optical fibers 5110A-5110D. A variety of fiber connectors can be used, such as screw-type optical fiber connectors (e.g., an FC connector), snap-type fiber connectors, or other fiber connectors known in the art or yet to be devised. In some embodiments, the optical input ports 5108A-5108D include an angle-polished fiber connector (e.g., an FC/APC connector). In some embodiments, at least a portion of the optical input ports 5108A-5108D, such as the threading of a screw-type connector, can be integrally formed as part of the housing 5102. The optical fibers 5110A-5110D include fiber connectors (not shown) configured to securely and precisely mate with the optical input ports 5108A-5108D so that light can be efficiently transferred from the optical fibers 5110A-5110D to a plurality of optical fibers 5114A-5114D within the internal chamber 5104. In some embodiments, the optical fibers 5110A-5110D are single mode optical fibers. Highly polarized light can be injected into the optical fibers 5110A-5110D (e.g., from a diode laser), and in some applications it can be advantageous to preserve the polarization of the light. Accordingly, polarization-maintaining optical fibers can be used. In some embodiments different types of optical fibers can be connected to different optical input ports 5108A-5108D Likewise, in some embodiments, the different optical input ports 5108A-5108D can comprise different types of optical connectors.

The optical fibers 5110A-5110D can be coupled to laser light sources 5112A-5112D. Although the embodiment shown in FIG. 12 includes four lasers, a different number of lasers can be used. The lasers 5112A-5112D can include a variety of different laser types and can provide light of a variety of different wavelengths. The optical system 5100 shown in FIG. 12 includes a 405 nm laser, a 488 nm laser, a 561 nm laser, and a 640 nm laser, but other common wavelengths of laser light can be used (e.g., light having a wavelength of 440 nm, 635 nm, or 375 nm). The lasers 5112A-5112D can be diode lasers, diode-pumped solid state lasers, frequency doubled lasers, or other laser types that produce light useful for example in laser-induced fluorescence and spectroscopic analysis. Although FIG. 12 shows the lasers 5112A-5112D connected to the optical input ports 5108A-5108D via the optical fibers 5110A-5110D, in some embodiments the optical fibers 5110A-5110D and the lasers 5112A-5112D can be disconnected from the optical input ports 5108A-5108D by the user so that other lasers can be interchangeably connected to the optical system 5100. Thus, the optical system 5100 is a versatile tool which a user can easily modify to utilize a wide variety of lasers without difficult and time consuming adjustments.

The optical system 5100 can include a plurality of optical fibers 5114A-5114D contained within the internal chamber 5104. The optical fibers 5114A-5114D can be optically coupled to the optical input ports 5108A-5108D so that they receive light from the optical input ports 5108A-5108D and direct the light into the internal chamber 5104. In some embodiments, the cores of the optical fibers 5114A-5114D can be exposed by optical input ports 5108A-5108D so that the cores of the optical fibers 5110A-5110D can contact the cores of the optical fibers 5114A-5114D directly or come in substantial proximity to the cores of optical fibers 5114A-5114D. As with the optical fibers 5110A-5110D discussed above, the optical fibers 5114A-5114D can be single mode optical fibers and can be polarization-maintaining optical fibers.

In some embodiments, the optical system can include a fiber support structure 5116 that is configured to change the pitch of the optical fibers 5114A-5114D, bringing the output ends closer together than the input ends. For example, the optical input ports 5108A-5108D can be spaced about 10 to 20 millimeters or more apart from each other, so that the user can conveniently connect and disconnect optical fibers. The input ends of the optical fibers 5114A-5114D, which are coupled to the optical input ports 5108A-5108D, can be similarly distributed for example about 10 to 20 millimeters or more apart. The fiber support structure 5116 can have grooves (e.g., V-grooves) defining generally converging pathways, and the optical fibers 5114A-5114D can be secured in the grooves by a top-plate positioned over the grooves or by an adhesive. In some embodiments, the V-grooves can be configured to precisely hold the fibers. In some embodiments, silicon V-grooves manufactured using silicon processing techniques (e.g., etching, photoresists, etc.) can be used to secure the optical fibers 5114A-5114D. Grooves, holes, or slots for supporting the optical fibers 5114A-5114D may be formed in a support material (e.g., aluminum) by a machining process, such as electrical discharge machining (EDM). The fiber support structure 5116 can be configured to bring the optical fibers 5114A-5114D closer together so that when the light is output from the optical fibers 5114A-5114D the light is emitted from nearby locations (e.g., about 110 to 140 microns apart, and more specifically, about 125 microns apart, although other distances are possible).

Figure 13:
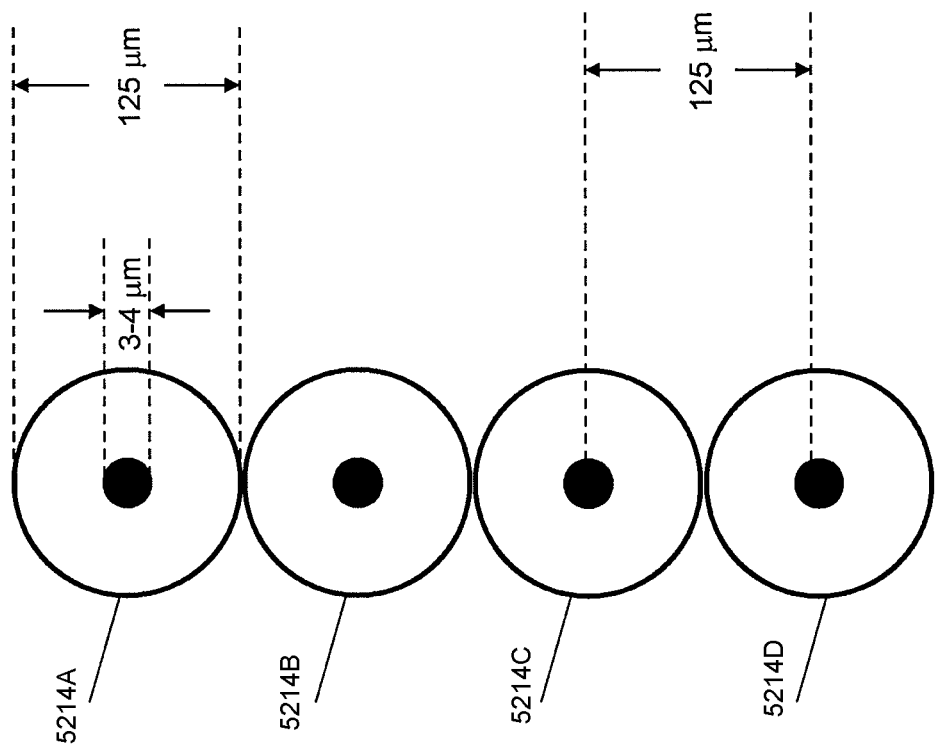
FIG. 13 is a cross-sectional view of an embodiment of an optical fiber array.

FIG. 13 is a cross-sectional view (shown from the position indicated by line 2-2 in FIG. 12) of an embodiment of optical fibers 5214A-5214D. As shown in FIG. 13, the optical fibers 5214A-5214D can be single mode optical fibers that have output ends measuring about 125 microns in total diameter, with the core measuring about 3-4 microns in diameter. Other sizes can be used. In the embodiment shown in FIG. 13, the output ends of the optical fibers 5214A-5214D are brought close together so that the cladding of one optical fiber is adjacent to the cladding of the next optical fiber, and light is emitted by the cores of optical fibers 5214A-5214D at locations which have centers positioned about 125 microns apart. Other arrangements are possible. It should be noted that the drawings herein are not drawn to scale (unless otherwise indicated), and in some embodiments the tapering of the optical fibers provided by the fiber support structure 5116 can be much more pronounced than is indicated in FIG. 12.

In some embodiments, the fiber support structure 5116 does not bring the optical fibers 5114A-5114D significantly closer together, but merely orients the optical fibers 5114A-5114D so that light is emitted in a direction that causes the light to contact the optical elements 5118A-5118D at a suitable angle. Other variations are possible.

Although the embodiment illustrated by FIG. 12 includes optical fibers 5114A-5114D, other types of waveguides can be used (e.g., planar waveguides). In some embodiments, the waveguides can be rigid waveguides. The waveguides can include curved and/or linear paths. The waveguides can include a taper to otherwise have an output end with outputs closer together than inputs at an input end, similar to the embodiment shown in FIG. 12. In some embodiments, an integrated waveguide chip is used.

Although the embodiment illustrated in FIG. 12 shows the optical fibers 5110A-5110D and the optical fibers 5114A-5114D as being different sets of optical fibers, in some embodiments, the optical system can include a single set of optical fibers that extend through the housing and couple to the laser light sources. In these embodiments, the optical input ports 5108A-5108D can be apertures in the housing 5102 through which the optical fibers can pass. In some embodiments, the apertures can include seals formed around the optical fibers to hermetically seal the interior chamber. Epoxy may be used to provide such a hermetic seal, although other approaches can be used. The optical fibers can include optical connectors (e.g., FC/APC connectors) configured to removably couple with the laser light sources 5112A-5112D.

The optical fibers 5114A-5114D (or waveguides) emit light toward a plurality of optical elements 5118A-5118D, which convert the light into beams of light 5120A-5120D having a suitable shape and/or size. The optical elements 5118A-5118D can be lenses, and can be separate individual lenses, or they can be conjoined forming a lens array. In some embodiments, optical elements 5118A-5118D can be compact microlenses. In some embodiments, a single lens can be used to produce each of the light beams 5120A-5120D. In some applications, it can be advantageous to produce elongated beams of light, such as beams of light having a generally elliptical cross-sectional shape (shown schematically in FIG. 12). For example, the beams of light 5120A-5120D can have a generally Gaussian profile, so that when illuminating a flow cell, the intensity of the light illuminating the center of the flow cell is significantly greater than the intensity of the light illuminating the peripheral edges of the flow cell. Accordingly, the beams of light 5120A-5120D can be elongated (e.g., elliptical) beams, so that the relatively high intensity center regions of the light beams extend across the entire width of the flow cell, while the relatively low intensity outer regions of the light beams do not strike the flow cell. By using an elongated (e.g., elliptical) beam of light, a more uniform lateral distribution of light across the narrow width of the flow cell can be achieved while illuminating a relatively small longitudinal area along the length of the flow cell and maintaining high light intensity. In some embodiments, the elliptical light beams can have a substantially elliptical cross sectional shape that measure about 5 to 15 microns in one direction and 55 to 100 microns in the other direction, or more specifically about 10 microns in one direction and about 70 microns in the other direction. Light beams of other shapes and sizes can be used. To produce elongated (e.g., elliptical) beams of light 5120A-5120D, optical elements 5118A-5118D can be anamorphic lenses (e.g., cylindrical lenses) or Powell lenses (Gaussian to flat-top transformers). In one embodiment, optical elements 5118A-5118D can be an anamorphic microlens array. In some embodiments, the optical elements 5118A-5118D can be achromatic lenses. In some embodiments, optical elements 5118A-5118D can be refractive and/or diffractive optical elements used to produce the elongated beams of light 5120A-5120D. In some embodiments, the optical elements 5118A-5119D can be located adjacent to the output ends of the optical fibers 5114A-5114D.

The optical system 5100 can include an output window 5121 that allows the beams of light 5120A-5120D to exit the internal chamber 5104. In some embodiments, the housing 5102 includes an aperture 5122 in a wall thereof and the output window 5121 comprises a transparent window pane 5124, positioned over the aperture 5122. The window pane 5124 can be made from glass or acrylic or a variety of other transparent materials (e.g., plastic). The aperture 5122 and window pane 5124 can assume a variety of shapes, but in some embodiments they are circular or elliptical. The window 5121 can be attached to the housing 5102 by a plurality of fasteners such as bolts 5126. In FIG. 12, only two bolts 5126 are shown in the cross-sectional view, but in some embodiments, additional bolts can be positioned along the edges of the window 5121. In some embodiments, the window 5121 can include a flange 5123 for mounting the window. The flange 5123 may have a plurality of through holes through which fasteners (e.g., bolts 5126) can pass to secure the window 5121 to the housing 5102. A seal 5128 (e.g., an O-ring) can be positioned between the housing 5102 and the window 5121 (e.g., the flange 5123). The bolts 5126 can be tightened, causing the O-ring 5128 to be compressed between the housing 5102 and the window 5121. In some embodiments, the O-ring 5128 produces a hermetic seal. Other approaches can be used to fasten the window 5121 to the housing 5102. For example, the window 5121 can be disposed in recess on the outer or inner surface of the housing 5102, or can be embedded into the housing 5102, or can be mounted onto the inside of the housing 5102. The window 5121 can be secured to the housing 5102 by an adhesive, epoxy, or cement.

Although the embodiment shown in FIG. 12 shows a single output window, multiple output windows can be used. For example, each beam of light 5120A-5120D can exit the interior chamber 5304 via a respective output window. In some embodiments, it is desirable that as much as possible of at least the inner surface area of the housing 5102 comprise the thermally conductive material, to better achieve temperature uniformity. Accordingly, the output windows can be separated by thermally conductive material and can cover only as much area as necessary to allow light beams 5120A-5120D to leave the interior chamber 5104. However, in some embodiments a single output window is easier and less expensive to construct.

In some embodiments, the optical elements (e.g., lenses or lens) that produce the light beams 5120A-5120D can be formed as part of the output window (or windows). For example, the window pane 5124 can include at least one curved surface to produce optical power, which can be configured to produce the plurality of light beams 5120A-5120D having a desired shape and/or size. The window pane 5124 can comprise a lens array such as a microlens array, and can be anamorphic as discussed above.

The optical system 5100 can include a flow cell connector 5130 that is attached to the housing, and the flow cell connector 5130 is configured to secure a flow cell 5132 so that it intersects the beams of light 5120A-5120D. In some embodiments, the flow cell connector 5130 can permanently attach the flow cell 5132 to the housing 5102. However, in some embodiments, the flow cell connector 5130 can allow the flow cell 5132 to be removably attached to the housing 5102. In some embodiments, the flow cell connector 5130 can be compatible with multiple types and/or sizes of flow cells. For example, the flow cell connector can include a clip, a friction or pressure fit coupling, a threaded portion configured to receive a corresponding threaded portion of the flow cell 5132, or a variety of other connectors known in the art or yet to be devised. The flow cell 5132 can be a capillary flow cell, and at least part of the flow cell can comprise a transparent material (e.g., glass) that allows the light beams 5120A-5120D to enter the flow cell 5132 and interact with a sample fluid contained within the flow cell 5132. In one embodiment, the flow cell 5132 can be a thin hollow tube, forming a flow path that has a diameter of about 10 microns. Other flow cell types and/or sizes can be used, and the flow cell 5132 can be oriented differently than as shown in FIG. 12. In some embodiments, the beams of light 5120A-5120D strike the flow cell over areas centered about 110 to 140 microns apart from each other, and in some embodiments, 125 microns apart from each other. For some forms of optical measurements, it is desirable for the laser light to strike the flow cell at specific locations (e.g., areas spaced about 125 microns apart). In some embodiments, the optical system 5100 mounts the optical fibers to automatically direct the light from the laser light sources 5112A-

5112D to the desired locations of the flow cell 5132 without requiring the user to manipulate any mirrors or wavelength selective elements such as dichroic mirrors or optical elements.

The optical system 5100 can be compatible with various types of optical (e.g., spectroscopic) analysis. For example, for laser-induced fluorescence spectroscopy, a fluorescent dye designed to bond with an analyte can be introduced into the fluid sample. When the fluid sample passes through the beams of light 5120A-5120D, the fluorescent dye absorbs photons and emits photons that have a longer wavelength (less energy). By using photodetectors such as a photomultiplier tube (PMT) (not shown) to measure the amount of light that is emitted, the presence or concentration of the analyte in the sample fluid can be measured. For absorption spectroscopy, photodetectors (not shown) can be positioned on the side of the flow cell 5132 opposite the housing 5102 to determining the amount of light that is absorbed by the fluid sample. The optical system 5100 can also be compatible with other types of optical measurements or spectroscopic analysis.

Figure 14:
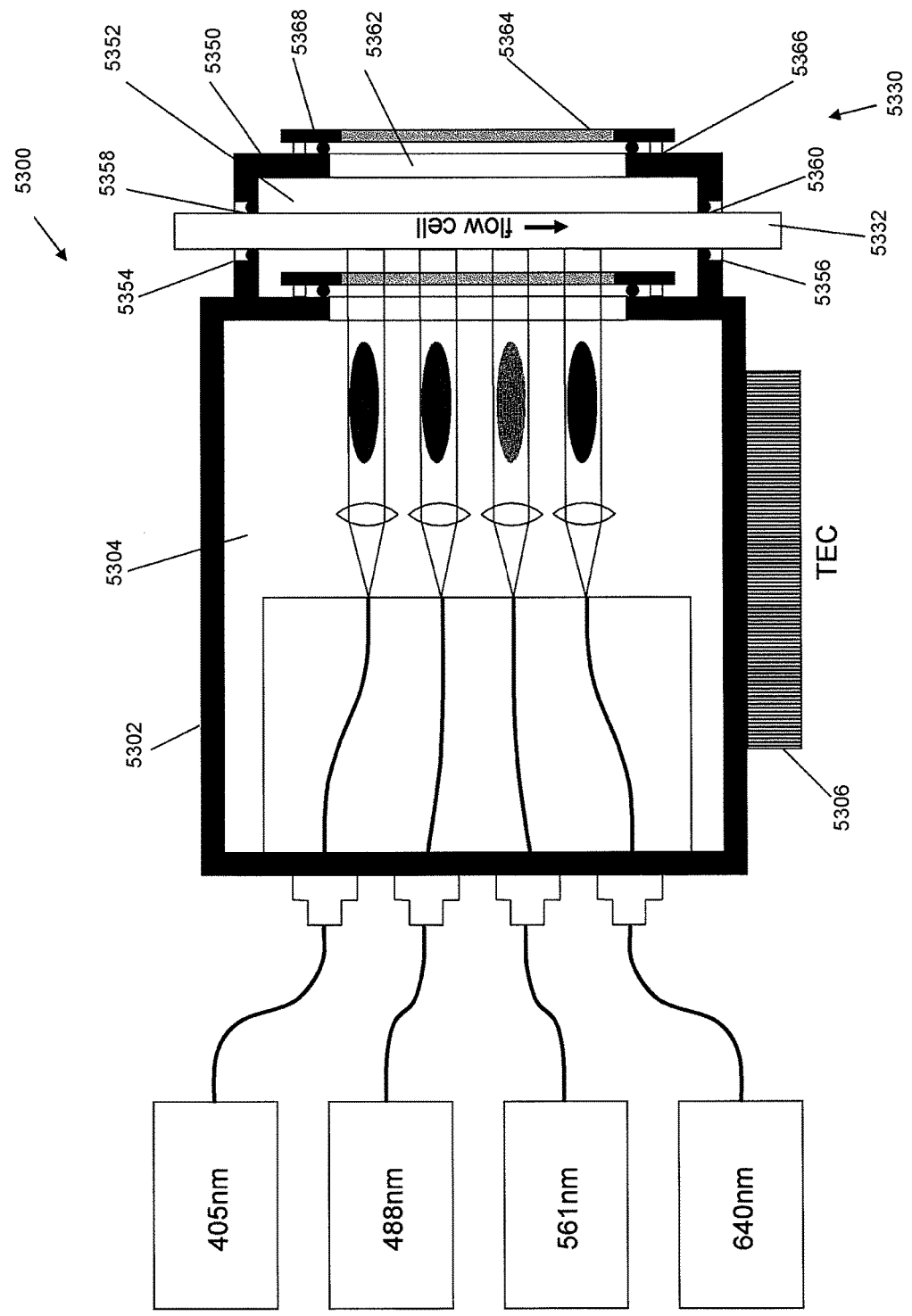
FIG. 14 schematically shows another optical system that can be used to direct light to samples for performing optical measurements such as laser-induced fluorescence and spectroscopic analysis.

FIG. 14 schematically shows an embodiment of an optical system 5300 that can be used to direct light for optical measurements (e.g., laser-induced fluorescence and spectroscopic analysis). The optical system 5300 is similar to optical system 5100 in some aspects, and similar elements are labeled with the same reference numerals used in FIG. 12 except that the numbers are increased by 200. The optical system 5300 can include a flow cell connector 5330 that comprises a thermally conductive auxiliary sample housing 5350 which encloses an interior chamber 5352. The flow cell connector 5330 can be configured to secure a flow cell 5332 so that it passes through the interior chamber 5352. For example, the sample housing 5350 can include two apertures 5354, 5356 and two flexible seals 5358, 5360, so that the flow cell 5332 can be slidably inserted through the apertures 5354, 5356 and held in place by friction against the flexible seals 5358, 5360. Alternatively, the sample housing 5350 can include a door allowing the sample housing 5350 to be opened and the flow cell 5332 to be placed inside. In various embodiments where the interior chamber 5352 of sample housing 5350 is hermetically sealed with respect to interior chamber 5304 of the main housing 5302, the interior chamber 5352 of the sample housing 5350 can be exposed to ambient air without exposing the components contained within interior chamber 5304 of the main housing 5302. Accordingly, the interior chamber 5352 of the sample housing 5350 can be exposed to ambient air when flow cell 5332 is removed and the seals 5358, 5360 may be excluded in some embodiments.

In some embodiments, the sample housing 5350 can be integrally formed as part of the main housing 5302 or can be thermally coupled to the main housing 5302 so that the thermoelectric controller 5306 regulates the temperature within the interior chamber 5352 of the sample housing 5350 as well as the interior chamber 5304 of the main housing 5302. In some applications it may be desirable to maintain the internal chamber 5352 of the sample housing 5352 enclosing the flow cell at a different temperature than the internal chamber 5304 of the main housing 5302, such as when a fluid sample is used that should be maintained at a different temperature than the interior chamber 5304 of the main housing 5302. Accordingly, in some embodiments, a second thermoelectric controller (not shown) can be thermally coupled to the sample housing 5350 and an insulating layer (not shown) can be positioned at the transition between the main housing 5302 and the sample housing 5350 so that the internal chamber 5352 of the sample housing 5350 can be maintained at a different temperature than the interior chamber 5304 of the main housing 5302.

The optical system 5300 can include a second output window for transmitting light out of the internal chamber 5352 of the sample housing 5350. The second output window can be similar to the output window described above, and cover an aperture 5362 covered with a transparent window pane 5364. The transparent window pane 5364 can be attached to the housing 5350 by bolts 5366 and sealed by a seal 5368. In some embodiments, the interior chamber 5352 of the sample housing 5350 is not hermetically sealed and the seal 5368 can therefore be a non-hermetic seal or can be omitted altogether.

Figure 15:
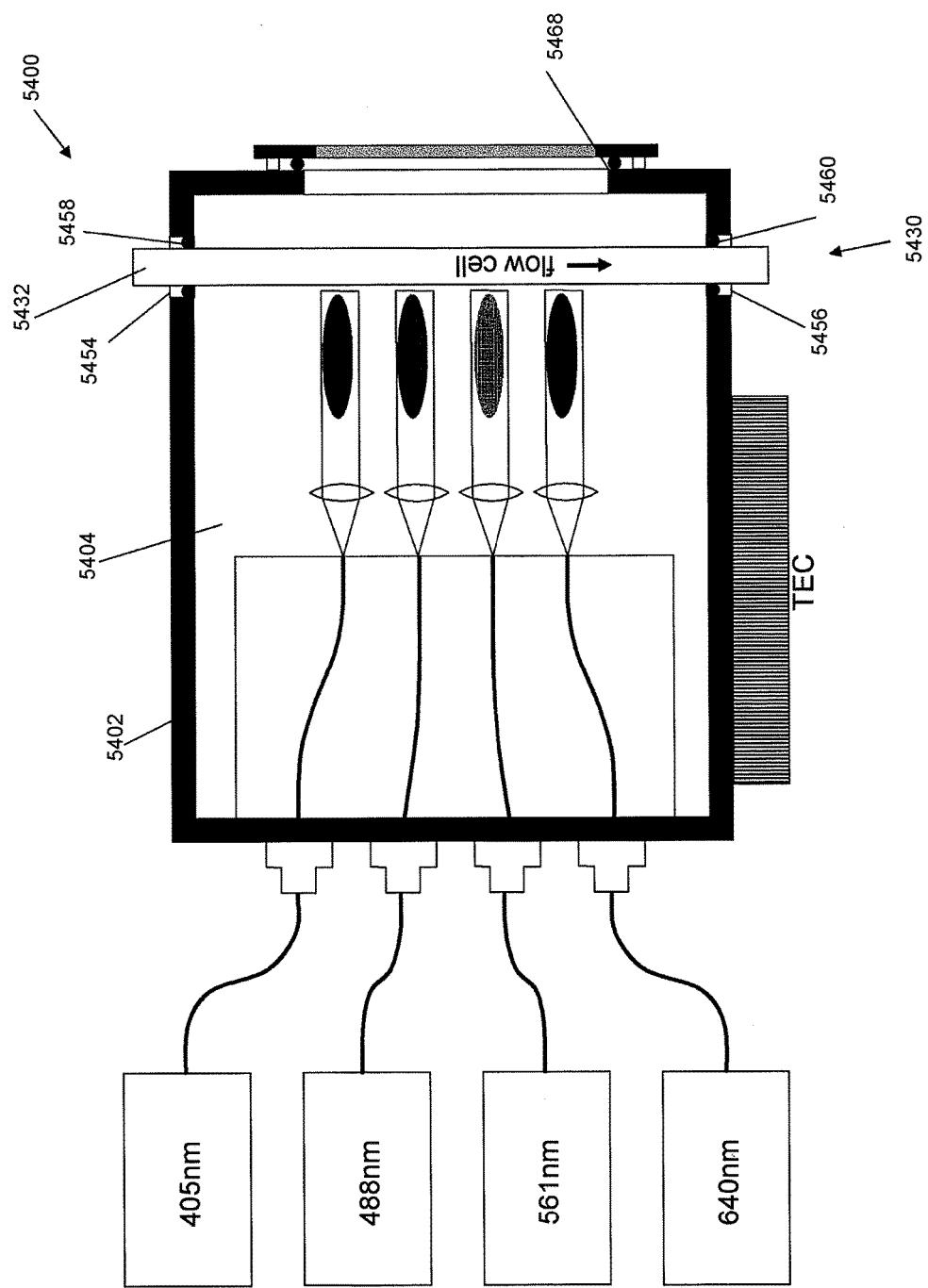
FIG. 15 schematically shows another optical system that can be used to direct light to samples for performing optical measurements such as laser-induced fluorescence and spectroscopic analysis.

FIG. 15 schematically shows an embodiment of an optical system 5400 that can be used to direct light for optical measurements such as laser-induce fluorescence and spectroscopic analysis. The optical system 5400 is similar to optical systems 5100 and 5300 in some aspects, and similar elements are labeled with the same reference numerals used in FIGS. 12 and 14 except that the numbers are increased by 200 and 100 respectively. Optical system 5400 can include a flow cell connector 5430 that attaches a flow cell 5432 to the housing 5402 so that the flow cell 5432 passes through the housing 5402. For example, the housing 5402 can comprise two apertures 5454, 5456 and two flexible seals 5458, 5460, so that the flow cell 5432 can be slidably inserted through the apertures 5454, 5456 and held in place by friction against the flexible seals 5458, 5460. Alternatively, the housing 5402 can include a door allowing the housing 5402 to be opened and the flow cell 5432 to be placed inside. In some embodiments, the interior chamber 5404 can be exposed to ambient air when flow cell 5432 is removed and the seals 5458, 5460 can be non-hermetic seals. Also, the seal 468 can be a non-hermetic seal or can be omitted altogether.

Part III

As noted above, U.S. Provisional Patent Application No. 62/133,241, filed Mar. 13, 2015, and U.S. Provisional Patent Application No. 62/135,137, filed Mar. 18, 2015, are incorporated herein by reference in their entireties, and the systems and methods described herein are also described therein. As described above, for example, with respect to FIG. 7, beam adjusters 504A-504N such as Risley prism pairs 705A-705N may be employed to adjust laser boresight and/or compensate for opto-mechanical angular errors. However, in various implementations, other components may be employed to adjust the laser boresight. For example, the beam adjusters 504A-504N of FIG. 5 can comprise a meniscus shaped optical element (e.g., a meniscus lens or meniscus window) to adjust boresight and/or to correct centration errors of one or more of the n laser beams. The meniscus shaped optical element can be tilted or translated (e.g., in x and/or y directions) with respect to the optical path to alter the angle of the laser beam. The meniscus shaped optical element is discussed in detail below with reference to FIG. 16(a).

Figure 16A:
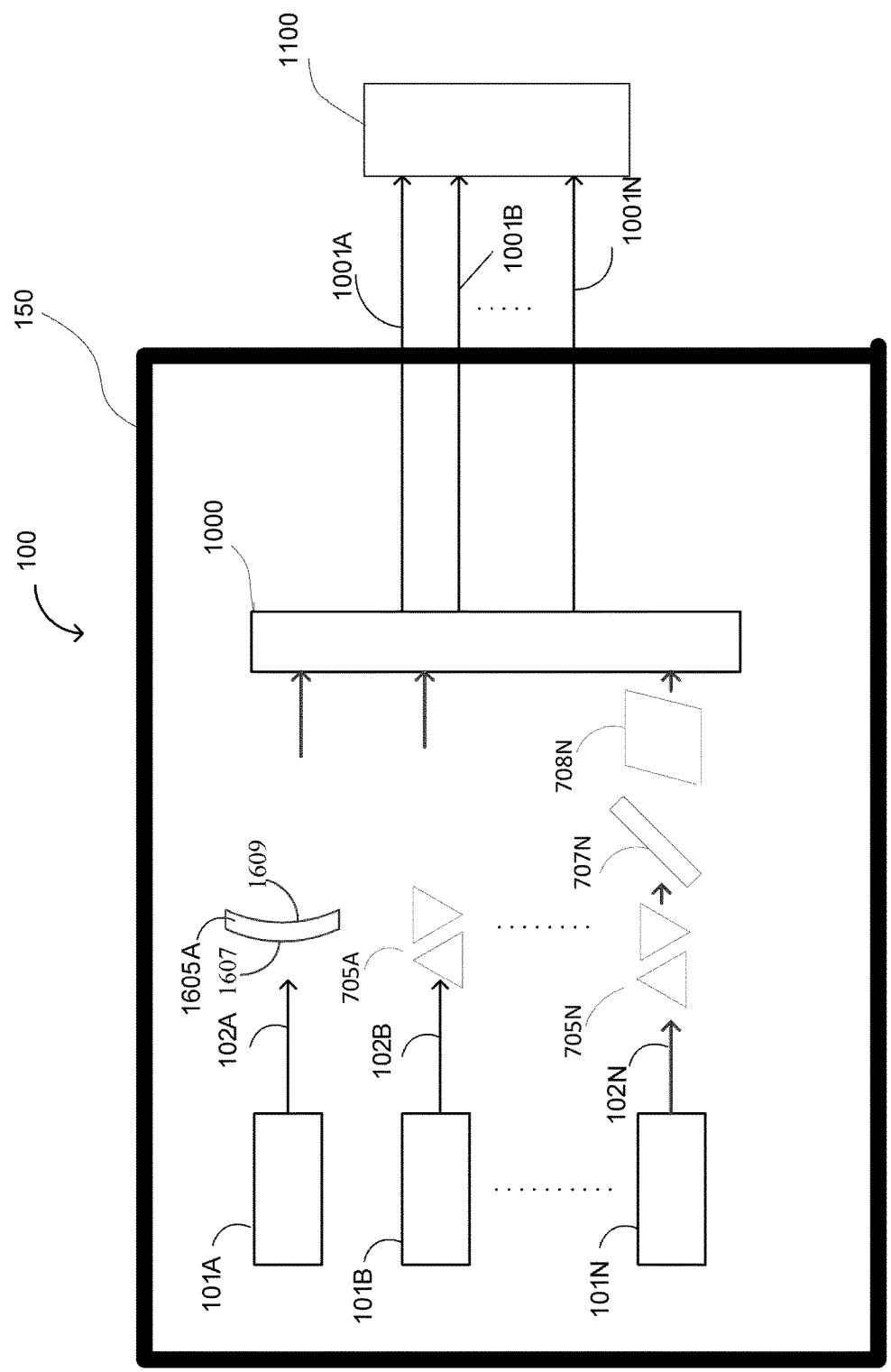
FIG. 16(*a*) illustrates an implementation of a multi-laser optical system including a plurality of laser devices 101A, 101B, . . . , 101N configured to emit light along a plurality of optical paths 102A, 102B, . . . , 102N respectively.

FIG. 16(a) illustrates an implementation of a multi-laser optical system including a plurality of laser devices 101A, 101B, . . . , 101N configured to emit light along a plurality of optical paths 102A, 102B, . . . , 102N respectively. A meniscus shaped optical element 1605A, is disposed in at least one of the optical paths 102A. It is conceived that all the optical paths 102A, 102B, . . . , 102N can include the meniscus shaped optical element. It is also conceived that one or more optical paths (e.g., optical paths 102B and 102N) can include Risley prism pairs similar to Risley prism pairs 705A-705N as shown in FIG. 7 or Risley prism pairs in combination with etalon plates similar to etalon plates 707A-707N and/or 708A-708N as shown in FIGS. 8A and 8B instead of the meniscus shaped optical element. It is also conceived that the meniscus shaped optical element can be disposed along with the Risley prism pairs and/or the etalon plates. For example, a meniscus shaped optical element and one or more etalon plates (e.g., orthogonally oriented tilted etalon plates for translating the beam in orthogonal x and y directions) can be disposed in the same optical path such that a beam from one of the laser devices passes through each of the meniscus shaped optical element and the one or more etalon plates.

FIG. 16(b) illustrates an implementation of a meniscus shaped optical element 1605A including a first curved surface 1607 configured to receive the incident laser beam and a second curved surface 1609 opposite the first curved surface 1607 configured to output the laser beam. The first curved surface 1607 and the second curved surface 1609 can be portions of a spherical surface. Alternately, the first curved surface 1607 and the second curved surfaces can be aspheric. The first and second curved surfaces can also be cylindrical surfaces and have different curvature in different directions (e.g., in x and y directions). In some embodiments, the first and second curved surfaces can have non-zero curvature in different directions (e.g., in x and y directions); for example, the first and second curved surfaces can be ellipsoidal curved surfaces or toroidal curved surfaces. The first and the second surface 1607 an 1609 can be associated with a radius of curvature or an aspheric equation. In various implementations, the first and the second surfaces can have almost identical surface characteristics. For example, the curvature, the surface sag, and/or the radius of curvature of the first and the second surface 1607 and 1609 can be identical. In various implementations, the radius of curvature of the first curved surface 1607 and the radius of curvature of the second curved surface 1609 can be approximately equal. In various implementations, the first and the second surface of the optical element 1605A can be shaped and sized identically at least sufficiently close such that the optical element 1605A has zero optical power. Additionally, the thickness of the optical element 1605A can also be shaped and sized identically at least sufficiently close such that the optical element 1605A has zero optical power. In other implementations, the surface characteristics of the first and the second surface of the optical element 1605A can deviate slightly from each other such that the optical element 1605A has almost no optical power. For example, the meniscus optical element may have a optical power larger than zero but less than 2 diopter, less than 1 diopter, or less than 0.1 diopter, or any ranges therebetween. As illustrated, the first surface 1607 is convex and the second surface 1609 is concave. However, it is conceived that the first surface 1607 is concave and the second surface 1609 is convex. For example, the first curved surface 1607 and the second curved surface 1609 may have a radii of curvature larger or equal to 10 mm and less than or equal to 1000 mm. Values outside these ranges are also possible. Additionally, as another example, the optical element 1605A may have thickness greater than or equal to 2 mm and less than or equal to 20 mm. Values outside these ranges are also possible.

The first surface 1607 and the second surface 1609 is intersected by an optical axis 1611. The optical axis 1611 can pass through the center of curvature of the first surface 1607 and the center of curvature of the second surface 1609. Without any loss of generality, the optical axis 1611 can represent a principal axis of the optical element 1605A. Any ray of light that is incident along the optical axis 1611 will pass through the optical element without being deviated. The optical axis 1611 can intersect the first surface 1607 at a first vertex and the second surface 1609 at a second vertex. The optical element 1605A can be configured such that a length of a segment joining the first vertex and the second vertex is less than, greater than, or equal to the length of any other parallel segment, depending for example, on whether the meniscus lens is a positive meniscus lens (center thickness larger than edge thickness) or negative meniscus lens (with center thickness smaller then edge thickness). In various implementations, the thickness of the optical element 1605A can be measured along the optical axis and be equal to the length of the segment joining the first vertex and the second vertex. Various implementations of the optical element 1605A can be configured to be rotationally symmetric about the optical axis 1611.

In various embodiments, the optical element 1605A can be used to redirect optical beams. In various embodiments, an incoming light beam (e.g., an output of the laser 101A) is incident on the optical element, experiences refraction and redirection under Snell's Law, and exits the optical element. It should be noted that the incoming light beam may not experience any refraction and redirection if it is normally incident along the optical axis. In some configurations, the output beam may experience an elevation deviation without with respect to the input beam. In certain configurations of the optical element, it may also be possible to control the angle of deviation in the lateral (e.g., left or right) direction of the output beam. Therefore, the optical element 1605A can be used to direct a light beam at a variety of elevation angles and lateral angles (left or right versus up or down directions). Viewed from another perspective of another coordinate system, the optical element 1605A can be used to direct a light beam at a particular azimuth angle and a particular elevation. This is explained in further detail below.

The optical element 1605A can be configured to correct boresight errors of the laser beam output from the laser 101A along optical path 102A. The adjusted laser beam can be positioned and/or combined into a desired spatial arrangement with other laser beams output along optical paths 102B, . . . , 102N by the beam positioning/combining system 1000. In various embodiments, the errors in the laser boresight and opto-mechanical angular errors may be compensated for by tipping or tilting the optical element 1605A (adjusting the pitch and/or yaw of the optical element 1605A) with respect to the incident laser beam or the optical path and/or by adjusting the position of the optical element 1605A horizontally and/or vertically with respect to the incident laser beam or the optical path. For example, as discussed in detail below, in various implementations, the optical element 1605A can be tipped and/or tilted with respect to the optical path to compensate for errors in the boresight of the laser beam output. As another example, as discussed in detail below, in various implementations, the position of the optical element 1605A can be adjusted laterally vertically and/or horizontally with respect to the incident laser beam or the optical path to correct for boresight error in the incident laser beam. The thickness of the optical element 1605A along the optical axis and/or characteristics of the first and the second curved surface 1607 and 1609 (e.g., curvature, radius of curvature, apshericity) can be selected to provide a desired range of correction. In various elements, the thickness of the optical element 1605A along the optical axis and/or characteristics of the first and the second curved surface 1607 and 1609 (e.g., curvature, radius of curvature, apshericity) can be selected to provide a desired correction range, correction sensitivity and/or correction resolution.

FIG. 16(c-1) depicts a laser beam with 0 degree boresight error that is incident on an implementation of an optical element 1605A. The optical element 1605A is configured such that the incident beam of light passes through the optical element 1605A without being deviated such that the output laser beam also has 0 degree boresight error. In the illustrated implementation, the laser beam is incident along a direction parallel to the z-axis. The optical element 1605A is positioned such that the optical axis 1611 is along the z-axis and the first and the second surface of the optical element 1605A extend vertically and horizontally in the x and y directions.

FIG. 16(c-2) depicts a laser beam with about 1 degree boresight error that is incident on an implementation of an optical element 1605A. In other words, the incident laser beam can be at an angle of about 1 degree with respect to the z-axis. The optical element 1605A can be rotated with respect to the incident beam (e.g., about the x-axis, about the y-axis or about the x-axis and the y-axis) such that the incident laser beam is output from the optical element 1605A after refraction at the first surface 1607 and the second surface 1609 with a boresight error less than 1 degree (e.g., boresight error less than 0.5 degrees or a 0 degree boresight error). In the illustrated implementation, the optical element 1605A is rotated about the y-axis (or tipped) with respect to the x-axis by an angle of about 29.6 degrees to achieve 0 degree boresight error, as shown in FIG. 16(c-3). In various implementations, the thickness along the optical axis of the optical element 1605A, the surface characteristics (e.g., curvature, radius of curvature, surface sag, etc.) can be configured such that the optical element is tipped by a different amount to achieve the same amount of correction. For example, in various implementations, the optical element 1605A can be tipped by an angle between about 0 degrees and 30 degrees to correct the boresight error from about 0 degrees to a boresight error less than 0.05 degree or between about 0 degrees and 30 degrees to correct the boresight error from about 0 degrees to a boresight error less than 5 degrees. The sensitivity can thus range between about 0.0017 degrees/degree and 0.17 degrees/degree. The range of correction can range between 0 degrees and 0.05 degrees or between about 0 degrees and 5 degrees. Values outside these ranges are also possible.

FIG. 16(d-1) illustrates the variation in the boresight angle change expressed in radians (rad) versus the change in the angle of incidence (AoI). The AoI corresponds to the relative angle of incidence of the laser beam with respect to the meniscus optical element expressed in degrees for an implementation of a cylindrical meniscus shaped optical element. The cylindrical meniscus optical element in this example may be curved in one direction, for example, in the x-z plane. The variation in the boresight angle change with respect to the change in the angle of incidence (AoI) is obtained using a simulation program such as Zemax. As noted from FIG. 16(d-1), the boresight angle correction is about 2.7E-3 when the relative angle of incidence of the laser beam with respect to the meniscus optical element is about −30 degrees and the boresight angle correction is about −2.7E-3 when the relative angle of incidence of the laser beam with respect to the meniscus optical element is about 30 degrees. From FIG. 16(d-1) it is understood that by changing the relative angle of incidence of the laser beam with respect to the meniscus optical element between about −30 degrees and 30 degrees, the boresight angle can be changed in a range between about −2.7E-3 and about 2.7E-3 in this example.

FIG. 16(d-2) illustrates the variation in the boresight angle change expressed in milliradians (mrad) versus the change in the angle of incidence (AoI) which corresponds to the relative angle of incidence of the laser beam with respect to the meniscus optical element expressed in degrees measured for an implementation of a cylindrical meniscus shaped optical element. The cylindrical meniscus optical element in this example may be curved in the x-z plane. The measured variation in the boresight angle change with respect to the change in the angle of incidence (AoI) is compared with the simulated variation represented by curve 1615 similar to the curve shown in FIG. 16(d-1). As noted from FIG. 16(d-2), because the meniscus optical element is a cylindrical optical element curvature only in one direction, e.g., along the x-z plane, a change in the angle of incidence (AoI) along in the x-z plane (tip) brings about a greater change in the boresight angle as depicted by curve 1621 as compared to a change in the boresight angle brought about by a change in the angle of incidence (AoI) in the y-z plane (tilt) depicted by curve 1618. Furthermore, it is observed that the simulated change in boresight angle with respect to a change in the angle of incidence (AoI) depicted by curve 1615 corresponds with the measured change in the boresight angle brought about by a change in the angle of incidence (AoI) along the x-axis depicted by curve 1621.

FIG. 16(d-3) illustrates the measured variation in the boresight angle of an output laser beam expressed in milliradians (mrad) as a function of tilt about the x-axis of an implementation of a spherical meniscus shaped optical element depicted by curve 1625. The surfaces of the implementation of the spherical meniscus shaped optical element each have a radius of curvature of about 51.9 mm. The implementation of the spherical meniscus shaped optical element has a thickness of about 5 mm. In FIG. 16(d-3), the variation in the boresight angle of an output laser beam as a function of tilt about the x-axis for a simulated implementation of a spherical optical element having surfaces with a radius of curvature of about 51.9 mm and thickness 5 mm is depicted by curve 1630. It is noted from FIG. 16(d-3) that the measured variation in the boresight angle of an output laser beam as a function of tilt about the x-axis for the implementation of a spherical meniscus shaped optical element agrees with the simulated variation. It is further noted that a tilt about the x-axis between about −3 degrees and +3 degrees can produce a change in the output beam angle between about −1.75 mrad and +1.75 mrad.

FIG. 16(d-4) illustrates the measured variation in the boresight angle of an output laser beam expressed in milliradians (mrad) as a function of being tipped about the y-axis of an implementation of a spherical meniscus shaped optical element depicted by curve 1635. The surfaces of the implementation of the spherical meniscus shaped optical element each have a radius of curvature of about 51.9 mm. The implementation of the spherical meniscus shaped optical element has a thickness of about 5 mm. In FIG. 16(d-4), the variation in the boresight angle of an output laser beam as a function of rotation about the y-axis for a simulated implementation of a spherical optical element having surfaces with a radius of curvature of about 51.9 mm and thickness 5 mm is depicted by curve 1640. It is noted from FIG. 16(d-4) that the measured variation in the boresight angle of an output laser beam as a function of rotation about the y-axis for the implementation of a spherical meniscus shaped optical element agrees with the simulated variation.

It is further noted that a tip about the y-axis between about −3 degrees and 3 degrees can produce a change in the output beam angle between about +1.75 mrad and −1.75 mrad.

FIG. 16(e-1) depicts a laser beam with about 0.5 degree boresight error that is incident on an implementation of an optical element 1605A. The optical element 1605A can be translated vertically with respect to the incident beam (e.g., translated parallel to y-axis) such that the incident laser beam is output from the optical element 1605A after refraction at the first surface 1607 and the second surface 1609 with a boresight error of substantially 0 degrees. FIG. 16(e-2) illustrates an implementation of a translated configuration of the optical element 1605A. In the translated configuration, the optical element 1605A is displaced vertically upwards (e.g. upwards along the y-axis) with respect to the incident laser beam by about 2.9 mm. In various implementations, the thickness along the optical axis of the optical element 1605A, the surface characteristics (e.g., curvature, radius of curvature, surface sag, etc.) can be configured such that the optical element is displace by a different amount to achieve the same amount of correction. For example, in various implementations, the optical element 1605A can be displaced vertically upwards (along the +x-axis) or downwards (along the −x-axis) by a distance between about 0 mm and 10 mm to correct the boresight error from about 0 degrees to a boresight error less than 1.5 degrees In various implementations, the optical element 1605A can be displaced vertically and/or horizontally (e.g., along the ±y-axis and/or ±x-axis) by a distance between about 0 mm and 10 mm to correct the boresight error from about 0 degrees to a boresight error less than 0.01 degrees. The sensitivity can thus range between about 0.15 degrees/mm and 0.001 degrees/mm. The range of correction can range between 0 degrees and 1.5 degrees or between about 0 degrees and 0.01 degrees. Values outside these ranges are also possible.

In the multi-laser system 100 shown in FIG. 16(a), a plurality of optical paths are depicted. A first optical path originates at laser 101A, passes through the optical element 1605A, where laser boresight and opto-mechanical angular errors may be compensated through adjustment of the angle of incidence of the laser beam relative to the optical element 1605A and then arrives at the beam combining/positioning system 1000. The adjustment of the angle of incidence of the laser beam relative to the optical element 1605A can be accomplished by rotating the optical element 1605A (e.g., by adjusting the pitch and/or yaw of the optical element 1605A), and/or by translating the optical element 1605A with respect to the incident optical beam. A second optical path originates at laser 101B, passes through the Risley prism pair 705A, where laser boresight and opto-mechanical angular errors may be compensated through adjustment of the wedge angles of and the azmiuthal rotation between the prism pair 705A, and then arrives at the beam combining/positioning system 1000. An N-th optical path originates at laser 101N, passes through the Risley prism pair 705N, where laser boresight, and opto-mechanical angular errors may be compensated through adjustment of the wedge angles of the prism pair 705N, passes through glass etalon plates 707N, 708N, where laser centration and opto-mechanical lateral positioning errors may be compensated for by adjusting the pitch and/or yaw of the glass etalon plates 707N and/or 708N, and then arrives at the beam combining/positioning system 1000. As discussed above, meniscus optical elements may replace the Risley prisms. Accordingly, glass etalon plates 707N and/or 708N may be used in combination with meniscus optical elements to alter the vertical and/or horizontal beam position and/or correct centration error.

Propagating along these paths, laser beams 102A-102N, which may have originally been far from one another, are repositioned to be closer together as beams 1001A-1001N. In some embodiments, the beams 1001A-1001N are parallel to one another. In other embodiments, the beams 1001A-1001N are not parallel to one another. Other optical components (e.g., lenses, prisms, polarization rotators, waveplates, etc.) can be included to alter the laser beams and/or optical paths.

The optical element 1605A can comprise materials that are transparent to the wavelength of the incident light (e.g., wavelength of the output from the lasers 101A, 101B, . . . , 101B). For example, the optical element 1605A can include materials such as glass, polymer, polycarbonate, polyethylene terephthalate, glycol-modified polyethylene terephthalate, amorphous thermoplastic, and/or other substrates.

Implementations of optical element 1605A may be useful for systems such as described above or in spectroscopic analysis systems such as the systems disclosed in U.S. Publication No. 2014/0160786 which is incorporated herein by reference in its entirety. The implementations of optical element 1605A can also be used in other systems and devices as well and thus may be used independently of the systems described above. Other variations are also possible.

In various implementations, the plurality of lasers 101A, 101B, . . . , 101N; the beam positioning system 1000, the optical element 1605A, the Risley prism pair 705A, the etalon plate 707N, 708N can be enclosed in a thermally stable enclosure 150. In various implementations, the thermally stable enclosure 150 can include a material having a thermal conductivity of at least 5 W/(m K). The thermally stable enclosure 150 can be configured to maintain alignment of the laser beams to a target object 1100 over a range of ambient temperatures. In some embodiments, the optical fibers can be employed to direct light to the flow cell. Other variations are also possible. Similarly, in any method or process disclosed herein, steps or operations can be add, removed, and/or rearranged.

Part IV

As noted above, U.S. Provisional Patent Application No. 62/133,241, filed Mar. 13, 2015, and U.S. Provisional Patent Application No. 62/135,137, filed Mar. 18, 2015, are incorporated herein by reference in their entireties, and the systems and methods described herein are also described therein. As described above, for example, with respect to FIG. 2, the multi-laser system 100 may include optional beam focusing optics 117 to provide size reduction and/or shaping to the output laser beams 118, 119, 120. For example, the focusing optics 117 may change the shape of the laser beams. In some embodiments, for example, the laser beams 118, 119, 120 can have a generally Gaussian profile, so that when illuminating a flow cell, the intensity of the light illuminating the center of the flow cell is significantly greater than the intensity of the light illuminating the peripheral edges of the flow cell. Accordingly, in various configurations, an optical component may be employed to convert the Gaussian beam into a beam having a flat top profile. Additionally, having the beams of light 118, 119, 120 with elongated cross-sections that produce an elongated, for example, linear or line shaped spot size, so that the light extends further across the width of, for example, a flow cell may be desirable. By using a beam with an elongate cross section and spot shape, for example, having the shape of a line, and having a flat top distribution, a more uniform distribution of light across the width of the flow cell or other target output can be achieved while illuminating a relatively small longitudinal area along the length of the flow cell and maintaining substantially uniform high light intensity. See also FIG. 12 and the discussion of the optical elements 5118A-5118D.

In various configurations, a Powell lens may be used to convert a Gaussian beam into a beam having an elongated (e.g., line-shaped) cross-section and spot with a flat top distribution. A change in the size of the beam incident on the Powell lens, for example, a change in the beam width as a result of aging of the laser may, however, alter the output of the Powell lens. A description of a component that includes a Powell lens and that is configured to be adjustable to accommodate for changes in beam size of the input laser beam is provided below. An example Powell lens is disclosed in U.S. Pat. No. 4,826,299.

Such a component may be useful for systems such as described above, for example, in either or both Part I and Part II, but may be used in other systems and devices as well and thus may be used independently of the systems described above. Variations are also possible.

Figure 17A:
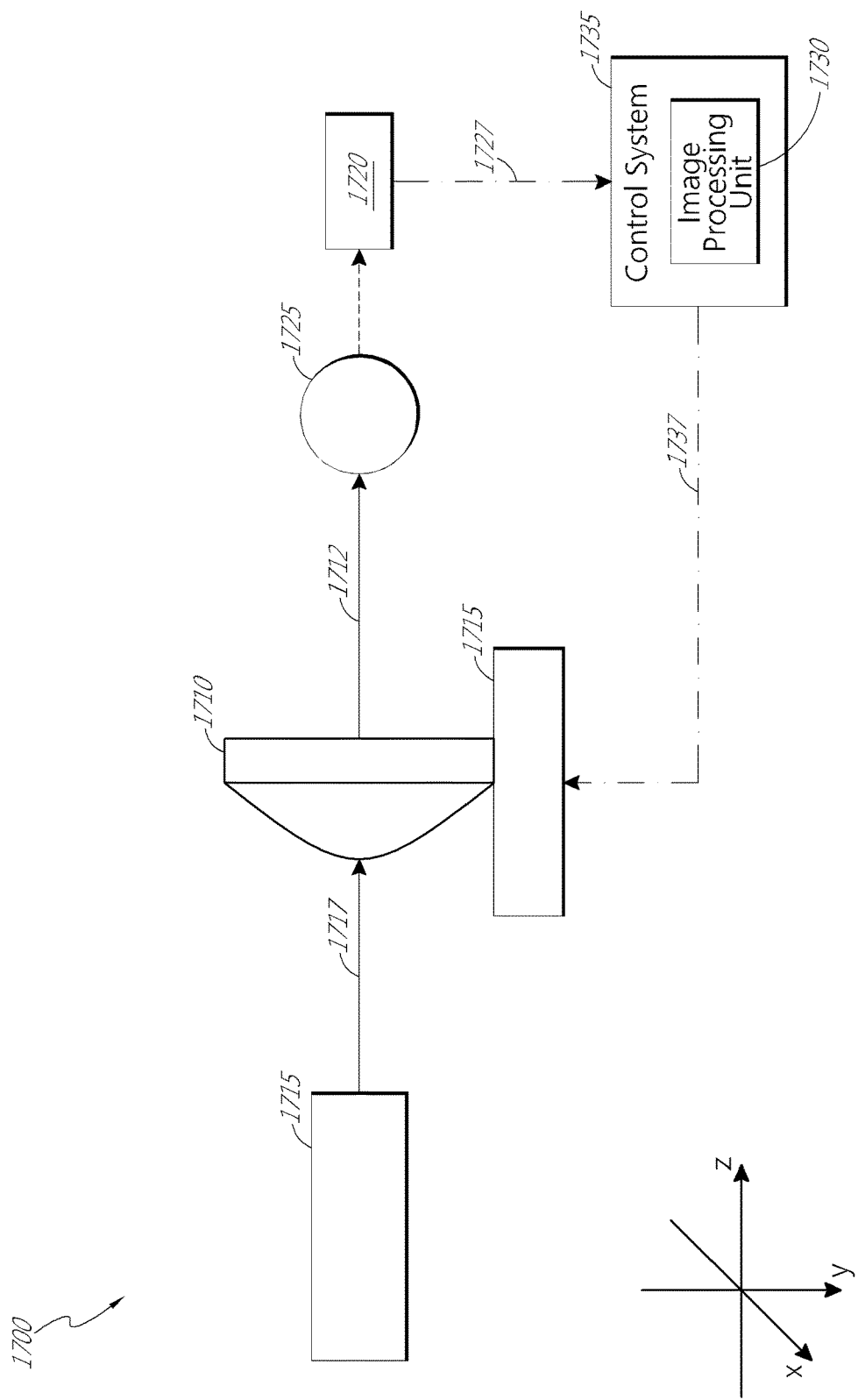
FIG. 17a depicts a laser system in which a Powell lens is used.
Figure 17B:
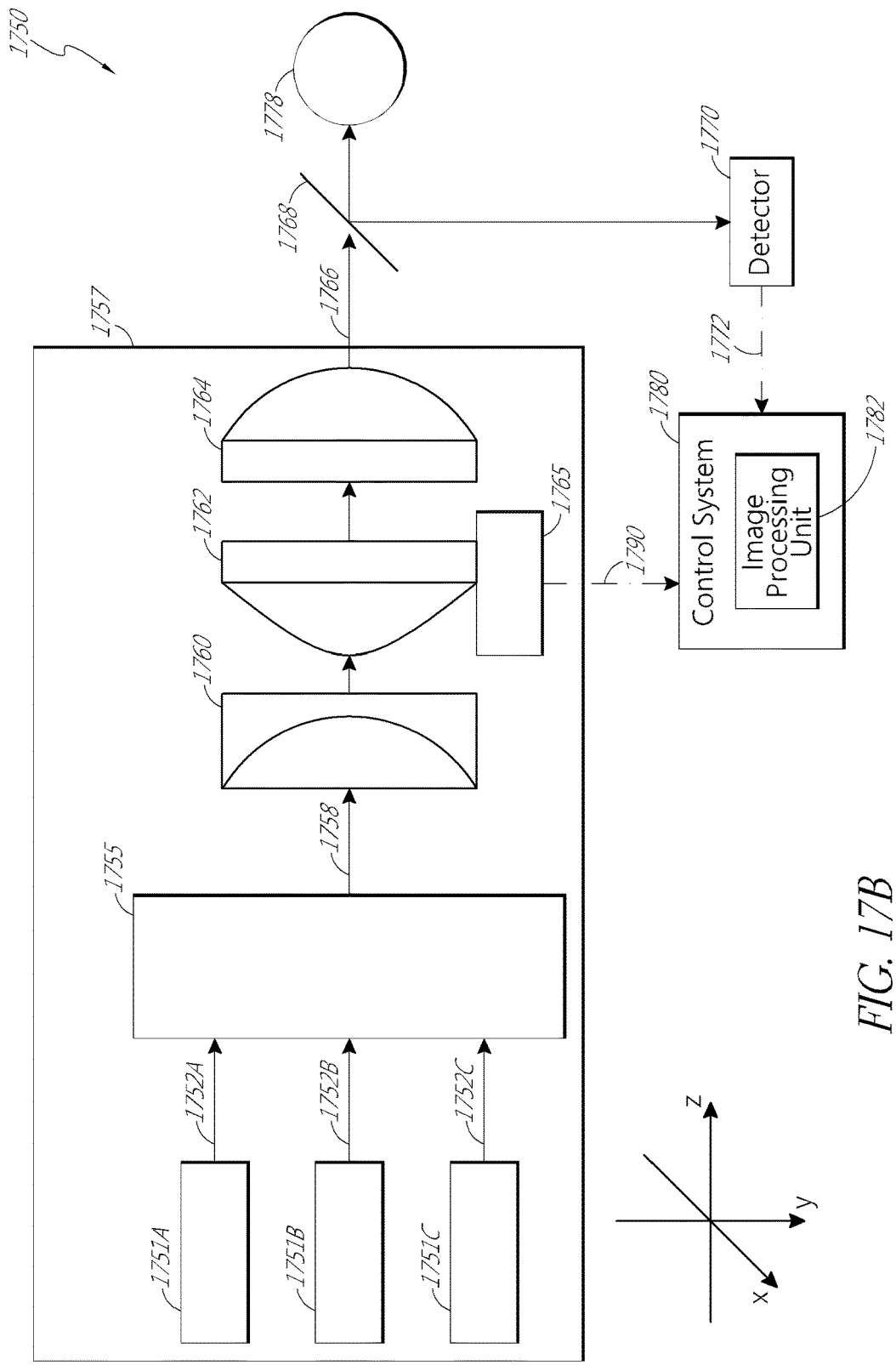
FIG. 17b depicts a laser system in which a Powell lens is used.

FIGS. 17A and 17B depict example embodiments of laser systems in which a Powell lens is used. In the embodiment of FIG. 17A, a laser 1705 emits a laser beam 1707, which is incident on a beam focusing optics configuration: a negative lens 1709, a Powell lens 1710, and a positive lens 1711. In some configurations, the negative lens 1709 and the positive lens 1711 can be an afocal system such as a telescope optical design and may be a Galilean configuration. In various embodiments, other lenses can be used as part of this beam focusing optics. In some situations, this incident laser beam 1707 on the negative lens 1709 can be referred to as an input to the beam focusing optics configuration. Similarly, in some situations, output laser beam 1712 can be viewed as an output of the beam focusing optics unit. In another embodiment, the negative lens 1709 and positive lens 1711 can be rearranged in position, for example locations of the positive lens and negative lens may be reversed with the positive lens receiving the laser beam prior to the negative lens. In some configurations the negative lens 1709 and the positive lens 1711 are separated by the difference in the absolute value of their respective focal lengths. Accordingly, if you treat the negative lens 1709 as having a negative focal length, the distance between the negative lens and the positive lens 1711 is the sum of the focal lengths. Variations of in the design of the beam focusing optics are possible.

In various embodiments, the output laser beam 1712 can have a Gaussian beam profile. The Powell lens 1710 is configured to convert the resulting laser beam of negative lens 1711 that has a Gaussian beam profile into a laser beam having a flat top intensity distribution and an elongated cross-section orthogonal to propagation of the beam, with the elongated cross-section having a length in a first direction that is longer than in a second orthogonal direction. The Powell lens 1710, however, is sensitive to the size of the Gaussian beam and performance is improved for that particular size beam. However, with time a laser ages and the beam size changes. The negative lens 1709 is therefore configured to alter the beam size of the laser beam 1707 in at least one direction. The Powell lens 1710 can then convert the laser beam exiting the negative lens 1711 and incident on the Powell lens that has a Gaussian beam profile into a laser beam having a flat top intensity distribution and an elongated cross-section orthogonal to propagation of the beam. This elongated cross-section has a length in a first direction that is longer than in a second orthogonal direction. The output laser beam 1712 from the Powell lens 1710 subsequently propagates to the positive lens 1711. The positive lens 1711 is configured to collimate the laser beam from the Powell lens 1710 in at least one direction. In various embodiments, the negative lens 1711 and positive lens 1709 can be cylindrical lenses.

To accommodate variation in the beam size output by the laser beam, for example, over time, the Powell lens 1710 is coupled to a translation stage 1715. This translation stage 1715 can move the Powell lens 1710 so that the diameter of the laser beam 1707 incident on the Powell lens 1710 can be adjusted to a size for which the Powell lens performs well by producing the desired elongated (e.g., linear) spot having a flat top intensity distribution. In the configurations shown in FIG. 17A, the laser beam 1712 after passing through the Powell lens 1710 and the positive lens 1711 is received by a target 1725, and subsequently a detector 1720.

In some configurations, the detector 1720 can transmit a detector output signal 1727 to a control system 1735, which may include an image processing unit 1730. The control system 1735 can process the signal 1727 as feedback. With this feedback processed in image processing unit 1730, the control system can determine whether an adjustment to the translation stage 1715 may be helpful. An adjustment to the position of the translation stage 1715, for example, along the longitudinal axis of the Powell lens, (e.g., along the z-axis) can be determined based on the feedback. Such an adjustment can move the translation stage along the z-axis (e.g., in a longitudinal direction along the optical axis laser beam 1707) to a z-axis plane where the output received by the detector is has a more linear shaped spot and/or a more flat top distribution.

The control system 1735 can generate and send one or more control signals 1737 to the translation stage 1715 to adjust the translation stage in position (e.g., a movement of the position of the translation stage 1715), thereby adjusting the Powell lens in position. Because the first lens in the beam focusing system, the negative lens 1709 in FIG. 17A causes the beam to diverge, the change in the position of the Powell lens 1710 and the distance of the Powell lens from the negative lens can result in a change in diameter of the laser beam 1707 incident on the Powell lens.

Control system 1735 can use the image processing result generated by image processing unit 1730 to generate one or more signals configured for use at the translation stage 1715. The one or more signals can be communicated as an electrical signal (e.g., a series of varying voltages) as the signal to the translation stage 1715. In various other embodiments, the one or more signals can be communicated (depicted as alternating dotted line in FIG. 17A) via a wireless medium, an optical medium (e.g., a fiber optic cable), etc. The one or more signals can adjust the position of the translation stage 1715 in a longitudinal direction along the z-axis (or possible in lateral directions, e.g., in either the x-axis or y-axis, as discussed herein). In some embodiments, the one or more signals can correspond to a two-dimensional movement or a three-dimensional movement of the translation stage 1714. In particular, in some configurations, a movement in the Powell lens 1710 in a lateral direction, in response to one or more signals (e.g., a control signal), can adjust the angular direction of the laser beam 1707 incident on the negative lens 1709. Such an adjustment can, in some cases, reduce boresight error and/or to adjust the centration of the laser beam 1707.

The laser 1705 may comprise a diode laser, a solid-state laser, a frequency-doubled laser, and/or another types of laser. Laser 1705 can output a laser beam 1707. Laser beam 1707 can propagate to Powell lens 1710, with the laser beam having a portion of the beam width incident on a roof of the Powell lens 1710.

Powell lens 1710 can include other types of Powell lens. The Powell lens 1710 can convert laser beam 1705 that has a Gaussian beam profile into the output laser beam 1712 having a flat top intensity distribution and an elongated cross-section orthogonal to propagation of the beam, with the elongated cross-section having a length in a first direction that is longer than in a second orthogonal direction. Some examples of Powell lenses are discussed in U.S. Pat. No. 4,826,299. In some embodiments, the Powell lens includes a surface having an apex resembling a curved roof line. Such a lens can generate a line shaped beam cross-section or spot. In some embodiments, the surface having the rounded roof shaped surface (referred to herein as a roof having a roofline with a roof angle or apex angle) is a complex two-dimensional aspheric curve. In some embodiments, this two-dimensional aspheric curve generates spherical aberration that redistributes the light along a line. This spherical aberration may also cause a decrease in the light in the center of the line and an increase in the light at the ends of the line. In various configurations, the light fans out at a fan angle that is a function of the refractive index of the lens material and the roof angle. For example, in some cases a steeper roof and higher refractive index of the lens material causes a wider fan angle increases the length of the line.

Target 1725 may comprise a flow cell, a flow cell mount, a light pipe, a waveguide, an optical fiber, or a lab on a chip. In some embodiments, the target object may comprise a mounting mechanism, mounting system (e.g., mounting alignment system), etc. for a flow cell, a flow cell mount, a light pipe, a waveguide, an optical fiber, and/or a lab on a chip. Target 1725 can be a translucent medium that can further propagate output laser beam 1712 to detector 1720 (depicted as a dotted line in FIG. 17A).

Detector 1720 can be a photodetector array that detects the beam passing through a target 1725, for example, the target 1725 can be a flow cell with a liquid medium that may transmit the beam 1712 outputted from the beam focusing optics comprising the Powell lens 1710. The detector 1720 can transmit a signal 1727. Signal 1727 can be transmitted in a variety of ways. In some embodiments, detector 1720 is a photodetector that transmit the signal 1727 as an electrical signal (e.g., a voltage). Detector 1720 can also include a wireless transmitter that transmits signal 1727 as a wireless signal. Or in another embodiment, detector 1720 can include an RF transmitter that transmits 1727 as an RF signal. As can be seen by this description, various methods of communicating signal 1727 from detector 1720 are possible in the laser system 1700 (depicted as alternating dotted line in FIG. 17A).

Control system 1735 receives at least signal 1727 to be used as feedback for the laser system 1700. Control system 1730 can use the feedback to determine whether to adjust the position of translation stage 1715. In various embodiments, image processing unit 1730 can uses various image processing approaches to process signal 1727, and thereby generate an image processing result that is assessed by the control system which produces a control signal for driving the translator as a result. In some configurations, control system 1735 can include a user interface that displays the optical power distribution. A signal for driving the translation stage based on input from the user having seen the optical power distribution (or shape of the laser spot) can be produced by the control system. As discussed above, for example, in some cases, the optical power distribution can be a uniform line (e.g., a uniform line having a flat top optical signal 1712 outputted by the Powell lens). In other cases, the optical power distribution can be a non-uniform (e.g., the power distribution is split into at least two peaks with a higher power concentrated in these portions corresponding to a distortion in the optical signal 1712 outputted from the Powell lens) or the spot may not be a line.

In some embodiments, human intervention is not needed and feedback from the detector can be use by the control system to automatically adjust the translation stage such that improved output is obtained at the target. In some configurations, for example, control system 1735 can determine that the image processing result generated by image processing unit 1730 corresponds to a distortion in the optical beam 1712. This distortion can result from a change of the diameter of laser beam 1707 incident on the Powell lens 1710. With this distortion identified, control system 1735 can determine, possibly using an iterative or dithering process, a change in the position of the translation stage 1750 that improves the optical beam by changing the position of the Powell lens 1710 and changing in the diameter of the laser beam 1707. A change in the diameter of the laser beam 1707 can result, for example, in a more uniform power distribution of optical signal 1712 (e.g., a substantially uniform power distribution). A uniform power distribution can result in a more optimal testing condition for biological samples being tested at flow cell 1725. Accordingly, the control system 1730 can use the feedback to create a control system loop that maintains the position of the translation stage so that a uniform power distribution or more desirable spot shape (e.g., linear) is maintained on the target 1725. The detector 1720 can continue to receive the optical signal that can indicate, after processing by the control system 1730, whether or not a loss of power has occurred at the flow cell, whether or not the pattern of the power distribution has changed at the flow cell, or various other measurements that can be used by the control system 1730 to maintain an optimal optical properties (e.g., a power distribution) emanating from Powell lens 1730.

As discussed above, in various embodiments, the one or more signals can be received via user input as part of a user interface associated with control system 1735. For example, in one embodiment, control system 1735 can include a display configured to display information based on the optical image of the cross-sectional shape and/or intensity distribution of the output laser beam 1712 for a user to view. In one embodiment, the display can show the image processing result (e.g., a representation of the optical image) generated by image processing unit 1730. The user can then determine whether the translation stage is to be translated and input information into the user interface to move the translation stage 1715. In other embodiments, the one or more signals can be automatically and/or dynamically determined when control system 1735 receives feedback from detector.

Translation stage 1715 can be any mechanical apparatus or device capable of moving an attached lens. For example, translation stage 1715 can include an actuator that receives and can respond to a control signal (e.g., one or more signals a control system 1735). The actuator can be a motor or piezo device that can generate a force that actuates movement of the translation stage 1715, thereby moving the Powell lens 1710 coupled to the translation stage 1715. As discussed above, in some configurations, the translation stage 1715 can move to adjust the angular and/or lateral position of the laser beam 1707 so that the boresight and centration errors of the laser 1705 are compensated for.

FIG. 17B depicts an example embodiment of a multi-laser system. The multi-laser system 1750 depicted in FIG. 17B comprises a thermally stable, temperature controlled enclosure 1757 configured to mechanically and/or thermally couple to a target object 1778. The enclosure 1757 helps to isolate the laser and optics within the enclosure 1757 from the ambient environment, which may have varying temperature. In some embodiments, the target object may comprise a flow cell, a flow cell mount, a light pipe, a waveguide, an optical fiber, or a lab on a chip. In some embodiments, the target object may comprise a mounting mechanism, mounting system (e.g., mounting alignment system), etc. for a flow cell, a flow cell mount, a light pipe, a waveguide, an optical fiber, and/or a lab on a chip.

The multi-laser system 1750 includes a plurality of lasers 1751A-1751C, enclosed within the thermally stable enclosure 1757. The plurality of lasers 1751A-1751C may comprise diode lasers, solid-state lasers, frequency-doubled lasers, and/or other types of lasers. The plurality of lasers 1751A-1751C output a plurality of respective laser beams 1752A-1752C. Each of the laser beams 1752A-1752C may have a wavelength different from the other laser beams.

In some embodiments in which the system 1750 is used perform testing of biological samples, flow cells are illuminated with the laser beam 1766. Fluorescent dyes absorb light at certain wavelengths and in turn emit their fluorescence energy at a different wavelength. This emission can be detected to ascertain properties of the fluid in the flow cell.

The system shown in FIG. 17B includes beam focusing optics comprising a negative lens 1760, a Powell lens 1762, and a positive lens 1764 can assist in acquisition of test results. As discussed above, the negative lens 1760 and a positive lens 1764 may be arranged to form an afocal system. For example, the negative lens 1760 and a positive lens 1764 may be arranged to form a telescope such as Galilean configuration. In some configurations, for example, the negative lens 1760 and positive lens 1764 are separated by the distance that is the difference of the absolute value of their respective focal lengths. In other configurations, the negative lens 1760 and positive lens 1764 can be reversed in position, with the positive lens prior to the Powell lens and the negative lens after the Power lens in the optical path from the laser to the target. Variations in the telescope design or the beam focusing optics are possible.

The multi-laser system 1750 also includes a beam combiner 1755 that outputs a laser beam 1758 with the wavelengths of the plurality of laser beams 1752A-1752C. The laser beam 1758 propagates to the beam focusing optics comprising the negative lens 1760, the Powell lens 1762 coupled to the translation stage 1765, and the positive lens 1764, with an output laser beam 1766. In various embodiments, the output laser beam 1766 can have a Gaussian beam profile. The negative lens 1760 is configured to alter the beam size of the laser beam 1758 in at least one direction. The Powell lens 1762 is configured to convert the resulting laser beam of negative lens 1760 that has a Gaussian beam profile into a laser beam having a flat top intensity distribution and an elongated cross-section orthogonal to propagation of the beam, with the elongated cross-section having a length in a first direction that is longer than in a second orthogonal direction. The positive lens 1764 is configured to collimate the laser beam from the Powell lens 1762 in at least in one direction. In various embodiments, the negative lens 1762 and positive lens 1764 can be cylindrical lenses.

The laser beam 1766 propagates to a beam splitter 1768 that receives the laser beam and splits the laser beam into at least one beam that is directed to the detector 1770 and at least one beam to the target 1778. The detector 1770 is disposed to receive an image of the cross-sectional shape and intensity distribution of the laser beam 1766. As described above with respect to FIG. 17A, the detector 1770 can be a photodetector array that sends a signal 1772 (e.g., an optical image) to control system 1780. Further, signal 1772 can be transmitted in a variety of methods/ways as described with respect to FIG. 17A and depicted as an alternating dotted line.

Control system 1780 is configured to provide the control signal 1790 to adjust translation of the translation stage 1765 based on analysis by the image processing unit 1782 of the image received by the detector 1770. The control system 1780 can also be configured to receive input from a user, and, in turn, provide the control signal 1790 to adjust translation (e.g., a position) of the translation stage 1765 based on the input from a user. Further, control signal 1790 can be transmitted in a variety of methods/ways as described with respect to FIG. 17A and depicted as an alternating dotted line.

The translation stage 1765 is configured to translate the Powell lens 1762 in a longitudinal direction either closer to the negative lens 1760 and farther from the positive lens 1764, or farther from the negative lens 1760 and closer to positive lens 1764 in the control signal 1790. Additionally, translation stage 1765 can be configured to translate the Powell lens 1762 in a lateral direction in response to the control signal 1790 to adjust angular direction of the laser beam 1758 to reduce boresight error and/or to adjust the centration of the laser beam 1758. As described above with respect to FIG. 17A, variations of the translation stage 1765 are possible.

Figure 18:
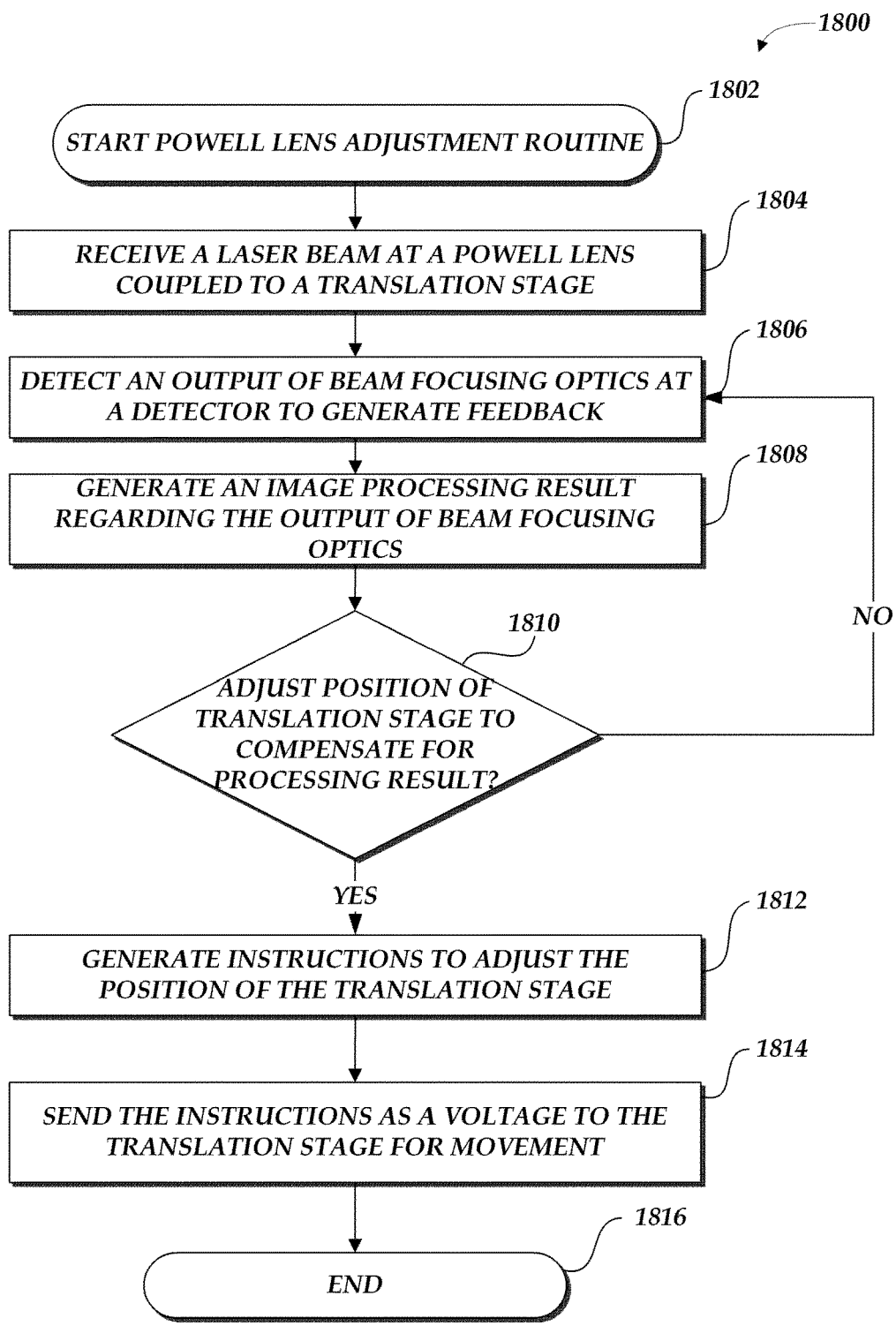
FIG. 18 illustrates an example method using a Powell lens in a laser system.

FIG. 18 depicts an exemplary method 1800 using a Powell lens system as part of a laser system. For example, system 1700 or system 1750 depicted in FIGS. 17A and 17B respectively can use the flow of the Powell lens adjustment routine to adjust the position of the Powell lens in their respective systems. This process may be performed automatically using feedback from a detector or manual by a user who evaluates the optical beam received by the detector and based on such evaluation provides a control signal to the translation stage. In the later case, the user may be located remotely and the system need not be opened to adjust the Powell lens and the beam.

A wide variety of other variations are possible. Components can be added, removed, and/or rearranged. For example, in some embodiments, the optical system does not include a thermally conductive housing or a thermoelectric controller. In some embodiments, the optical fibers can be oriented to direct light to the flow cell without the use of lenses or other optical elements. Other variations are also possible. Similarly, in any method or process disclosed herein, steps or operations can be add, removed, and/or rearranged.

Reference throughout this specification to "some embodiments," "certain embodiments," or "an embodiment" means that a particular feature, structure or characteristic described in connection with the embodiment is included in at least some embodiments. Thus, appearances of the phrases "in some embodiments" or "in an embodiment" in various places throughout this specification are not necessarily all referring to the same embodiment and may refer to one or more of the same or different embodiments. Furthermore, the particular features, structures or characteristics may be combined in any suitable manner, as would be apparent to one of ordinary skill in the art from this disclosure, in one or more embodiments.

As used in this application, the terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

Similarly, it should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Rather, inventive aspects lie in a combination of fewer than all features of any single foregoing disclosed embodiment.

Although the inventions presented herein have been disclosed in the context of certain preferred embodiments and examples, it will be understood by those skilled in the art that the inventions extend beyond the specifically disclosed embodiments to other alternative embodiments and/or uses of the inventions and obvious modifications and equivalents thereof. Thus, it is intended that the scope of the inventions herein disclosed should not be limited by the particular embodiments described above.

What is claimed is:

1. An optic system comprising:
   a first lens for receiving a laser beam having a Gaussian beam profile, said first lens configured to alter the beam size of the laser beam in at least one direction;
   a Powell lens configured to convert said laser beam that has a Gaussian beam profile into a laser beam having a flat top intensity distribution and an elongated cross-section orthogonal to propagation of the beam, said elongated cross-section having a length in a first direction that is longer than in a second orthogonal direction;
   a second lens configured to collimate said laser beam at least in one direction;
   a translation stage configured to receive a control signal that drives movement of said translation stage,
   wherein said Powell lens is coupled to the translation stage such that the Powell lens is configured to be translated with respect to said first and second lens in response to said control signal.

2. The system of claim 1, wherein the first lens is a negative lens and the second lens is a positive lens.

3. The system of claim 1, wherein the translation stage is configured to translate the Powell lens in a longitudinal direction either closer to the first lens and farther from the second lens or farther from the first lens and closer to the second lens in response to said control signal.

4. The system of claim 1, wherein the translation stage is configured to translate the Powell lens in a lateral direction in response to said control signal to adjust angular direction of the laser beam to reduce boresight error, and/or to adjust the centration of the laser beam, and/or to adjust an intensity profile of an output flat top line beam.

5. The system of claim 1, wherein the translation stage comprises at least one actuator configured to move said translation stage in response to said control signal.

6. The system of claim 1, further comprising a detector disposed to receive said laser beam after being output by said group of first and second lenses having the Powell lens therebetween, said detector disposed to receive an image of the cross-sectional shape and intensity distribution of the laser beam.

7. The system of claim 6, further comprising a beam splitter that receives said laser beam and splits said laser beam into at least one beam that is directed to said detector.

8. The system of claim 7, further comprising a control system including an image processing unit, wherein the control system is configured to provide the control signal to adjust translation of the translation stage based on analysis by the image processing unit of the image received by the detector.

9. The system of claim 1, further comprising a control system configured to receive input from a user, wherein the control system is configured to provide the control signal to adjust translation of the translation stage based on the input from the user.

10. The system of claim 9, further comprising a display configured to display a representation of an image of the cross-sectional shape and/or intensity distribution of the laser beam for said user to view to determine whether the translation stage is to be translated.

* * * * *